United States Patent
LaBorde

(10) Patent No.: US 9,928,342 B1
(45) Date of Patent: Mar. 27, 2018

(54) SYSTEM, MEDICAL ITEM INCLUDING RFID CHIP, SERVER AND METHOD FOR CAPTURING MEDICAL DATA

(71) Applicant: Brain Trust Innovations I, LLC, Tucker, GA (US)

(72) Inventor: David LaBorde, Tucker, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 0 days.

(21) Appl. No.: 15/704,494

(22) Filed: Sep. 14, 2017

Related U.S. Application Data

(63) Continuation-in-part of application No. 15/592,116, filed on May 10, 2017, which is a continuation of application No. 15/390,695, filed on Dec. 26, 2016, now Pat. No. 9,679,108, which is a continuation of application No. 15/004,535, filed on Jan. 22, 2016, now Pat. No. 9,569,589.

(60) Provisional application No. 62/113,356, filed on Feb. 6, 2015.

(51) Int. Cl.
| | |
|---|---|
| *G06F 19/00* | (2018.01) |
| *G06N 3/04* | (2006.01) |
| *G06N 3/08* | (2006.01) |
| *G06K 7/10* | (2006.01) |

(52) U.S. Cl.
CPC ....... *G06F 19/323* (2013.01); *G06K 7/10366* (2013.01); *G06N 3/04* (2013.01); *G06N 3/08* (2013.01)

(58) Field of Classification Search
CPC .......... G06K 7/10366; G06K 7/10009; G06K 7/10316; G06K 19/0723; G06K 7/10356; G06K 19/0717; G06K 7/0008
USPC ....................................................... 340/10.1
See application file for complete search history.

(56) References Cited

U.S. PATENT DOCUMENTS

| | | | | |
|---|---|---|---|---|
| 7,852,221 | B2 * | 12/2010 | Tuttle | G06K 7/10346 340/10.1 |
| 8,181,875 | B2 * | 5/2012 | Nishido | G06K 19/0701 235/451 |
| 8,547,248 | B2 * | 10/2013 | Zdeblick | A61B 5/0028 340/870.28 |
| 9,227,024 | B2 * | 1/2016 | Deutsch | A61M 5/5086 |
| 9,642,967 | B2 * | 5/2017 | Ribble | G06F 19/3418 |
| 2011/0291809 | A1 * | 12/2011 | Niemiec | A61B 5/0002 340/10.1 |

* cited by examiner

*Primary Examiner* — Mark Blouin
(74) *Attorney, Agent, or Firm* — Culpepper IP, PLLC; Kerry S. Culpepper

(57) ABSTRACT

A system that includes a plurality of RFID tags affixed to medical items, and a plurality of data collection engine devices, client devices and backend devices. The backend devices include trained machine learning models, business logic, and attributes of a plurality of patient events. A plurality of data collection engines and hospital information systems send attributes of new patient events to the backend devices. The backend devices can predict particular outcomes of new events based upon the attributes of the new events utilizing the trained machine learning models. Using business logic and the trained machine learning models, the backend devices can also make recommendations to optimize the patient flow in healthcare provider organizations.

18 Claims, 53 Drawing Sheets

920

Event 1: Medical Item ID Removed from Package, Time of Removal, Location of Removal, Package in Disposal Time, Location
Event 2: Medical Item Used by ID of Medical Professional at Start Time, Location, End Time
Event 3: Medical Item Used for Patient ID at Start Time, Location, End Time
Event 4: Medical Item Disposed at Time, Location

DCE

940

Medical Item ID Consumed by Actor ID on Behalf of Patient ID

Server

FIG. 9G

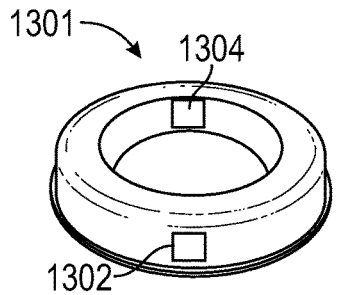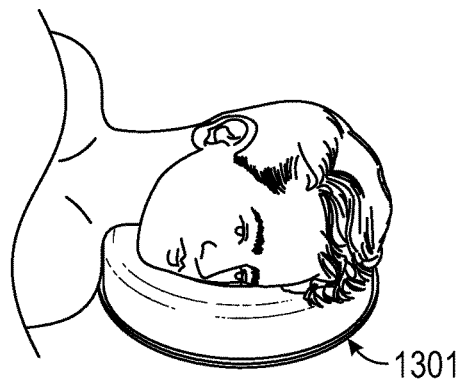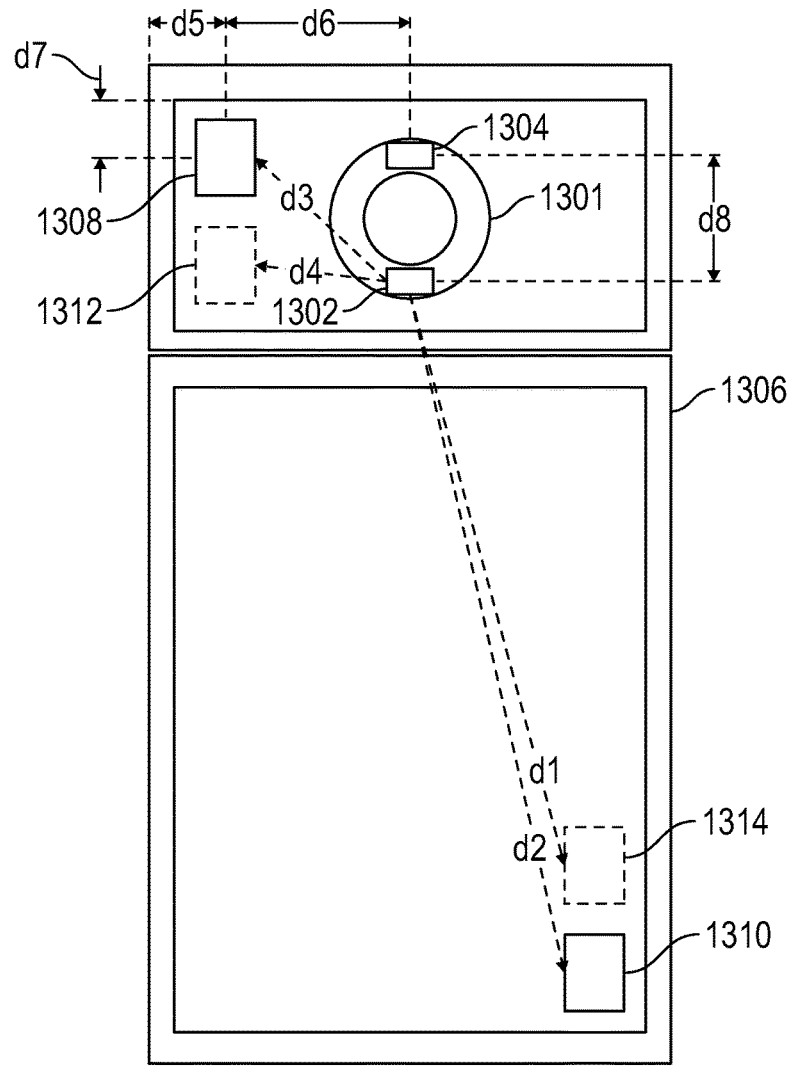
FIG. 13A
FIG. 13B
FIG. 13C

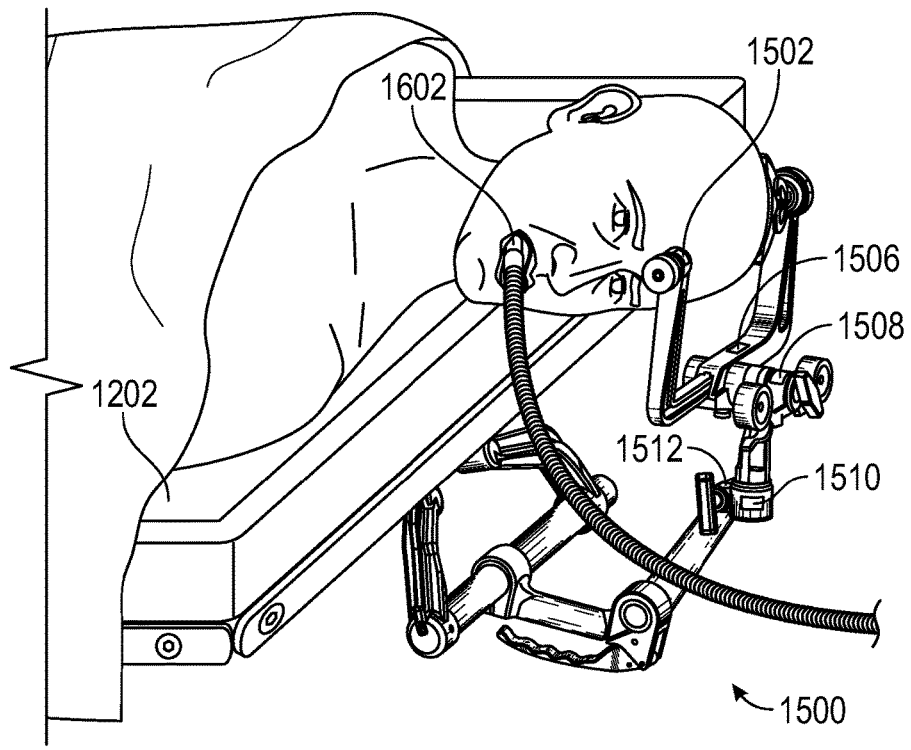
FIG. 17
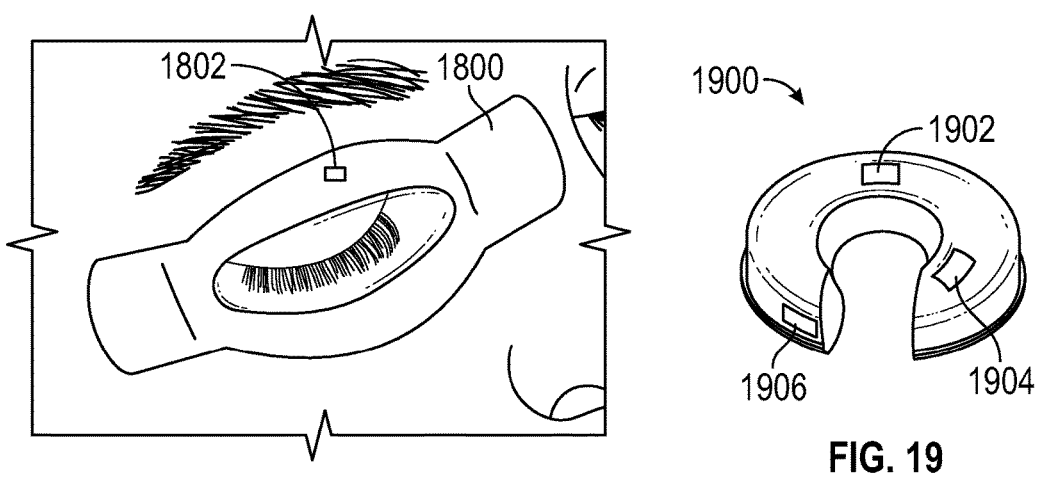
FIG. 18
FIG. 19

Data Fields/Properties

|  | Property 1 | Property 2 | Property 3 | ... | Property N |
|---|---|---|---|---|---|
| Data 1 |  |  |  |  |  |
| Data 2 |  |  |  |  |  |
| Data 3 |  |  |  |  |  |
| ... |  |  |  |  |  |
| Data N |  |  |  |  |  |

Collected Data

FIG. 28B

Value Plotted on Actual Range
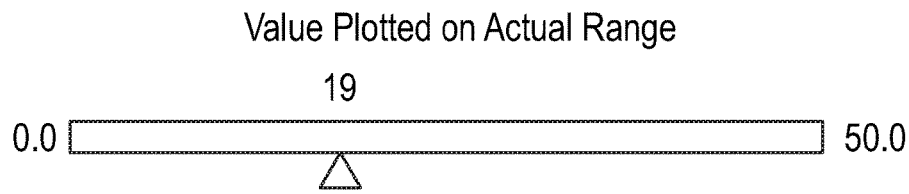
FIG. 29A
Equivalent Value Plotted on Normalization Scale
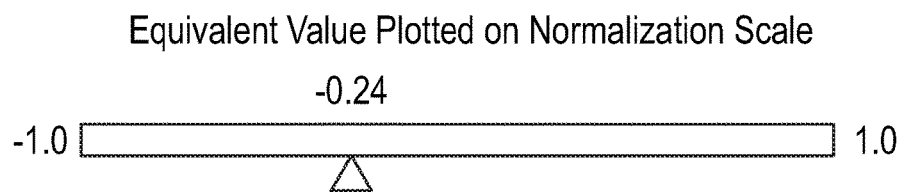
FIG. 29B
One-of-N Encoding
| Discharging Specialty |
|---|
| Hospital Medicine |
| General Surgery |
| Orthopedic Surgery |
Encoding →
| Discharging Specialty |
|---|
| 1.0, 0.0, 0.0 |
| 0.0, 1.0, 0.0 |
| 0.0, 0.0, 1.0 |
FIG. 30A
Equilateral Encoding
| Discharging Specialty |
|---|
| Hospital Medicine |
| General Surgery |
| Orthopedic Surgery |
Encoding →
| Discharging Specialty |
|---|
| 0.5, 1 |
| 0.933, 0.25 |
| 0.06698, 0.25 |
FIG. 30B

```
MODEL TRAINING STARTING...
Iteration No 1:   Error: 0.1792589605373940
Iteration No 2:   Error: 0.1413084705966610
Iteration No 3:   Error: 0.1132205445041410
Iteration No 4:   Error: 0.0995163267720716
Iteration No 5:   Error: 0.0966171008547308
Iteration No 6:   Error: 0.0893318057416419
Iteration No 7:   Error: 0.0837654002315370
Iteration No 8:   Error: 0.0743278915154816
Iteration No 9:   Error: 0.0651697895766448
Iteration No 10:  Error: 0.0561854946146632
Iteration No 11:  Error: 0.0470042597424259
Iteration No 12:  Error: 0.0382412320601650
Iteration No 13:  Error: 0.0308601909551354
Iteration No 14:  Error: 0.0229350764194705
Iteration No 15:  Error: 0.0200080379163413
Iteration No 16:  Error: 0.0144926705548749
Iteration No 17:  Error: 0.0096559103573012 1
Iteration No 18:  Error: 0.0059682892602663 8
Iteration No 19:  Error: 0.0033930633669103 2
Iteration No 20:  Error: 0.0017494910764920 7
Iteration No 21:  Error: 0.0008967381131869 7
-->21 training iterations required to attain global error < 0.001
--- MODEL TRAINING COMPLETE ---
```

FIG. 43

```
MODEL VALIDATION PROCEDURE STARTING...
Input: 1.0, 1.0, 0.0    Ideal : 0.0    Predicted: 2.9980141272379E-08
Input: 1.0, 0.0, 1.1    Ideal : 0.0    Predicted: 2.9979525096047E-08
Input: 1.0, 1.0, 1.0    Ideal : 0.0    Predicted: 2.9979472178447E-08
Input: 1.0, 0.0, 0.0    Ideal : 1.0    Predicted: 0.95092007944623
Input: 0.0, 0.0, 1.0    Ideal : 0.0    Predicted: 0.02318925183107
Input: 0.0, 0.0, 1.0    Ideal : 0.0    Predicted: 2.9979472447306E-08
Input: 0.0, 1.0, 0.0    Ideal : 0.0    Predicted: 2.9979472529752E-08
Input: 0.0, 1.0, 1.0    Ideal : 0.0    Predicted: 2.9979472178446E-08

---MODEL VALIDATION COMPLETE---
```

FIG. 44

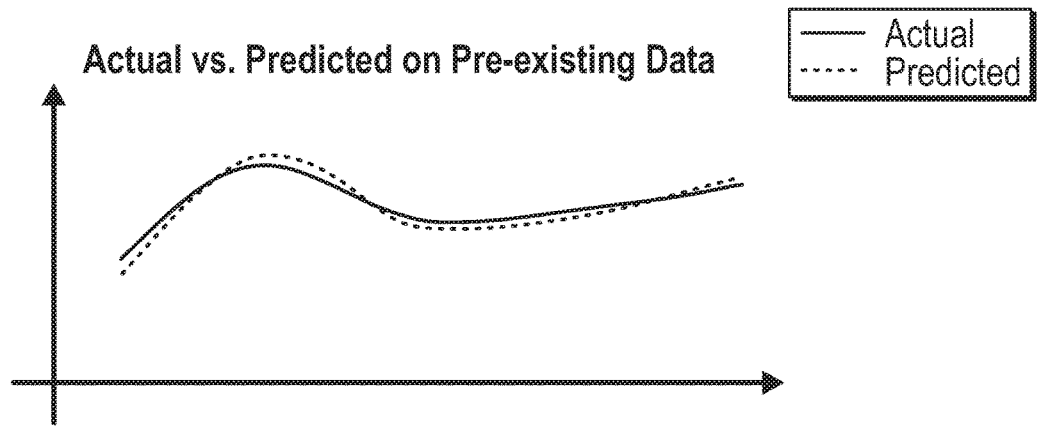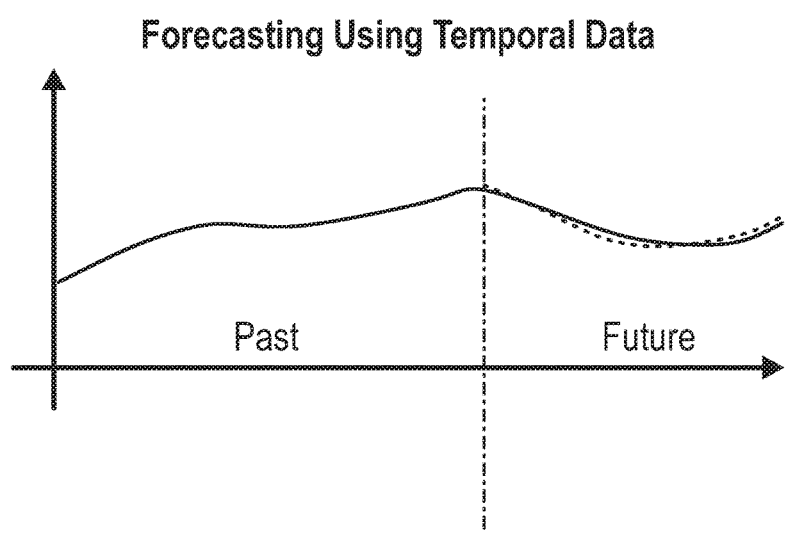
FIG. 46

Exemplary Reporting Matrix View - Roll Up / Drill Down
System > Facility > Service Line / Nursing Service / Physical Location*

Selected Metric: [Total Discharge Lag ▽] Target: <30 min - 92% of the time    Selected Time Frame: [Trailing Twelve Months ▽]

| Entity | Average D/C Lag (min) | %D/C Lag at or Below Goal |
|---|---|---|
| ▽System Level | 33.5 | 87.5% |
| ▷Facility A | 22.0 | 93.0% |
| ▷Facility B | 45.0 | 82.0% |
| ▽Clinical service lines | 45.0 | 82.0% |
| ▷General Surgery | 53.0 | 71% |
| ▽Internal Medicine | 37.0 | 93% |
| ▷Attending Physician for patient visit | 45.0 | 82.0% |
| ▷Physician One MD | 52.0 | 75% |
| ▷Physician Two MD | 38.0 | 89% |
| ▷Provider writing D/C or Tx order | 45.0 | 82.0% |
| ▷Physicians (MDs/DOs) | 30.0 | 92% |
| ▷Extenders (NPs/PAs) | 60.0 | 72% |
| ▽Nursing services | 45.0 | 82.0% |
| ▷Critical Care Nursing | 24.0 | 92% |
| ▷Medical Critical Care Nursing | 35.0 | 88% |
| ▷Nurse One RN | 41.0 | 87% |
| ▷Nurse Two RN | 29.0 | 89% |
| ▷Surgical Critical Care Nursing | 13.0 | 96% |
| ▷Medical Surgical Floor Nursing | 51.0 | 75% |
| ▷Post Operative Care Unit Nursing | 60.0 | 79% |
| ▷Outpatient Surgery PACU | 60.0 | 79% |
| ▷Inpatient Surgery PACU | -- | -- |
| ▷All Nurses All Divisions | 45.0 | 82.0% |
| ▽Physical Location - All Wards | 45.0 | 82.0% |
| ▷Ward A | 59.0 | 75.0% |
| ▽Ward B | 31.0 | 89.0% |
| ▷Ward B East | 36.0 | 88.0% |
| ▽Ward B West | 26.0 | 90.0% |
| ▷Room B-101W | 23.0 | 88.0% |
| ▷Room B-102W | 29.0 | 92.0% |

▨ <30m; >92%  ▩ 30-50m; 85-92%  ▧ >50 min; <85%

*Not all buckets are mutually exclusive

FIG. 48

SYSTEM, MEDICAL ITEM INCLUDING RFID CHIP, SERVER AND METHOD FOR CAPTURING MEDICAL DATA

CROSS-REFERENCE TO RELATED APPLICATIONS

The present application is a continuation-in-part of U.S. patent application Ser. No. 15/592,116 filed on May 10, 2017, which is a continuation of U.S. Parent application Ser. No. 15/390,695 filed on Dec. 26, 2016 now U.S. Pat. No. 9,679,108, which is a continuation of U.S. patent application Ser. No. 15/004,535 filed on Jan. 22, 2016 now U.S. Pat. No. 9,569,589, which claims the benefit of U.S. Provisional Patent Application No. 62/113,356 filed on Feb. 6, 2015, the contents all of which are incorporated herein by reference.

TECHNICAL FIELD

The technical filed generally relates to a system including a data collection engine, a plurality of medical items including radio-frequency identification chips, and a server.

BACKGROUND

A Radio-frequency Identification (RFID) chip can transmit information to a reader in response to an interrogation signal or polling request from the reader. The RFID chip can be incorporated in a tag (RFID tag) which is placed on a medical consumable item so that information can be passively captured. An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some medical consumable items may not be feasible do to financial considerations, weight, etc. On the other hand, placing a passive-type RFID tag on medical consumable items may be more feasible; however, a power source will be needed to passively obtain information. Therefore, a device that can provide power to the RFID tag on the medical consumable item as well as obtain the information from the RFID tag would be beneficial for activity based costing and to ensure proper charging.

During medical procedures such as surgery, it is very important to avoid errors such as retaining the medical consumable item in the patient after conclusion, performing surgery on the wrong section of the body, performing the wrong surgical procedure or even performing surgery on the wrong patient. Such errors are commonly referred to as "surgical never events". In order to avoid surgical never events, the position of a medical consumable item, a patient with respect to the medical consumable item, as well as the medical consumable items consumed are desirable information.

SUMMARY

According to various embodiments, the system includes a data collection engine (DCE), a plurality of RFID chips associated with a plurality of medical consumable items, and a server device. The RFID chip can be incorporated in a tag (RFID tag) which is placed on a medical item so that information can be passively captured. An RFID tag can be an active-type with its own power source, or a passive-type or battery-assisted passive type with no or limited power source. Instructions configure the server device controller to: create a neural network model (NNM) for modeling patient events; train and validate the NNM by supervised learning; calculate the outcome for new patient events based upon the trained NNM; classifying the output value as a risk category; and reassign resources to certain categories of the delays.

The instructions can also configure the controller to create a self-organizing map (SOM) network for modeling patient events, the SOM including a plurality of network nodes, a plurality of input nodes representing input attributes of the past patient events, wherein the plurality of network nodes is arranged in a grid or lattice in a fixed topological position, each of the plurality of input nodes is connected to all of the plurality of network nodes by a plurality of synaptic weights. The controller can generate an output value of the SOM network based upon input attributes for the clinical patient event, wherein the output value is a graphical display showing a particular category for the patient event.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIGS. 9A-9G illustrate an exemplary operating environment in which one or more DCEs receive medical data from RFID chips associated with medical consumables, medical professionals and a patient according to the first embodiment.

FIG. 13A is a perspective view of a donut headrest including a plurality of RFID chips according to the second embodiment.

FIG. 13B is a schematic view of a patient's head positioned within the donut headrest of FIG. 13A.

FIG. 13C is a diagram illustrating a top view of the operating table including the donut headrest according to the second embodiment.

FIG. 17 is a diagram illustrating a patient on an operating table including the skull clamp headrest of FIG. 15A and the endotracheal tube of FIG. 16A.

FIG. 18 is a diagram illustrating an adhesive eyelid occlusive dressing including an RFID chip according to the second embodiment.

FIG. 19 is a perspective view of a horse-shoe headrest including a plurality of RFID chips according to the second embodiment.

FIG. 28B is an illustration of an exemplary data set for patient attributes for various patient events.

FIGS. 29A-29B are illustrations of various exemplary approaches for normalizing the data set.

FIG. 30A-30B are illustrations of various exemplary approaches for encoding the normalized data set.

FIG. 43 is an illustration of iterative global error output when training a NNM.

FIG. 44 is an illustration of validation output when validating a trained NNM.

FIG. 46 is an illustration of exemplary regression tasks performed by the TMD.

FIG. 48 is an illustration of an exemplary system level discharge performance graphical display.

DETAILED DESCRIPTION

In overview, the present disclosure concerns a system which includes a Data Collection Engine (DCE), an RFID tag associated, for example, identifications of medical professionals and patients, backend devices such as one or more server devices and a throughput management device (TMD), and a plurality of client devices.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
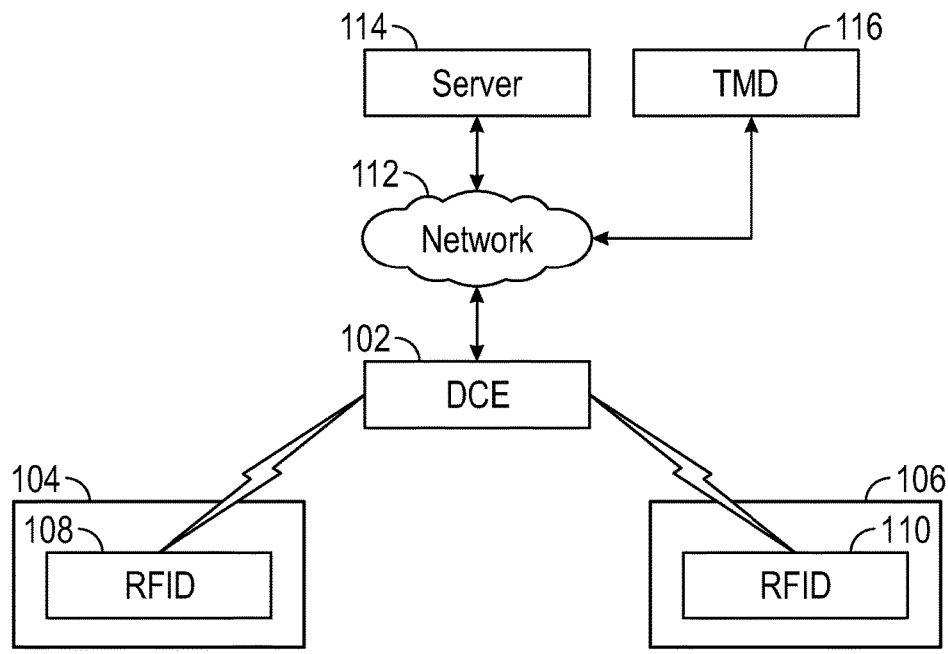
FIG. 1 illustrates an exemplary core operating environment in which a Data Collection Engine (DCE) receives medical data from RFID tags and transmits the medical data to a server via a connection to a network.
Figure 26A:
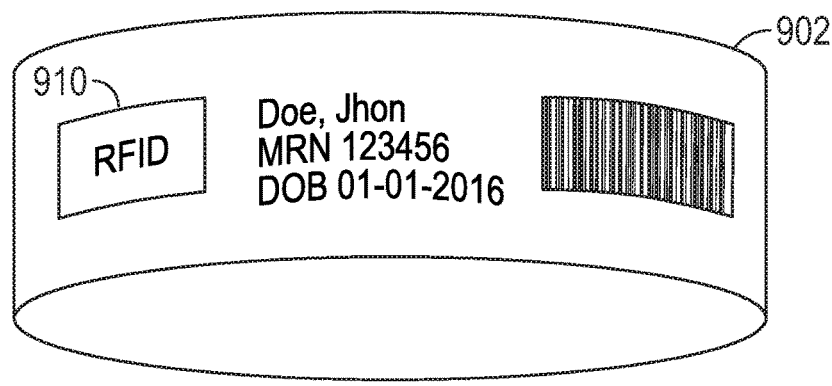
FIG. 26A is an illustration of a patient wrist band including an RFID tag.
Figure 26B:
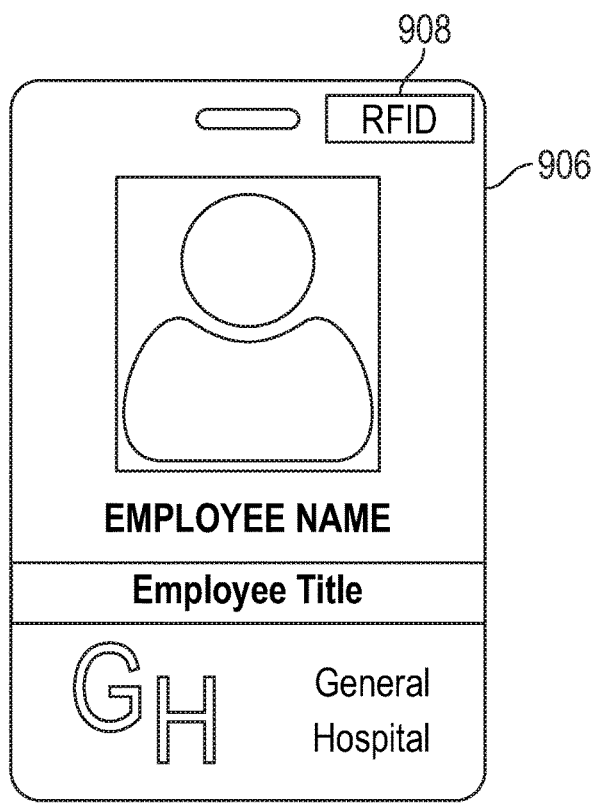
FIG. 26B is an illustration of a medical professional identification including an RFID tag.

Referring to FIG. 1, an exemplary operating environment in which the system according to various embodiments can be implemented will be discussed. The environment includes a DCE 102 communicating with first and second RFID tags 108, 110 which can be disposed in separate first and second rooms 104, 106. Each of the RFID tags 108, 110 is associated with a medical item such as a patient wrist band 902 (FIG. 26A) or doctor ID badge 906 (FIG. 26B). As discussed more fully below, the communication between the RFID tags 108, 110 and the DCE 102 is preferably wireless; however, wireline communication or a combination of wireless and wireline communication can also be used in some cases. The DCE 102, although shown here as a single entity, can include sub-portions in each of the rooms 104, 106. Moreover, as discussed later, the system likely includes many DCEs (see FIG. 23). The DCE 102 communicates with one or more server devices (represented generally by and referred to hereon as "server") 114 via a connection to a network 112 such as a local area network (LAN), wide area network (WAN), the Internet, etc. A TMD 116 can communicate with the server 114 and the DCE 102 via a connection to the network 112. The first and second rooms 104, 106 can be, for example, separate rooms of a hospital facility. The communication between the DCE 102 and the RFID tags 108, 110, between the DCE 102 and the server 114 or TMD 116, and/or between the server 114 and the TMD 116 can be encrypted or unencrypted. The network 112 can be, for example, a private LAN for the hospital facility. The server 114 can be a computing device local to the hospital facility. On the other hand, the network 112 can be the Internet, the DCE 102 can be local to the hospital facility and the server 114 can be one or more remote computing devices. One of ordinary skill in the art should appreciate that the server 114 can represent entities necessary for providing cloud computing such as infrastructure and service providers.

Figure 2:
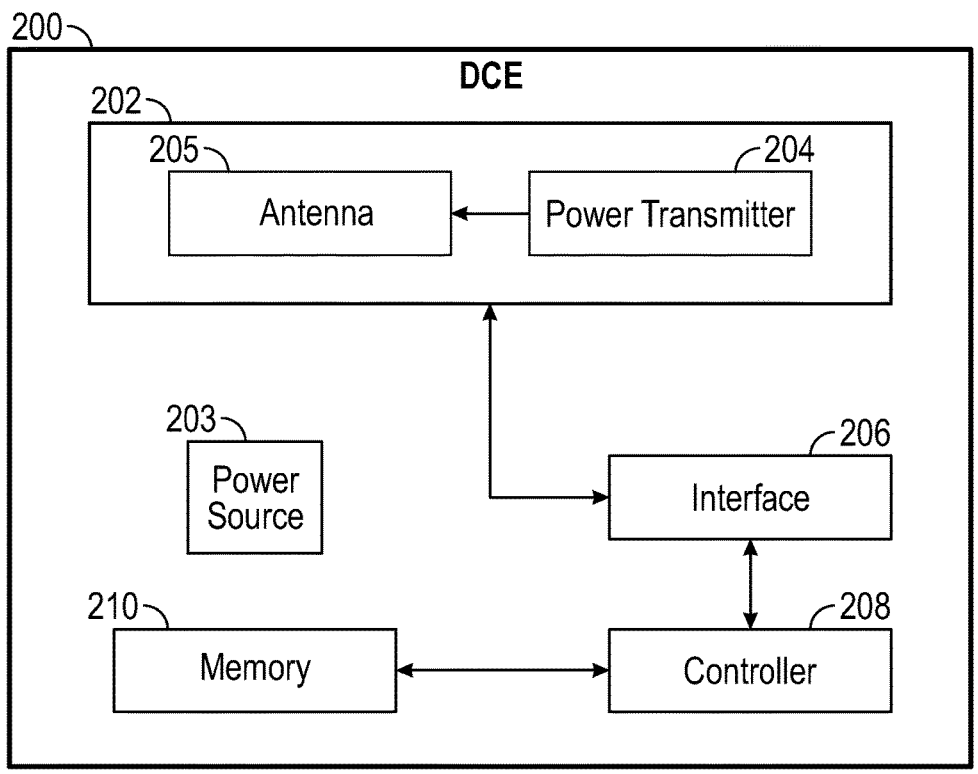
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of medical data and events received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3A:
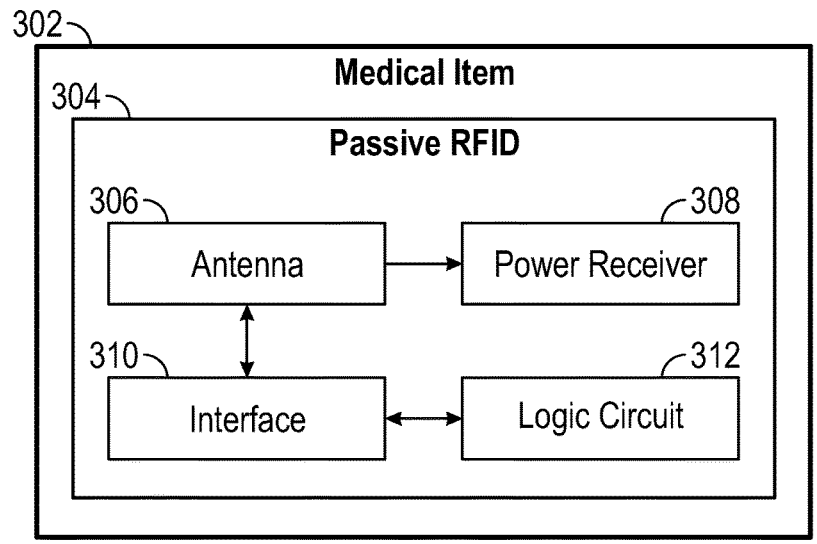
FIG. 3A is a block diagram illustrating exemplary portions of a passive-type RFID tag.

Referring to FIG. 3A, portions of an exemplary passive-type RFID tag 304 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates medical data such as an identification of the RFID tag and/or the medical item to which it is affixed, state, location, and changes in any data or properties thereof over time, all of which will be referred to as medical data. It should be noted that the medical data includes situational data which refers to a) the identity of the RFID tag, the identity reference for an individual, facility plant, property, equipment to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The medical data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the medical data received from the logic circuit 312 into an appropriate format for transmission. For example, the interface 310 can demodulate ASK signals or modulate data from the logic circuit 312 into ASK signals.

Figure 3B:
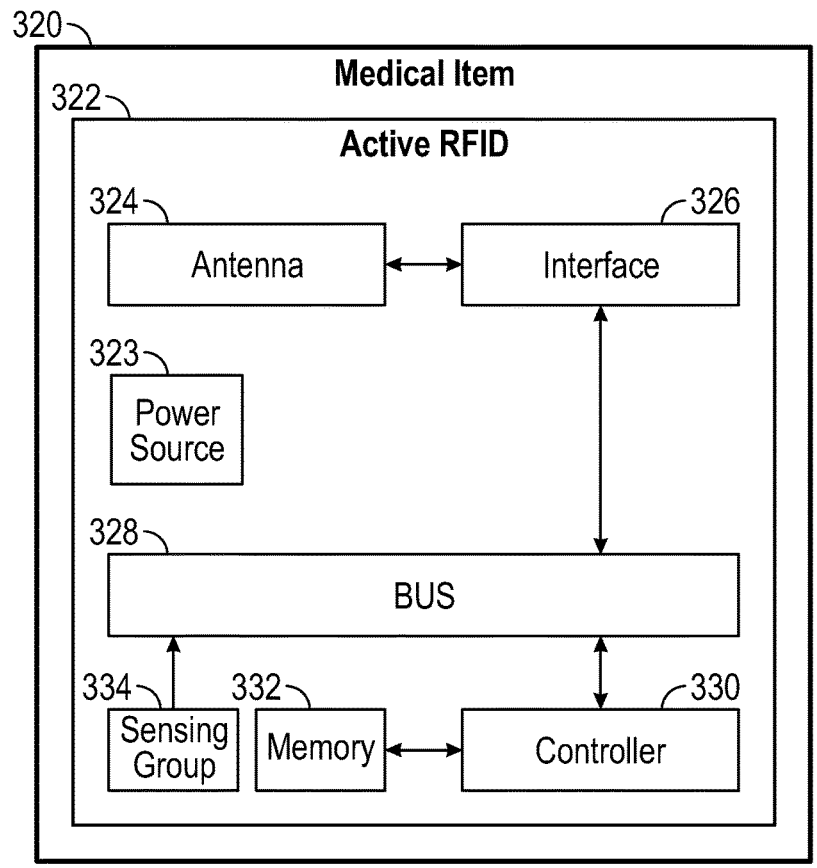
FIG. 3B is a block diagram illustrating exemplary portions of an active-type RFID tag.

Referring to FIG. 3B, circuit-level portions of the active-type RFID tag 322 on a medical item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the chip is within a predetermined distance from another RFID tag, a distance from one or more other RFID tags and/or the DCE, and/or distance and angle from a baseline orientation. The sensing group 334 can include a set of accelerometers for determining the acceleration value of the item 320, a digital compass that collects orientation information about the item 322, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass and/or the gyroscope, can facilitate motion detection. The sensing group 334 can include a separate OpenBeacon active tag or a Sense-a-Tag as described in "Proximity Detection with RFID: A Step Toward the Internet of Things" by Bolić et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another tag. Particularly, the controller 330 can be configured to send a registration message which includes identification data associated with the RFID tag 322 and thus the medical item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including medical data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference. As mentioned above, the DCE 102 can store data regarding its fixed location (i.e. room 106). In this case, the physical location of the RFID tag 110 can be determined via the DCE 102. Alternatively, the RFID tags can obtain position from some external reference (i.e. a device with GPS or via a device that provides an indoor positioning system location reference, or WiFi hotspots, that themselves have a known location, which can somehow transmit WiFi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 11:
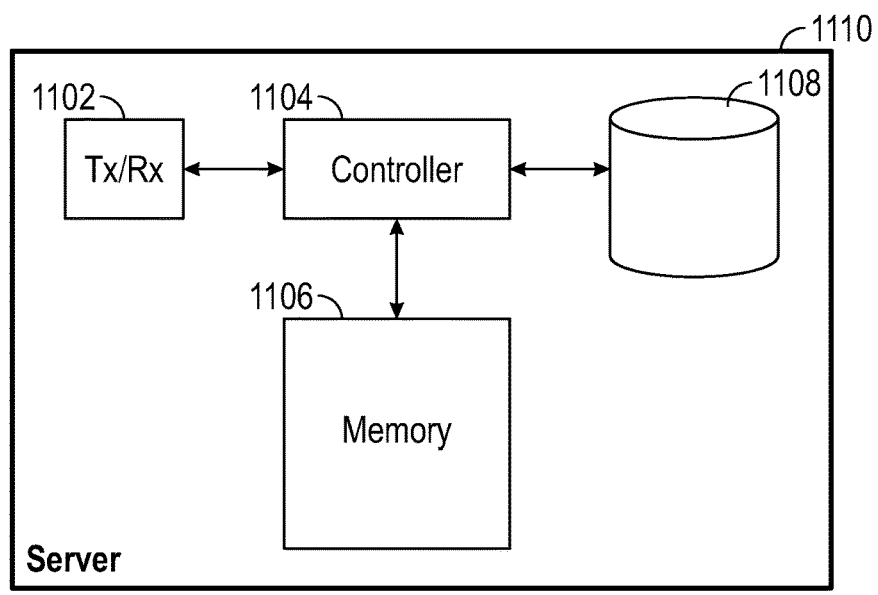
FIG. 11 is a block diagram illustrating exemplary portions of a server device according to various exemplary embodiments.

Referring to FIG. 11, the server device 1110 includes a transceiver 1102, a controller 1104, a first memory portion 1106, and one or more databases depicted generally by 1108. The databases 1108 can include a medical item database, a patient database, and a medical professional database. That database can be, for example, an atomic data store. The transceiver 1102 receives medical data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 1102 sends the information reply including the usage parameters associated with the one or more RFID chips to the client device. The transceiver 1102 can be similar to the transceiver of the DCE.

The memory 1106 can be one or a combination of a variety of types of memory such as RAM, ROM, flash memory, DRAM or the like. Alternatively, the database 1108 can be included in the memory 1106. The memory 1106 includes instructions for configuring the controller 1104.

Among the databases 1108, the medical item database stores a plurality of medical item identifications and usage attributes associated with each of the item identifications. The usage attributes can include an identification of a medical professional that used the medical item, an identification of a patient for whom the medical consumable item was used, a time duration for which the medical item was in a certain location, etc. The patient database can store patient identifications, attributes associated with each patient identification such as dispositions, scheduled surgeries, location history, consumed medical items, etc. The medical professional database can store medical professional identifications, attributes associated with each medical professional such as scheduled surgeries, location history, consumed medical items, etc.

The controller 1104 is configured according to the instructions in the memory 1106 to determine data in the database 1108 that is associated with the identification for each of the one or more RFID chips in the information request; generate the information reply including the usage parameters associated with the one or more RFID chips based upon the determined data; and store data in the message from the DCE in the medical item database to be associated with the identification of the first RFID chip.

The controller 1104 is further configured to determine based upon medical data and events included in messages received from the DCE, whether particular events of interest are likely to have occurred such as, whether a medical consumable item has been consumed or not, and store data related to the consumption of the medical consumable item in the database 1108. The controller 1104 is further configured to determine based upon the medical data and events, and attributes in the database 1108, whether a never event has or is about to occur, and generate a message to be sent in accordance with such determination.

The controller 1104 and database 1108 can be configured to perform command query responsibility segregation in which commands are separated from queries to allow scaling of servers that respond to queries separately from servers delegated to responding to messages. The controller 1104 and database 1108 can further be configured to use event sourcing and/or event streaming to ensure all changes to an application state get stored as a series of events which can be not only queried but reconstructed.

First Embodiment

Figure 4A:
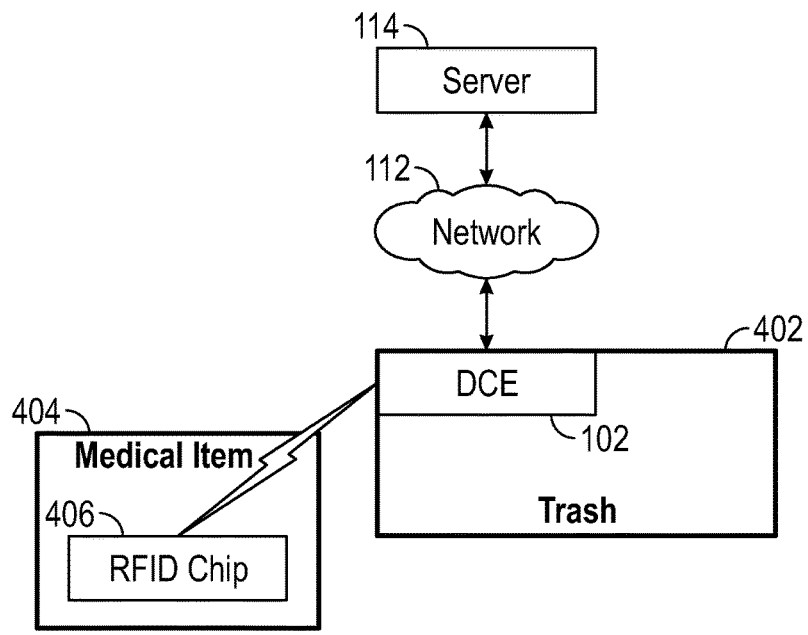
FIG. 4A-4B illustrate an exemplary operating environment in which one or more DCEs receive medical data from RFID chips associated with medical consumables, medical professionals and a patient according to a first embodiment.
Figure 4B:
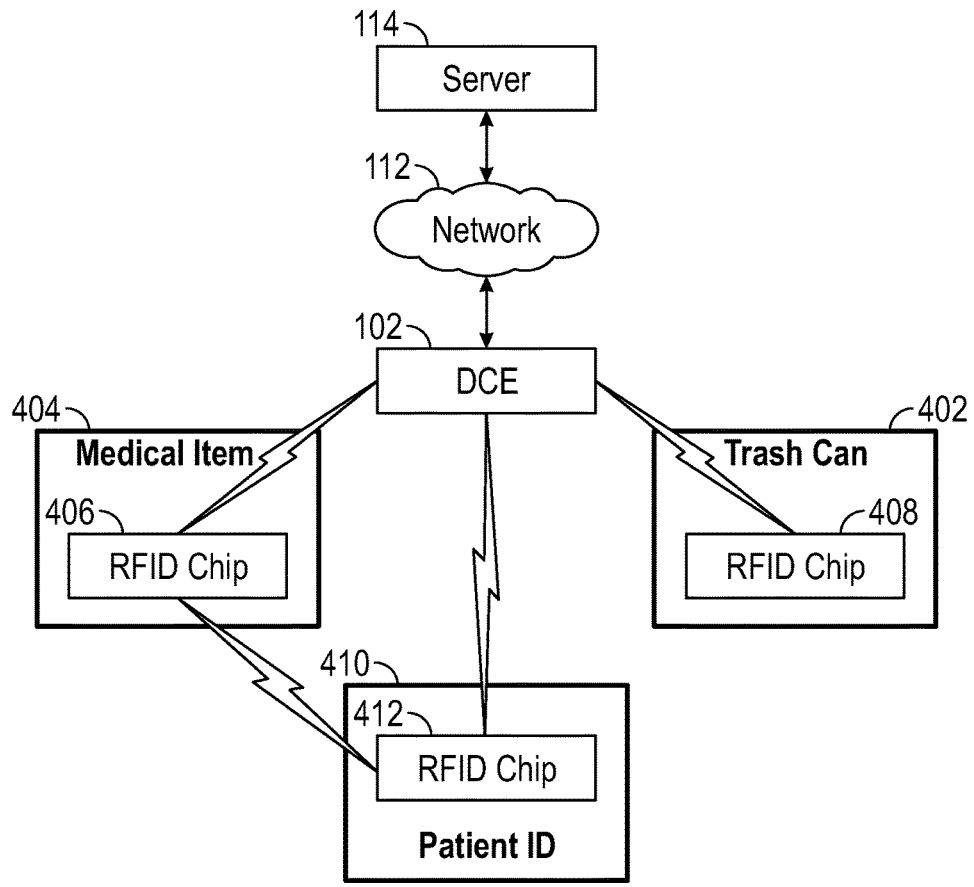

Referring to FIGS. 4A-4B, a first embodiment will be discussed by exemplary cases in which the DCE 102 receives medical data from one or more RFID chips. In the case shown in FIG. 4A, the DCE 102 is disposed on a trash receptacle 402. A medical consumable item 404 including a first RFID chip 406 (passive or active) is placed in the trash receptacle 402. The DCE 102 establishes communication with the RFID chip 406. Particularly, the DCE 102 can periodically generate a broadcast message, and receive a registration message and medical data from the RFID chip 406 indicative of a medical event in reply to the broadcast message. Alternatively, the RFID chips can self-initiate sending of the registration message periodically or in response to another external trigger If the RFID chip 406 is passive type, it can send the medical data while receiving power from the DCE 102. The registration message can include identification information associated with the RFID chip 406. In this case, the medical event would be use of the medical consumable item 404 (indicated by being in the trash receptacle 402). The DCE 102 can send a message indicative of the first medical event to be sent by the transceiver to the server device 114 via a connection to the network 112.

In the case shown in FIG. 4B, the DCE 102 is disposed not in the trash receptacle 402, but in a position such as the ceiling beneficial for establishing wireless communication coverage for a room. The DCE 102 receives medical data from the first RFID chip 406 affixed to the medical consumable item 404, a second RFID chip 408 (passive or active-type) affixed to the trash receptacle 402, and a third RFID chip 412 (passive or active-type) affixed to a patient identification 410 such as a wristband. The DCE 102 establishes communication with each of the RFID chips 406, 408, 412 by, for example, generating a general broadcast message, and receiving registration messages in reply to the broadcast message, and medical data from the RFID chips indicative of medical events. Particularly, the RFID chip 412 sends a message including medical data indicative of a first medical event, which would be the RFID chip 406 of the medical consumable item 404 being within predetermined distance from the RFID chip 412 associated with the patient identification 410. As noted above, the RFID chip (active-type or passive-type) can include a sensor for detecting near presence of another RFID chip. The RFID chip 408 sends a message including medical data indicative of a second medical event, which would be the medical consumable item 404 being within predetermined distance from the RFID chip 408 associated with the trash receptacle 402 for more than a predetermined time duration. The RFID chip 406 sends a message including medical data indicative of the chip identification. The DCE 102 can send one or more messages indicative of the medical events to be sent to the server device 114 via the network connection.

Figure 5:
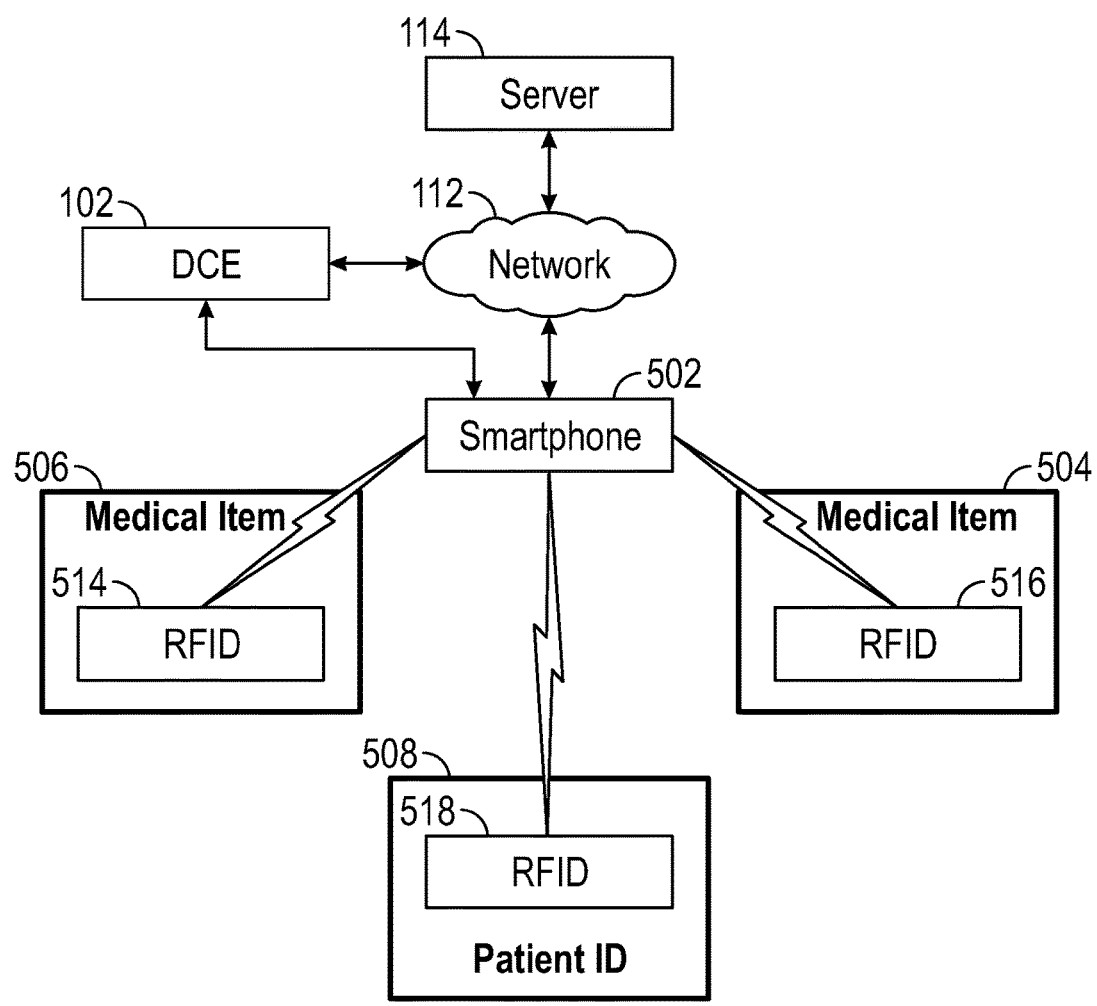
FIG. 5 illustrates an exemplary operating environment in which a smartphone acts as a DCE to receive medical data from RFID chips associated with medical consumable items, medical professionals and a patient according to a modification to the first embodiment.

Referring to FIG. 5, exemplary modification to the first embodiment will be discussed by an exemplary operating environment in which a smartphone 502 communicates with the RFID chips. The smartphone 502 generates a broadcast message, and receives messages indicative of medical events from the RFID chips 514, 516, 518 associated with medical items 506, 504, 508. The messages include registrations messages and medical data indicative of a first, second and third medical events in reply to the broadcast message. The smartphone 502 can then send this data to the DCE 102 directly or via the network 112 or even directly to the server 114. For example, in a large facility such as a hospital, there may be areas in which there is no or very poor wireless coverage from the DCE 102. In these cases, a mobile device such as the smartphone 502 can be used to obtain medical data from chips in such areas and transmit the medical data to the DCE 102. Similar to the discussion of FIGS. 4A-4B, the events can be the RFID chips being within a predetermined distance of each other.

The smartphone 502 and/or the DCE 102 can be configured to locally persist and send the medical data to the server 114 either immediately upon collecting data or at a subsequent time after a batch of one or more pieces of data has been collected. The smartphone 502 and/or DCE 102 can purge the data sent from volatile or persistent memory immediately after successfully sending it or at a later time, either automatically or when prompted.

Figure 8:
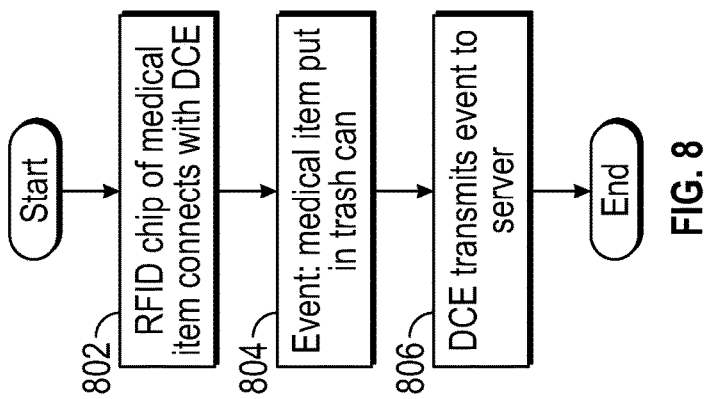
FIG. 6-8 are flow diagrams illustrating exemplary operations of the DCE and RFID chips associated with medical consumable items, medical professionals and a patient according to the first embodiment.
Figure 7:
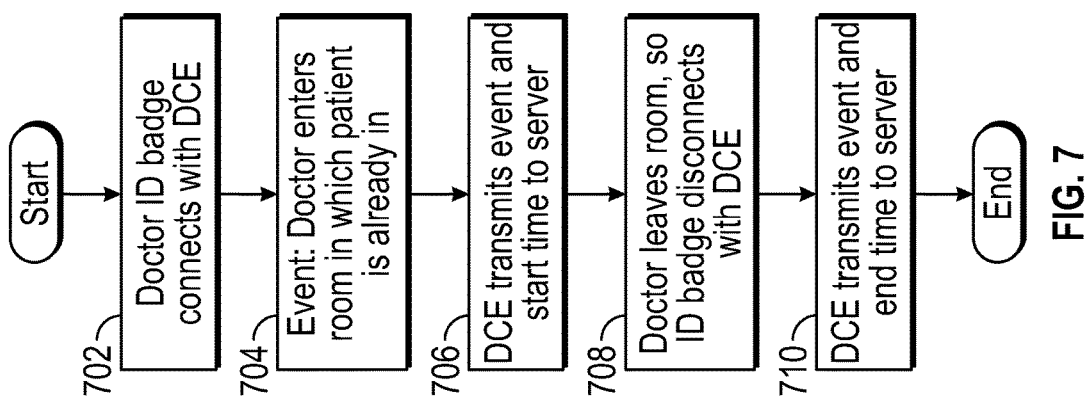
Figure 6:
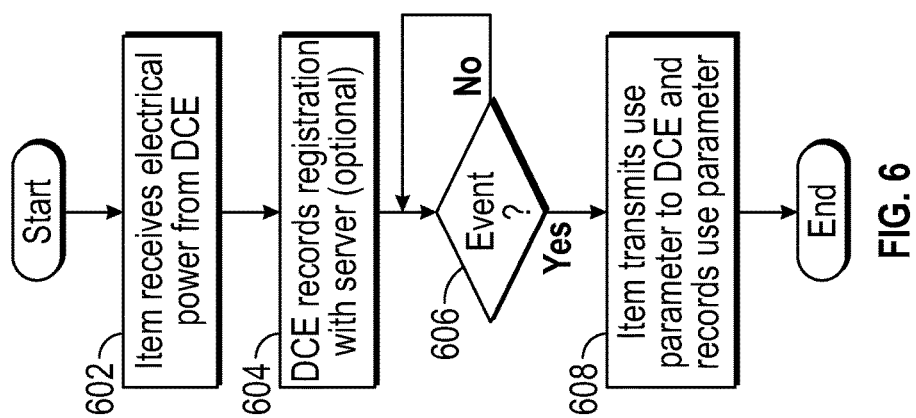

FIGS. 6-8 are flow diagrams illustrating exemplary operations of the DCE and RFID chips associated with medical items, medical professionals and a patient according to the first embodiment.

Referring to FIG. 6, the operations of the RFID chip and the DCE in a simple scenario will be discussed. At 602 a passive-type RFID chip receives electrical power wirelessly from the DCE. The wireless power can be sent along with a regular general broadcast message from the DCE or an interrogation request. Of course if the RFID chip is active-type, this step can be omitted. At 604, the RFID chip sends registration information to the DCE, which records it in its memory. Particularly, the registration information can include the identification of the RFID chip. At 606, if the RFID chip and/or the DCE determines that an event has occurred, at 608 the RFID chip sends use parameters associated with the event to the DCE. The DCE records the usage parameters in its own memory or immediately transmits the information to the server to be stored in the medical item database. The event can be, for example, detecting that the RFID chip is within predetermined distance from another RFID chip associated with, for example, the trash receptacle for more than a predetermined time duration as discussed in FIGS. 4A-4B.

Referring to FIG. 7, the operations of the RFID chip and the DCE in a more complex scenario in which a medical professional such as a doctor meets with a patient will be discussed. At 702, the doctor wearing an identification such as a badge including an RFID chip (active or passive-type) enters a room within the communication area of the DCE and the RFID chip registers with the DCE. A patient with a patient identification including another RFID chip which has already registered with the DCE is already in the room. At 704, the DCE records a first medical event indicative of the patient and the doctor being in the same room and the start time. At 706, the DCE generates a message representative of this first medical event to be transmitted to the server. At 708, the doctor wearing the identification including the RFID chip leaves the room, and disconnects from the DCE. At 710, the DCE records the time the RFID chips disconnects as the end time of the first medical event, and generates a message representative of the end time of the first medical event to be transmitted to the server.

Referring to FIG. 8, the operations of the RFID chip and the DCE in the scenario shown in FIG. 4A will be discussed. At 802, the RFID chip associated with the medical consumable item connects with the DCE in the trash receptacle. At 804, the DCE records a medical event indicative of the medical consumable item being in the trash receptacle. At 806, the DCE generates a message representative of this medical event to be transmitted to the server.

Figure 9A:
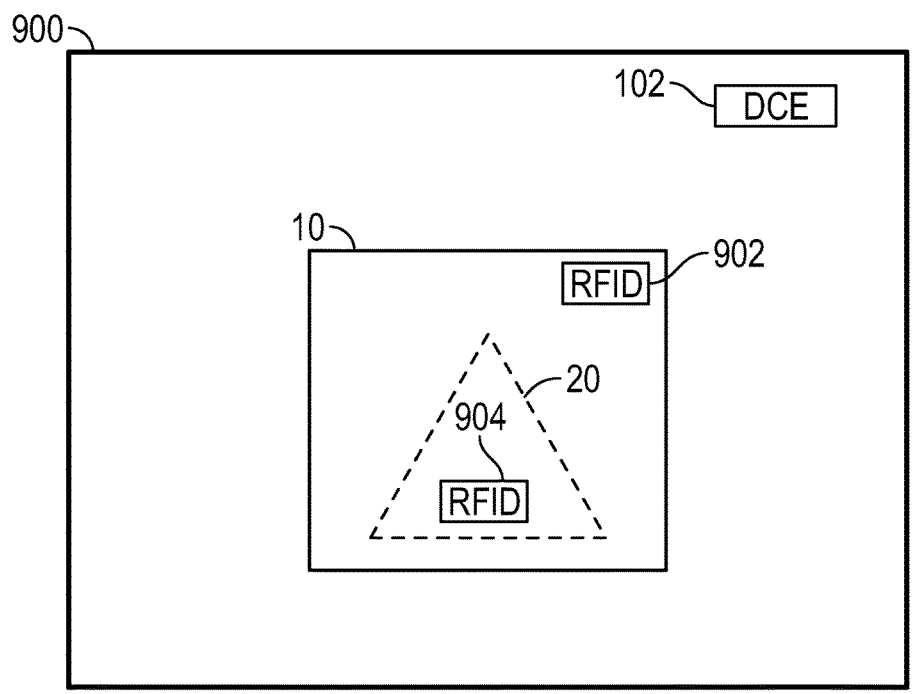

Referring to the flow diagram of FIG. 10 and the diagrams of FIGS. 9A-9G, operation of the DCE 102 and the server according to the first embodiment will be discussed. In FIG. 9A, the DCE 102 establishes a wireless communication coverage area depicted generally by room 900. A package 10 including a medical consumable item 20 is in the room 900. A first RFID chip 902 is disposed on the package 10 and a second RFID chip 904 is disposed on the medical consumable item 20 in the package.

Figure 9B:
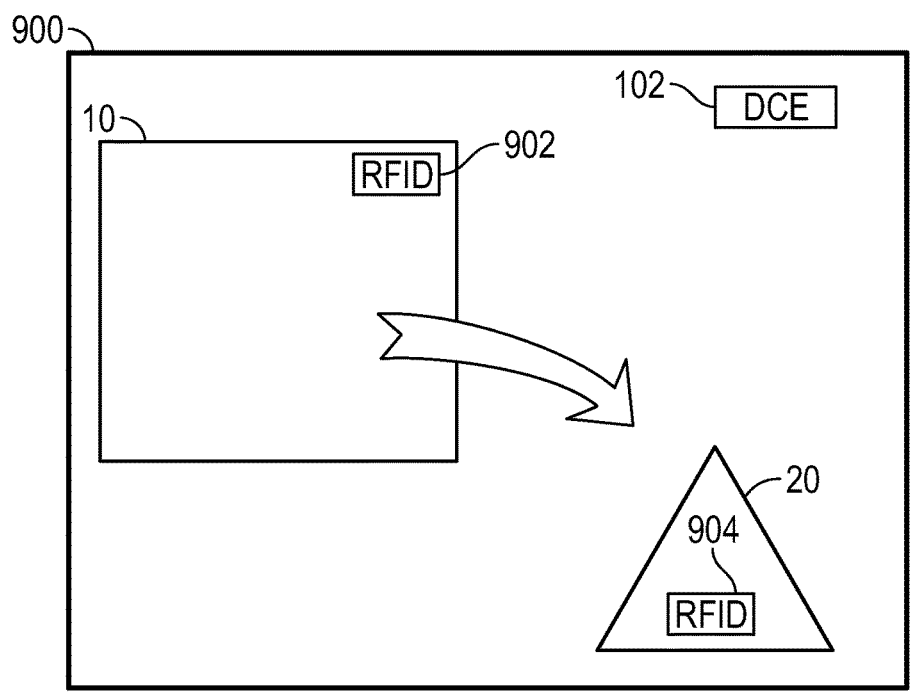
Figure 10:
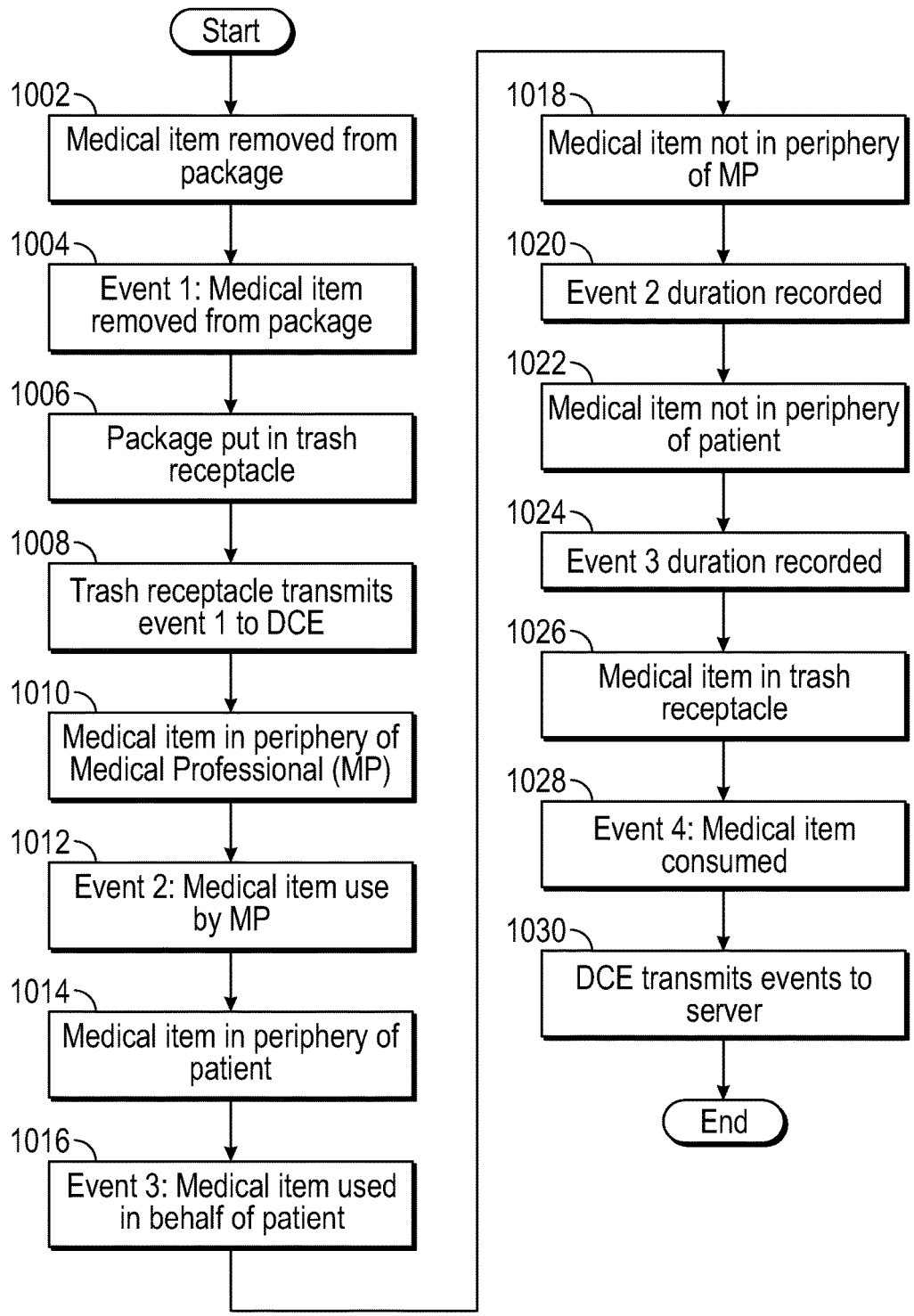
FIG. 10 is a flow diagram illustrating exemplary operations of the RFID chips in medical consumable items and the DCE according to the exemplary operating environment shown in FIGS. 9A-9G.

At 1002, the medical consumable item 20 is removed from the package 10 as shown in FIG. 9B. At 1004, one or both of the RFID chips 902, 904 detects the separation and sends a message to the DCE 102 including a medical event indicative of the separation of the item 20 from the package 10.

Figure 9C:
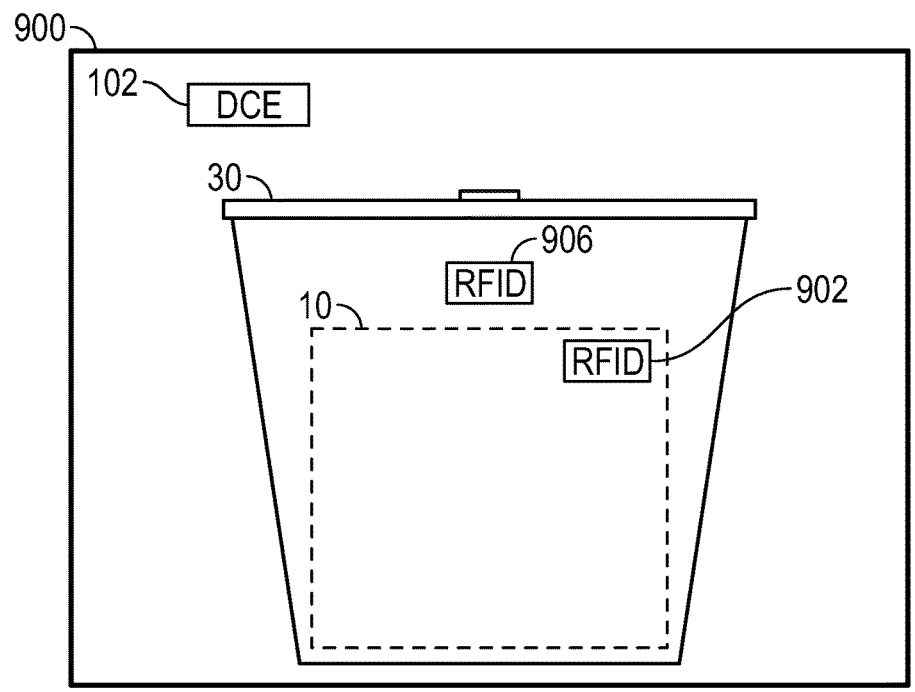

At 1006, the packaging 10 is placed in a trash receptacle 30 including a third RFID chip 906 as shown in FIG. 9C. At 1008, the third RFID chip 906 detects that the packaging 10 is in the receptacle 30 and sends a message to the DCE 102 including a medical event indicative of the packaging 10 being in the receptacle 30.

Figure 9D:
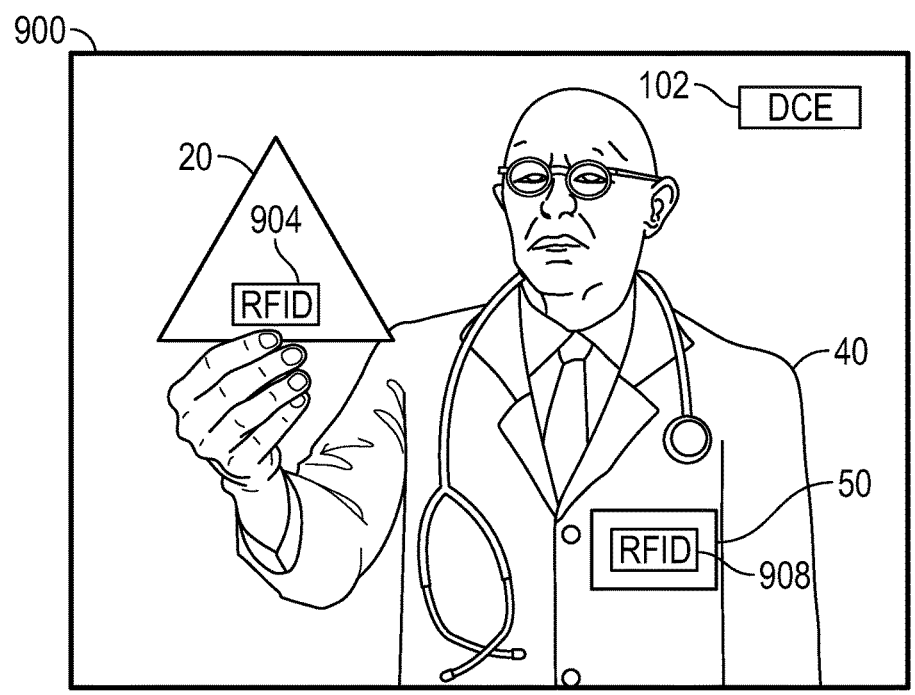

At 1010, a doctor 40 or other medical professional wearing a doctor identification or badge including a fourth RFID chip 908 has entered the room 900 as shown in FIG. 9D. The DCE 102 receives a registration message from the fourth RFID chip 908 when it enters the room. The doctor 40 holds the medical consumable item 20. At 1012, one or both of the RFID chips 904, 908 detects that the item 20 is less than a predetermined distance from the identification card 50, and sends a message to the DCE 102 including a medical event indicative of the item 20 being used by the doctor 50.

Figure 9E:
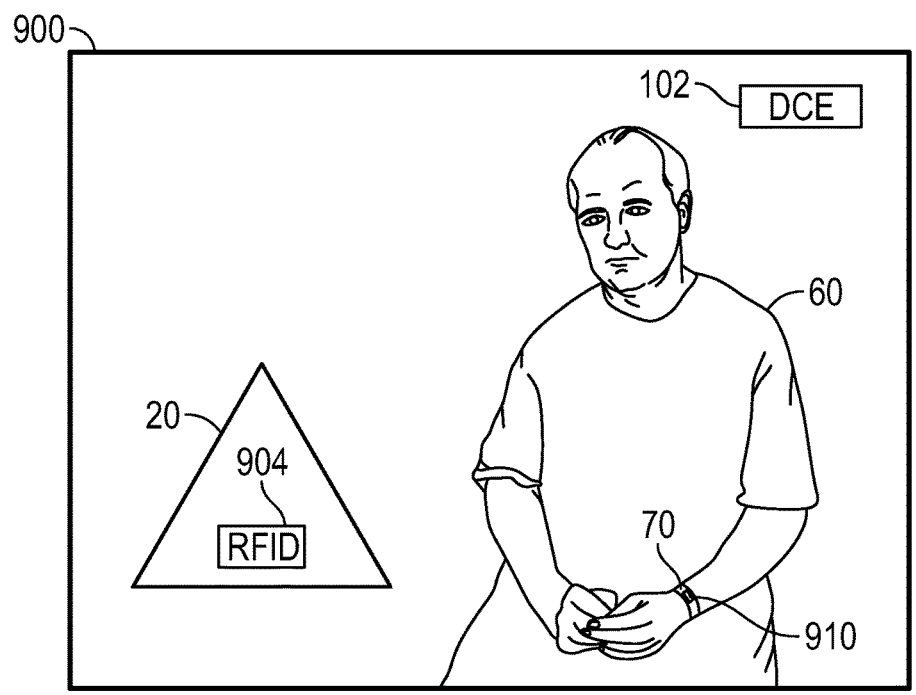

At 1014, a patient 60 wearing a patient identification or badge 70 including a fifth RFID chip 910 is in the room 900 as shown in FIG. 9E. The DCE 102 can receive a registration message from the fifth RFID chip 910 when it enters the room 900. The doctor, for example, holds the medical consumable item 20 near the patient 60. At 1016, one or both of the RFID chips 904, 910 detects that the item 20 is less than a predetermined distance from the patient identification card 70, and sends a message to the DCE 102 including a medical event indicative of the item 20 being used for the patient 60.

At 1018, when the medical professional 40 is more than a predetermined distance from the item 20 (or not within a periphery of near field detection), at 1020 one or both of the RFID chips 904, 908 detects that the item 20 is less than a predetermined distance from the medical professional identification card 50, and sends a message to the DCE 102 including a medical event indicative of the item 20 no longer being used by the medical professional 40 and the time duration for which the item was used.

At 1022, when the patient 60 is more than a predetermined distance from the item 20 (or not within a periphery of near field detection), at 1024 one or both of the RFID chips 904, 910 detects that the item 20 is less than a predetermined distance from the patient identification card 70, and sends a message to the DCE 102 including a medical event indicative of the item 20 no longer being used for the patient 60 and the time duration for which the item was used for the patient.

Figure 9F:
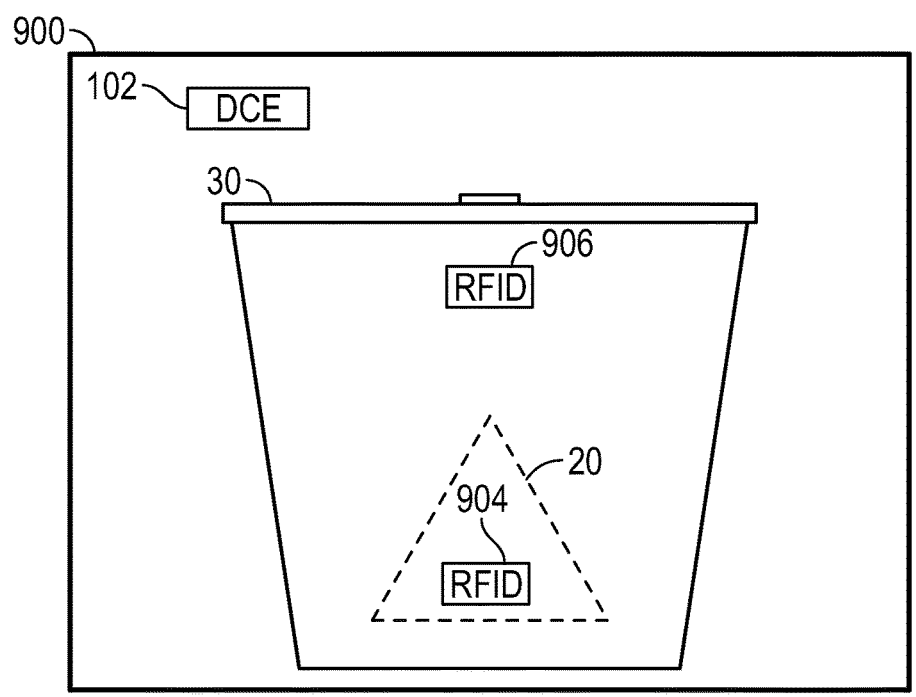

At 1026, the medical consumable item 20 is placed in a trash receptacle 30 including the third RFID chip 906 as shown in FIG. 9F. At this time, one or both of the RFID chips 904, 906 detects that the item 20 is in the receptacle 30 and sends a message to the DCE 102 including a medical event indicative of the item 20 being in the receptacle 30.

Referring to FIG. 9G, an exemplary conceptual message 920 generated by the DCE 120 (shown in human readable format) to be sent to the server is shown. The message 920 includes the series of events related to the medical consumable items discussed above. The time data can be determined by when the message from the RFID chip was received by the DCE or when it was sent to the server, or may be included in the message from the RFID chip. The location data can be generally the location of the DCE 120 and/or the RFID chip. The server device 1110 can store the data included in the message 920 in the database 1108 in the format depicted by 940. Particularly, information parameters can be stored according to an identification reference mapped to a given medical consumable item identity and/or any other entity identity referenced in a given message containing medical and/or situational data. Examples of such entity identity references include the actual product type or unique product identity associated with a given RFID chip identity, any medical professional (RFID chip identity associated with a medical professional) that may have been registered in proximity to an RFID chip with an identity that references a given item, any patient (RFID chip identity associated with a patient) that may have been registered in proximity to an RFID chip with an identity that references a given item, a room or trash receptacle referenced by a given DCE identity or RFID chip identity, etc.

The RFID chips can detect separation from another RFID chip or being within a predetermined distance from another RFID chip by the sensor group. Alternatively, the detection can be performed by ambient radio frequency communication techniques which can detect proximity up to, for example, 70 cm by backscattering. Further, the detection can be performed at the DCE end by, for example, measuring the RSS of the RF signal received from the chips.

Second Embodiment

A second embodiment of the system will be discussed by exemplary cases in which parameters such as a position signature of one or more medical items is determined based upon medical data from the RFID chips.

Figure 12A:
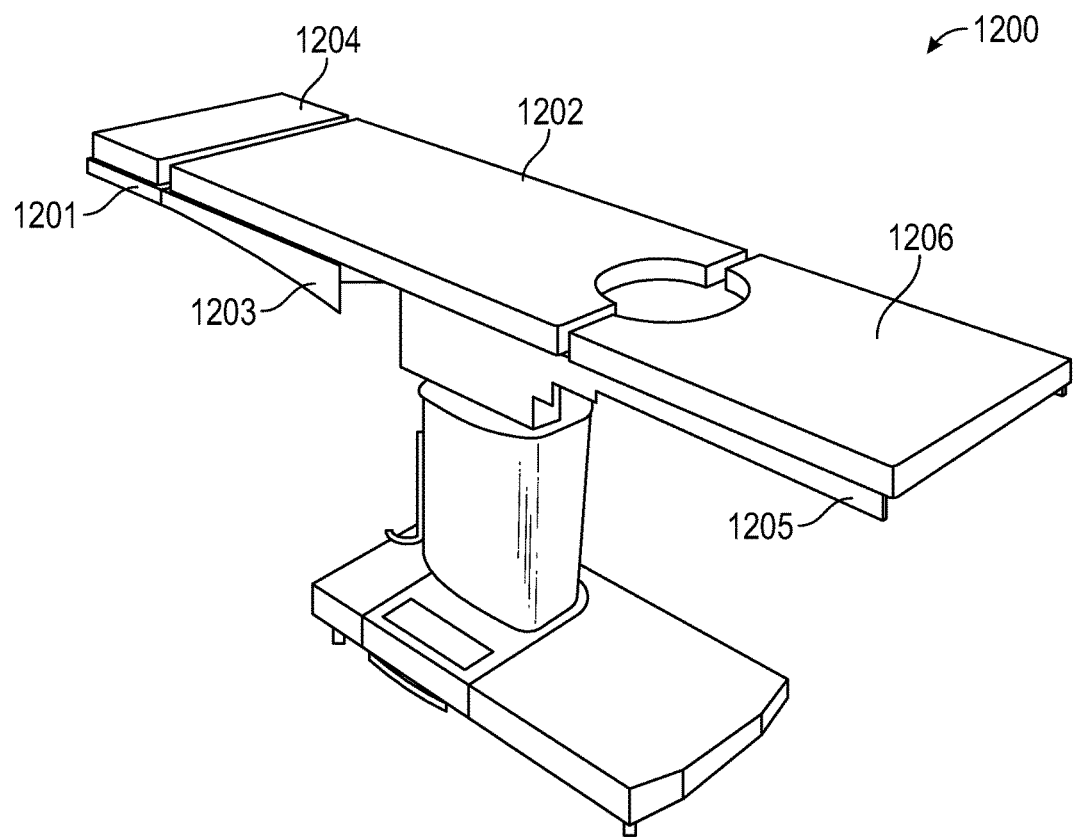
FIG. 12A is a perspective view of an operating table including a plurality of RFID chips according to an exemplary second embodiment.
Figure 12B:
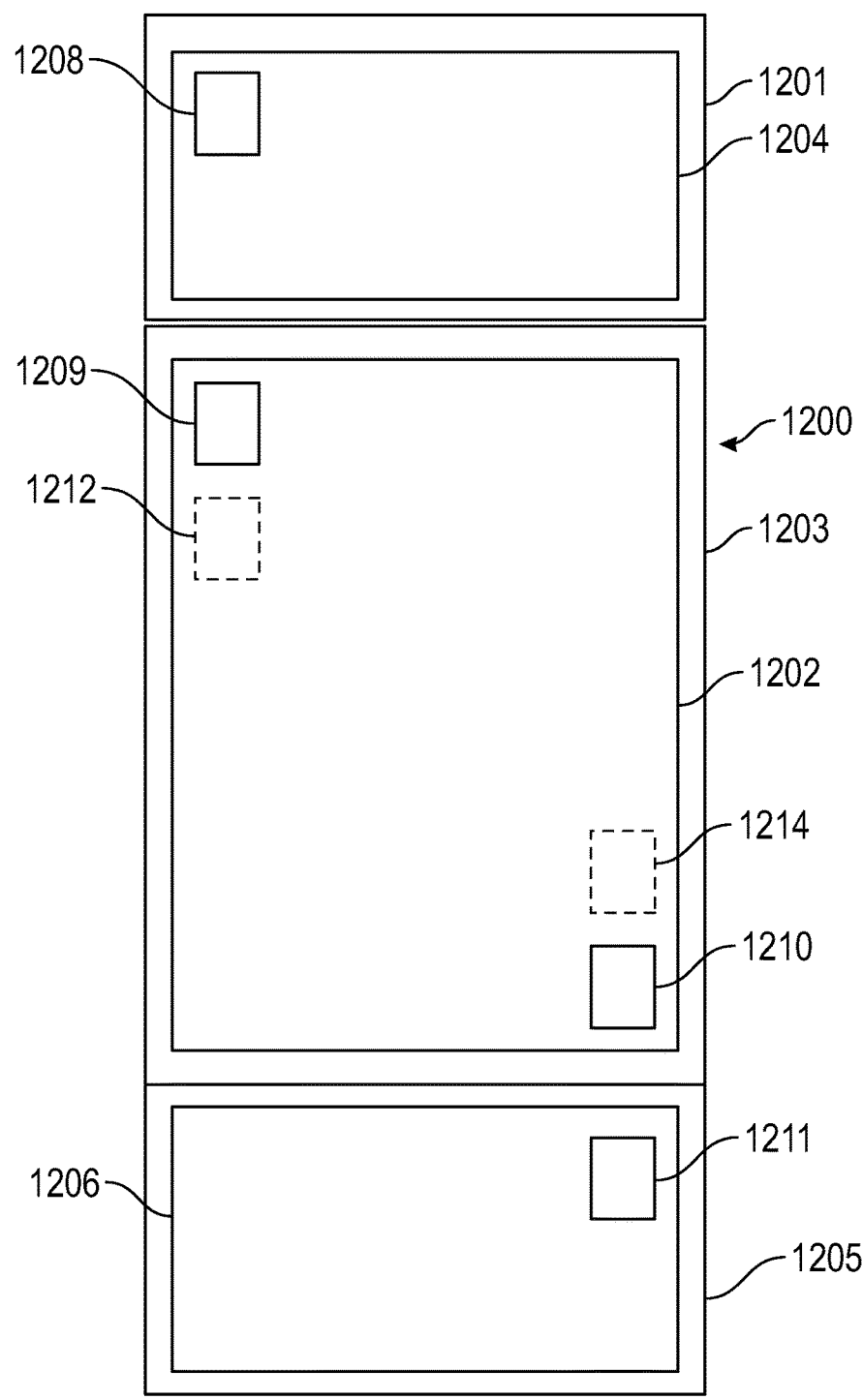
FIG. 12B is a diagram illustrating a top view of the operating table of FIG. 12A.

Referring to FIGS. 12A-12B, the medical item is a patient operating table 1200 and one or more of the RFID chips discussed above with respect to FIGS. 3A-3B are affixed to the table 1200. The operating table 1200 includes a foot cushion portion 1204 disposed on a foot portion frame 1201, a center cushion portion 1202 disposed on a center portion frame 1203, and a head cushion portion 1206 disposed on a head portion frame 1205. The foot cushion portion 1204 includes RFID chip 1208. The center cushion portion 1202 includes RFID chips 1209, 1210. The head cushion portion 1206 includes RFID chip 1211. The center portion frame 1203 includes RFID chips 1212, 1214. Preferably, at least one of the RFID chips 1209 and 1212 and the RFID chip 1210 and 1214 near edge of the center portion frame 1203 and cushion portion 1204 is an active-type RFID chip which includes or is electrically coupled to one or more or a network of pressure sensors.

Near field communication (NFC) between, for example, RFID chips 1209 and 1208, and between, for example, RFID chips 1210 and 1211 can be used to ascertain situational knowledge about the operating table configuration. Namely, whether the head of bed is connected (for example, whether the respective RFID chips are within a predetermined range of distance) to the center portion of the bed or not. Similarly, the presence or absence of the foot portion of the operating table can be determined from chips 1209 and 1208, for example. Information regarding the relative positon and inter-chip distance between chips 1209 and 1212 and 1210 and 1214, for example, can be used to determine whether the cushion for the center portion of the operating table is in present and in place. Particularly, one or both of RFID chips 1209 and 1208 send registration data including the chip identification to the DCE, and sends a message including medical data indicating that it has established NFC with the other chip and the identification of the other chip. Similarly, one or both of RFID chips 1210 and 1211 send registration data including the chip identification to the DCE, and sends a message including medical data indicating that it has established NFC with the other chip and the identification of the other chip. The DCE sends messages including this medical data to the server device. The server device can determine whether the foot and head of bed sections are attached to the center portion of the operating table and from the identity of the chips and each chip's known reference to specific portions of the operating table, and which end is the foot of the bed based upon the medical data. Particularly, when both of RFID chips 1209 and 1208 have established NFC with each other, and both of RFID chips 1210 and 1211 have established NFC with each other, the location and relative positions of the head foot and center portions of the patient operating table 1200 can be determined.

Referring to FIGS. 13A-13B, a donut-type headrest 1301 (referred to here as donut) can be used on the patient operating table for patient head positioning. First and second RFID chips 1302 and 1304 affixed to the donut 1301 include pressure sensors and/or communicate with pressure sensors in the donut 1301. For example, imbedded just beneath the surface of the donut are a plurality of pressure sensors situated in a known configuration, at a known distance apart and in relation to each other to permit the measurement of the pressure, pressure gradient, and pressure distribution along the surface of the donut. A patient's head may be oriented in a large variety of ways on the donut 1301. Any particular position will result in a specific pressure distribution, herein called a position signature which can be detected by the RFID chips 1302 and 1304, and transmitted to the DCE along with a date and time stamp and other data collection related metadata. For example, as shown in FIG. 13B, the RFID chips 1302 and 1304 can detect the pressure distribution resulting from the weight of the patient's head and neck as transmitted to the donut at points of contact with the patient's neck, chin, ears, and any portion of the patient's face and scalp that comes into contact with the donut 1301. This data can be transmitted from the RFID chips 1302 and 1304 to the DCE along with a date and time and other data collection related metadata. The DCE or server device can determine the patient's head position based upon this data utilizing algorithms developed from machine learning techniques discussed later.

Referring to FIG. 13C, the donut 1301 can be used together with the operating table 1306. The operating table 1306 includes first and second RFID chips 1308, 1310 on the cushion portion and RFID chips 1312, 1314 on the frame portion. When the donut 1301 is initially placed on the operating table, it is not known whether the donut 1301 is on the foot of the table or the head of the table. In the present embodiment, inter-RFID chip distances d1, d2, d3, d4, d5, d6, d7 and d8 are determined. For example, chips 1310, 1314 measure the distances d1, d2 to the chip 1302 on the donut 1301. RFID chips 1308, 1312 measure the distances d3, d4 to the chip 1302 on the donut 1301. Further, chip 1308 measures the distance d6 to tag 1304. Chip 1308 (or DCE) previously stores distances d5, d7. Further, chips 1302, 1304 can measure the distance d8 or the distance d8 can be previously stored. The distances can be measured by, for example, measuring an RSS of signals returned from other tags. Alternatively, one or more Sense-a-Tags (STs) can be included in the RFID tags or deployed separately. The inter-RFID distances are included in medical data sent from the RFID tags to the DCE, and are used to determine the relative positions of the donut 1301 and the table 1306, and thus where on the table 1306 the donut 1301 is located.

Figure 14A:
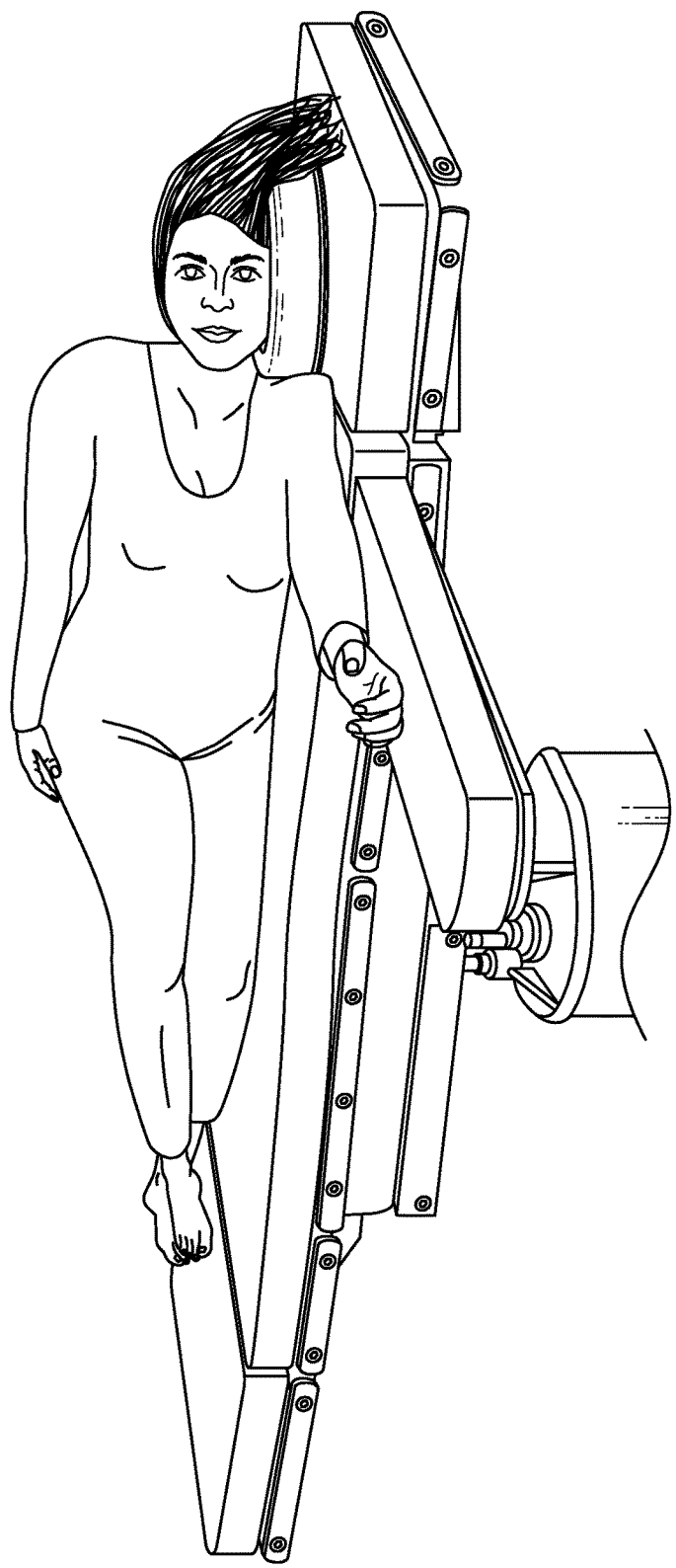
FIG. 14A is a perspective view of a patient positioned on her left shoulder on the operating table.
Figure 14B:
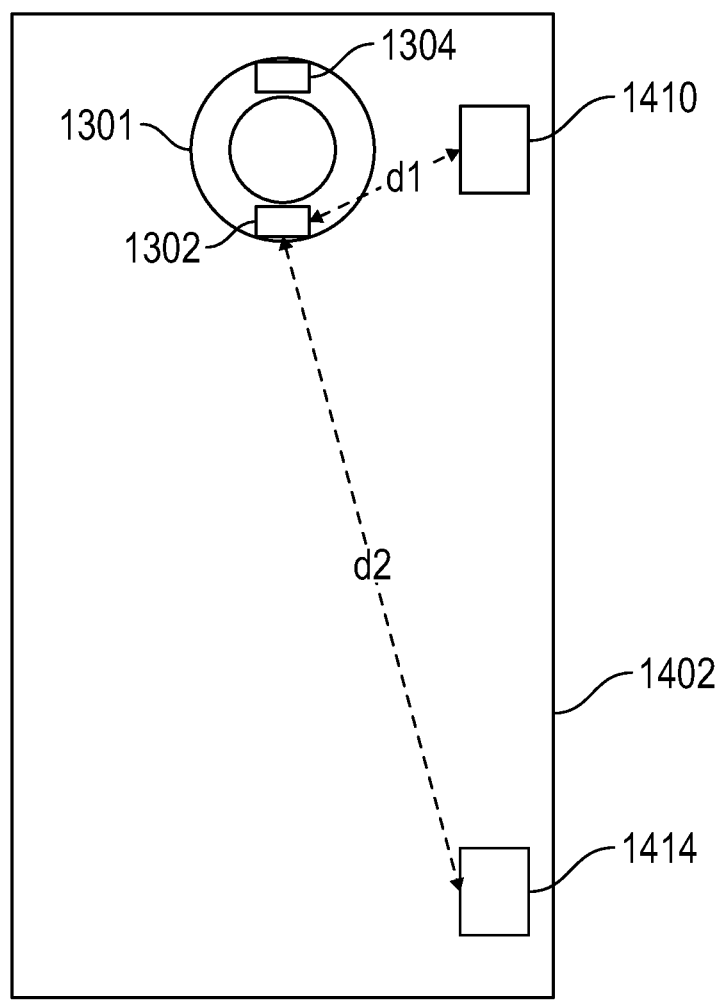
FIG. 14B is a block diagram illustrating the position signatures detected and communicated by the RFID chips on the donut headrest and the operating table according to the second embodiment.

Referring to FIG. 14A-14B, the data obtained from RFID chips on the operating table 1402 and the donut 1301 can be used to determine the position of the patient on the operating table 1402. FIG. 14B shows the data obtained from the RFID chips 1410, 1414 on the operating table 1402 (the patient's position signature) when the patient is positioned on the table as shown in FIG. 14A. The distance d1 between RFID chip 1410 and RFID chip 1302 (or RFID chip 1304) is shorter than the distance d2 between RFID chip 1414 and RFID chip 1302 (or RFID chip 1302). Thus, this data can be used to determine that the patient head location relative to the operating table. For example, if RFID chip 1410 is affixed to the frame or cushion of the head of the bed portion of the operating table, the information can be used to infer the patient's head is resting on the head portion of the operating table. However, if RFID chip 1410 is affixed to the frame or cushion of the foot portion of the operating table, the information can be used to infer that the patient's head is resting on the foot portion of the operating table, in a reverse orientation (relative to the names of the operating table foot and head portions). Further, RFID chips 1410, 1414 can detect pressure distribution of the patient's weight on the surface of the operating table and communicate this data or position signature along with a date and time stamp, and other data collection related metadata to the DCE. The pressure data can be used to determine, in this case, that the patient is on her left side. This pressure distribution data or position signature is obtained from pressure sensors within the operating table cushions or within a pad, for example a gel mat, placed on top of the operating table across one or more segments of the table. This network of a plurality of pressure sensors are situated in a known configuration at a known distance apart and in relation to one another and are employed to collect pressure distribution data which is then communicated to an imbedded or non-imbedded RFID chip either via wired connection or near field communication. The RFID chip(s) can be interrogated or can self-initiate communication with the DCE and communicate the RFID chip and pressure sensor pad identity along with the pressure data, location, and time of pressure data collection in addition to other data collection related meta data. Data can be collected at a variety of time intervals and be used to determine the change in the patient's position over time. For example, through the various phases of an operation, from the time the patient is first transferred to the operating, intubated, positioned for the procedure, extubated and transferred from the operating table. The timestamps and position signatures obtained at different intervals can be used to determine, independently or in combination with other data, such as the type of case scheduled to be taking place in a particular location at a particular time to give one example, the phase of the operation that the patient is in at any given time and to predict the probability that the operation is or is not proceeding as intended, among other things. For example, if the patient's position at a particular phase of the operation is not as expected, such as the patient being positioned prone instead of supine as scheduled or on the left side instead of the right side as scheduled, etc. These predictions are made by the DCE or server utilizing algorithms derived from machine learning techniques mentioned above and discussed more fully in the third embodiment.

Figure 15A:
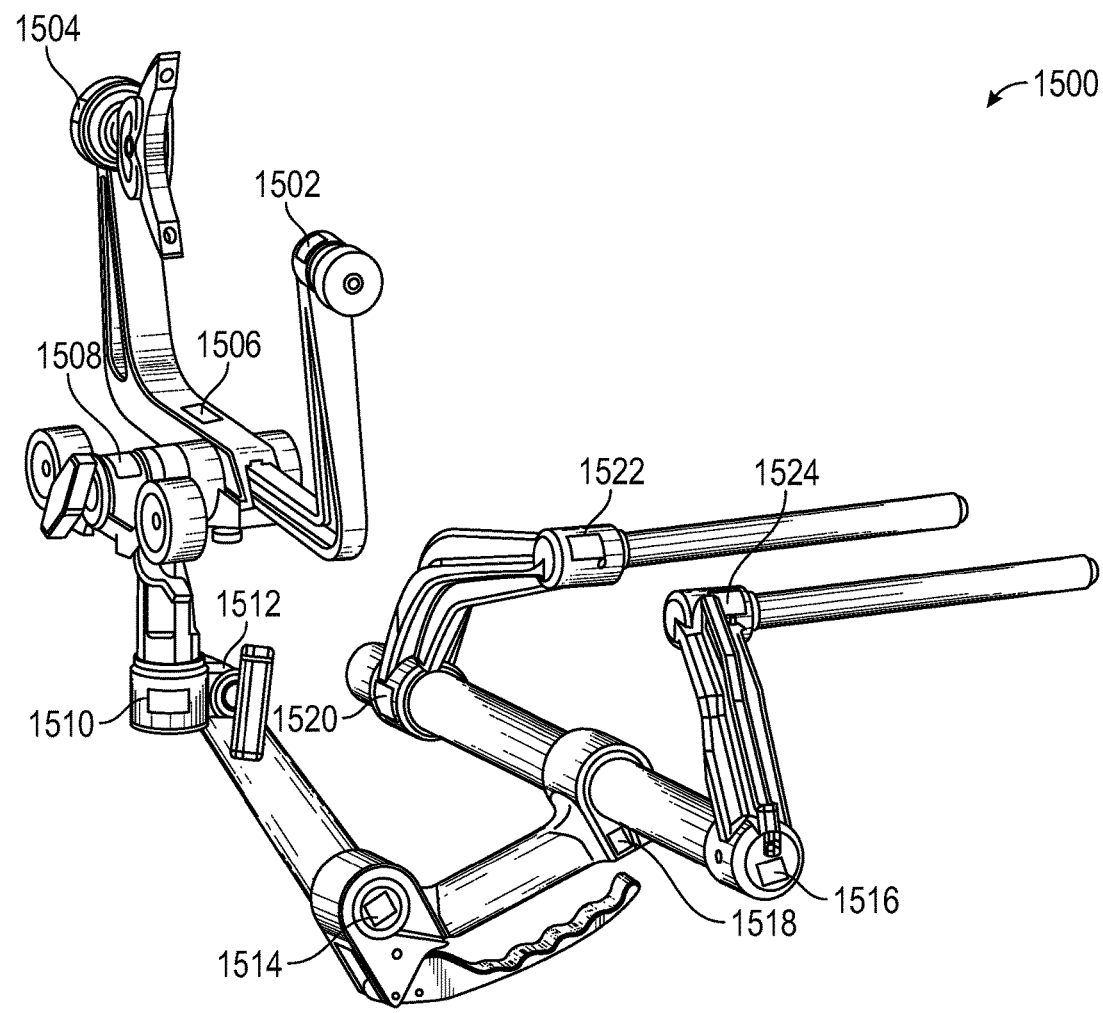
FIG. 15A is a diagram illustrating a skull clamp headrest including a plurality of RFID chips according to the second embodiment.
Figure 15B:
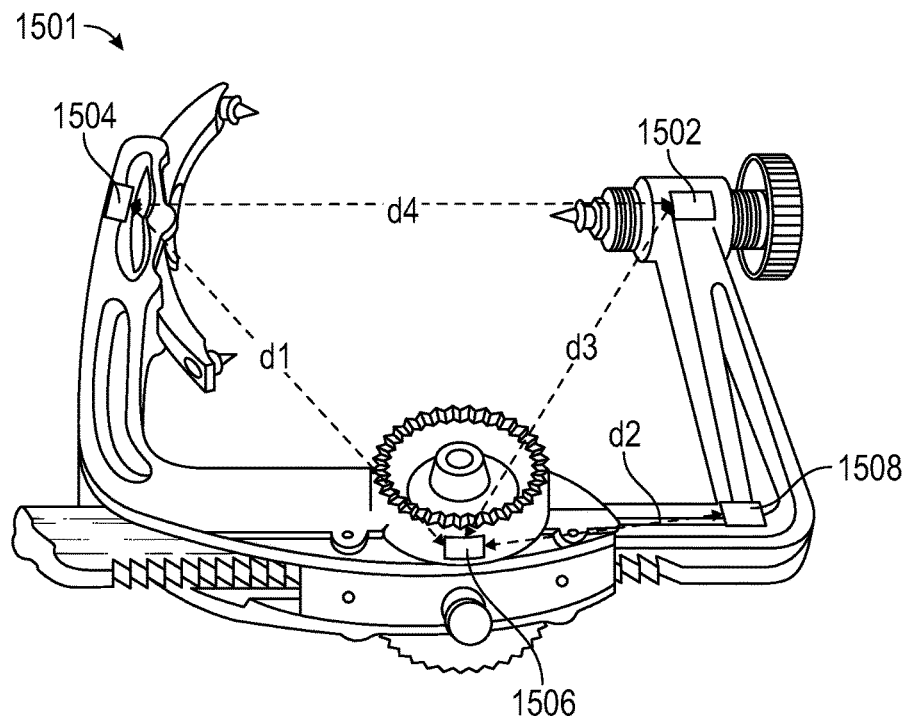
FIG. 15B is a diagram illustrating the skull clamp portion of the Mayfield heardrest according to the second embodiment.

Referring to FIGS. 15A-15B, a skull clamp-type headrest 1500 can be used to position the patient's head in lieu of the donut discussed above. The head rest 1500 can be, for example, a Mayfield headrest, and includes a clamping portion 1501 which includes RFID chip 1504 near the two pin side and RFID chip 1502 near the one pin side of the clamp, an RFID tag 1506 near the base adjustment portion, and an RFID tag 1508 in a corner portion. As shown in FIG. 15A, a swivel portion is joined to the clamping portion 1501. The swivel portion may be similar to the swivel adaptor and base unit described in U.S. Patent Publication No. 2006/0190010 to Easton published on Aug. 24, 2006, the contents of which are incorporated herein by reference. A plurality of RFID chips 1510, 1512, 1514, 1516, 1518, 1520, 1522, 1524 can be disposed on the pivot/swivel joints of the swivel portion of the head rest 1500.

The respective orientations of the RFID chips in the headrest 1500 can be used to determine the exact spatial orientation of the support arm and clamping portion. For example, the RFID chip 1506 near the adjustment portion can measure a vector including an orientation angle and displacement of the chips 1502, 1504, 1506, 1508 from a base line orientation. The vector can be represented as [$\theta$, d1, d2, d3], wherein $\theta$ represents the angle from the baseline orientation, d1 represents the distance between chips 1506 and 1504, d2 represents a distance between chips 1506 and 1508, and d3 represents a distance between chips 1506 and 1502. The RFID chip 1504 can measure a distance d4 from chip 1502 (or vice versa). The RFID chip 1506 can send a message to the DCE including the vector and the distance d4 (received from one of chips 1502, 1504), the various RFID chip identities, date and time stamp of the data collection, and other data collection related metadata. The DCE can send this message to the server device. The server device can utilize machine learning techniques as previously described herein to predict or determine the position of the headrest and thus the position of the patient's head based upon the vector and d4.

Referring to FIGS. 15C-15F, exemplary operations of the headrest 1500, the DCE and the server will be discussed during two exemplary patient positions. In these examples, a baseline orientation is determined to be as shown in FIG. 15B. That is, the angle $\theta$ of the baseline orientation is 0 degrees. The RFID chip 1506 is an active-type RFID tag, and RFID chips 1504, 1506 and 1508 are passive-type chips.

Figure 15C:
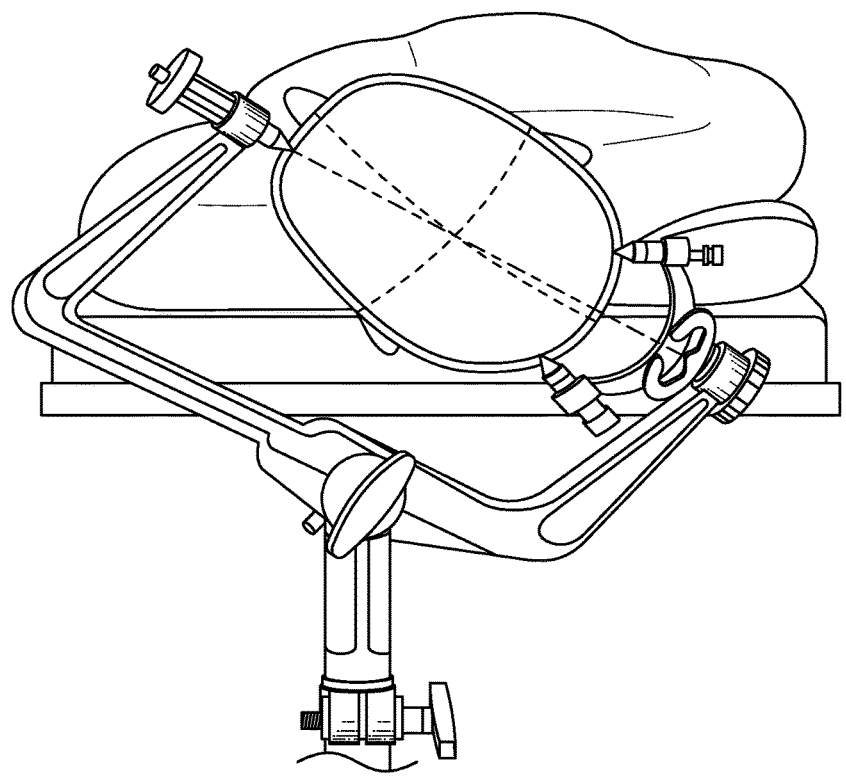
FIGS. 15C-15F are diagrams illustrating various orientations of a patient's head positioned in the skull clamp and the detected position signatures.

In FIG. 15C, a patient's head is shown positioned within the clamp 1501 while the patient is in the supine position. Prior to, or at this time, the RFID chip 1506 sends a registration message to the DCE including its identification information, data collection date and time stamp information, and other data collection related metadata. Further, passive-type RFID chips 1504, 1506 and 1508 receive power wirelessly from either the DCE or the RFID chip 1506, and send registration messages to the DCE including their identification information, registration date and time stamp information, and other related data collection metadata.

Figure 15D:
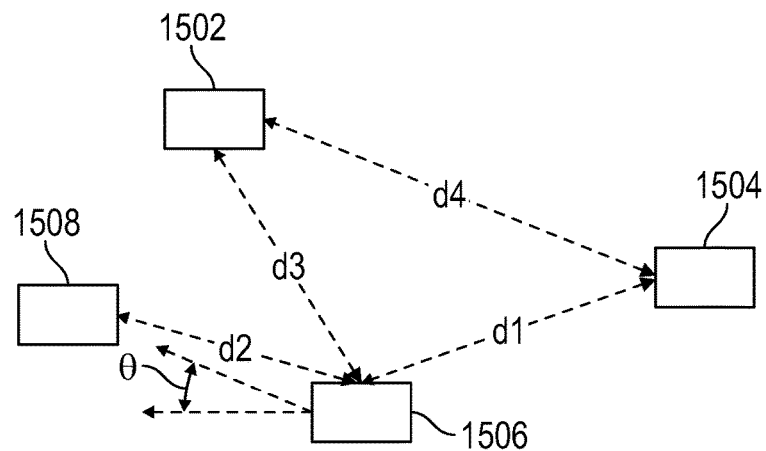

As shown in FIG. 15D, the RFID chip 1506 detects its displacement angle $\theta$ from the baseline orientation. For example, the sensor group of the RFID chip 1506 may include an accelerometer or orientation sensor for measuring the displacement angle. The RFID chip 1506 also measures the distances d1, d2, d3 to each of the RFID chips 1504, 1506 and 1508. The distance can be obtaining by measuring the RSS of a received signal from the chips or by NFC. Further, the RFID chip 1506 receives from one or both of RFID tags 1502, 1506 the distance d4 between RFID chips 1502 and 1504. The RFID chip 1506 send another message including the position vector [$\theta$, d1, d2, d3] and also the distance value d4 to the DCE. The value of $\theta$ is greater than 0 and may be, for example, 30 degrees. The values d2, d3, d4 are greater than their baseline values. The value d1 will generally be fixed and can be used for error correction.

Figure 15E:
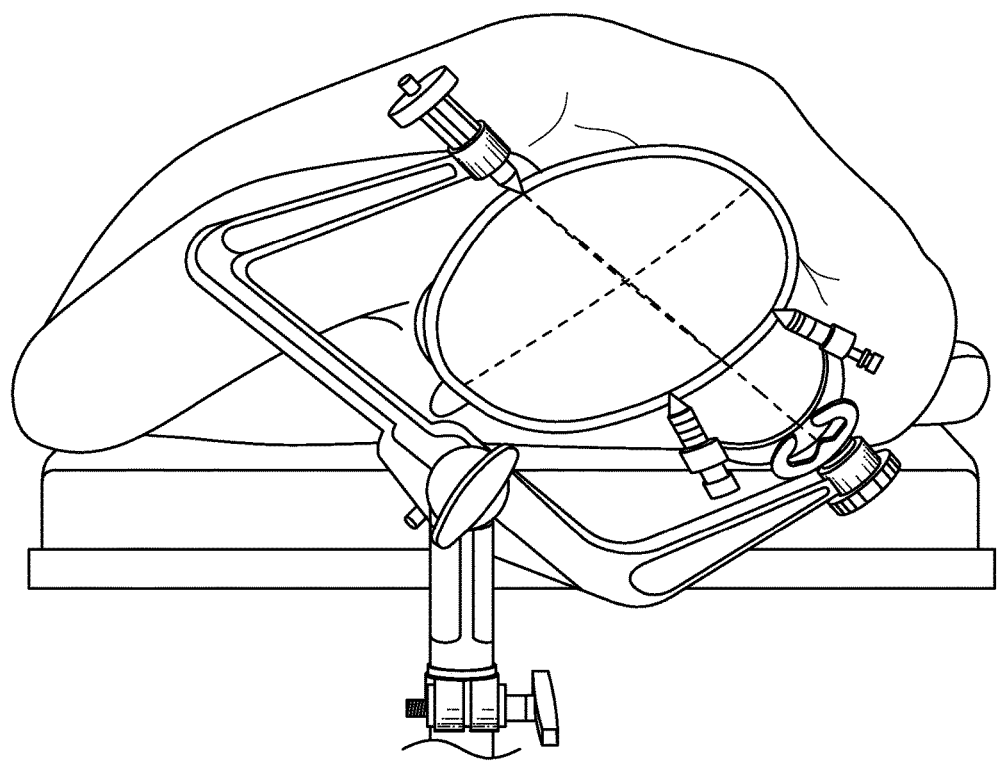
Figure 15F:
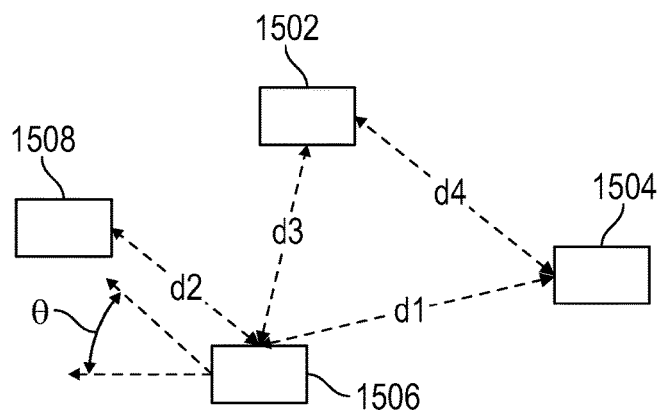

In FIG. 15E, a patient's head is shown positioned within the clamp 1501 while the patient is in the lateral oblique position. If not registered, the RFID chip 1506 sends a registration message to the DCE including its identification information. Then, the RFID chip 1506 obtains the position vector [$\theta$, d1, d2, d3] and also the distance value d4 and transmits this data in a message to the DCE as discussed above. The value of $\theta$ may be, for example, 45 degrees. The values d2, d3, d4 are greater than their baseline values, but less than the values of the case shown in FIG. 15C. The relative distance between the RFID chips on the head clamp 1501, the support arm as shown in 1500, and the RFID chips affixed to the various portions of the operating table as in the exemplary FIGS. 12C and 13C will also be transmitted to allow the determination of the location of the head clamp to the operating table (for example, is it affixed to the head or the foot of the operating table, etc.).

As discussed in embodiment 1, the patient can have a patient identification such as a wristband which includes an RFID chip that stores the patient identification. This information will also be transmitted to the DCE as discussed in embodiment 1. Similarly, the identification of the medical professional will also be transmitted to the DCE as discussed in embodiment 1. The DCE will send this information to the server device.

The server device can determine, utilizing machine learning algorithms as previously described herein, the patient position based upon the position signature received from the RFID chip 1506. For example, when the server receives the message including the position vector [θ, d1, d2, d3] and also the distance value d4 shown in FIG. 15C, it can determine that the patient's head is rotated as shown in FIG. 15C when the values of the position vector are within a first predetermined range. When the server receives the message including the position vector [θ, d1, d2, d3] and also the distance value d4 shown in FIG. 15E, it can determine that the patient's head is rotated as shown in FIG. 15D when the values of the position vector are within a second predetermined range different from the first range. Moreover, this data can be combined with the medical data received from the operating table as shown in FIG. 14B to increase the accuracy of the determination.

The server device can then compare the patient's position with patient attributes stored in the database to determine if a never event has or is about to occur. For example, if a patient attribute in the database indicates that the patient is scheduled to have a surgical procedure on a left portion of his head, yet the server determines that the head is positioned to expose the right portion as shown in FIG. 15C, the server device determines to a certain probability that a never event has or is about to occur. Similarly, the server device can compare the identification of the medical professional with the scheduled surgical procedure to confirm if a never event has or is about to occur. For example, if a medical professional is scheduled to do a surgical procedure on a patient different from the patient identification in the message received from the DCE, the server device can determine that a never event has or is about to occur. Further, if the server device determines that a medical consumable item such as a sponge with an imbedded RFID device is still in the patient as determined from the consumable's (sponge's) proximity to one or more of the RFID chips, for example, those affixed to the operating table and or the donut or head clamp at the time of completion of the surgery, the server device may determine that a never event has or is about to occur.

Figure 16A:
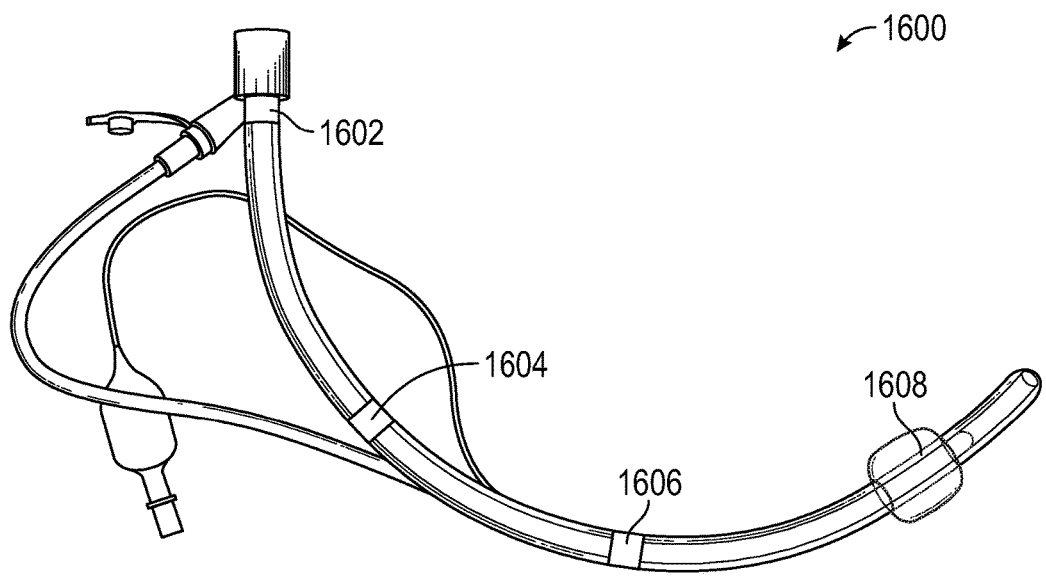
FIG. 16A is a diagram illustrating an endotracheal tube including a plurality of RFID chips according to the second embodiment.
Figure 16B:
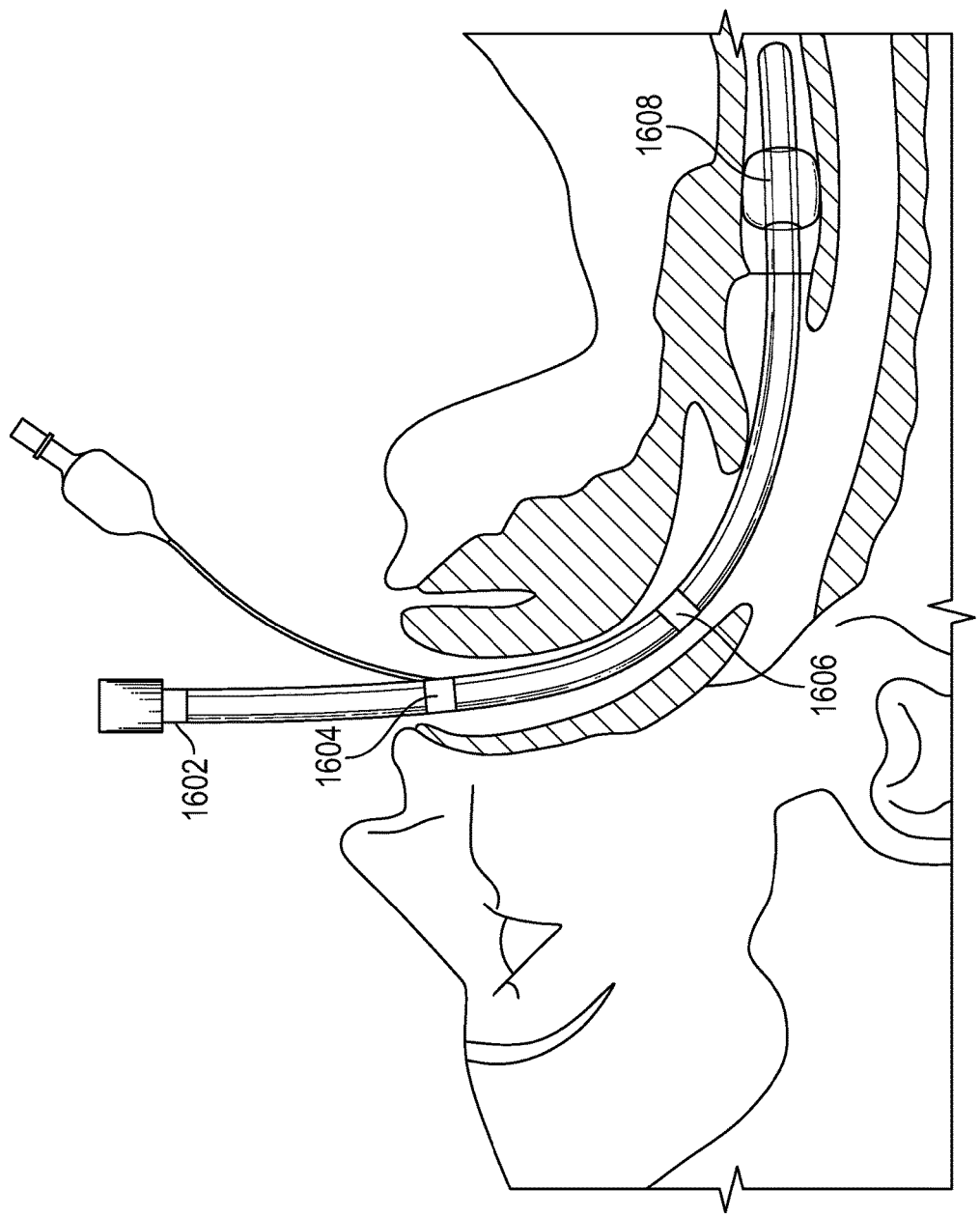
FIG. 16B is a view of the endotracheal tube positioning within a patient.

Referring to FIGS. 16A-16B, an endotracheal tube 1600 includes first RFID tag 1602, second RFID tag 1604, third RFID tag 1606, and fourth RFID tag 1608 on the air-filled cuff of the tube 1600. At least fourth RFID tag 1608 includes or is associated with pressure, orientation and temperature sensors. The first RFID tag 1602, second RFID tag 1604, and third RFID tag 1606 include or are associated with orientation sensors. The pressure sensors are disposed in an orientation where they can enable the detection and monitoring of the pressure of the cuff of the endotracheal tube at the interface between the cuff and the patient's airway. The temperature sensors are located along the course of the endotracheal tube and have a known position or measured distance from the end of the endotracheal tube. As shown in FIG. 16B, the first RFID tag 1602 and second RFID tag 1604 can preferably be positioned so as to be exterior and near the patient's mouth, while third RFID tag 1606 and fourth RFID tag 1608 are positioned to be in the patient. The tags can transmit data to the DCE representative of cuff inflation changes (pressure), the temperature distribution along the endotracheal tube, and the patient's core body temperature over time. The distribution of temperature along the course of the endotracheal tube at any particular moment in time used in combination with the known position of each temperature sensor within the endotracheal tube is transmitted to the DCE by the associated RFID chip. The DCE or server can then determine, using the previously described machine learning techniques, the likely position of the endotracheal tube leveraging the knowledge of the expected temperature drop off along the course of the endotracheal tube as it move from the trachea to the larynx to the pharynx to where it exits the patient at which point it then gets exposed to the ambient temperature in the operating room. In addition to using this temperature distribution to predict the position of the endotracheal tube in the patient at any given moment in time, changes in the temperature distribution along the course of the endotracheal tube over time can be used to determine whether the endotracheal tube has moved in the patient which can be useful, for example if the system predicts that the endotracheal tube is no longer in ideal position or is potentially at risk of becoming dislodged or conversely if the tube may potentially become positioned too deep in the patient's airway. The cuff pressure at any particular point in time or changes in the cuff pressure over time can also be used to predict situations that may pose danger or risk to the patient.

Referring to FIG. 17, an exemplary case is shown in which the Mayfield headrest 1500 can be used in place of the foot frame and foot cushion of the operating table (as is typical in neurosurgical procedures) 1202 and the endotracheal tube 1600 is inserted in the patient. The data from all of the RFID chips can be sent to the DCE, and used to determine the position of the patient and whether a never event has or is about to occur. Position data from the RFID chips on the endotracheal tube 1600 relative to the position data from the RFID chips on the operating table 1202 and the position data from the RFID chips on the Mayfield head clamp 1501 can be used together to improve the prediction of the patient's head orientation. For example, if RFID chip 1602 is closer in proximity to RFID chip 1502 as compared to its 1602 distance from RFID chip 1504 (as would be the case in the exemplary case shown in FIG. 17), this information can be used by the system to determine or further confirm the orientation of the patient's head in the head clamp. Specifically, the combined information from RFID chips on the head rest and those imbedded in the endotracheal tube enable more specific determination of where the patient's face or the frontal bone of the skull is relative to the head clamp as opposed to the patient's occiput or the occipital bone of the skull (back of the head).

Referring to FIG. 18, an eyelid occlusive dressing 1800 includes an embedded RFID tag 1802. Eye protection is used by anesthesiologists during neurosurgical cases to prevent eye injury (i.e. corneal abrasions, chemical injury from prep solutions, exposure keratopathy/keratitis). The eyelid dressing's embedded RFID tag 1802 can transmit orientation data to the DCE that can be used together with the orientation data from the Mayfield head rest 1500 and the head clamp 1501 to determine the orientation of the patient's head by, for example, calculating the proximity of the RFID tag 1802 to those on the Mayfield head clamp 1500 and 1501.

Referring to FIG. 19, rather than the donut 1300 shown earlier in FIGS. 13A-13B, the head rest can be a horse shoe style headrest 1900 which includes RFID tags 1902, 1904 and 1906. Further, the headrest 1900 can be installed on its own swivel joint. For example, a horse shoe shaped head rest can be affixed to the Mayfield apparatus rather than the head clamp 1501.

This information along with similar information about the proximity of the endotracheal tube 1600 to the RFID chips on the Mayfield head rest 1500 enhance the ability of the server and/or DCE to definitively determine the orientation of the patient's head and to predict the side of the patients head that will be operated upon, which the system can cross reference with the booking information for the case to determine if all information is in agreement or whether there may be risk for a never event.

It should be noted that in FIG. 1, one server was shown merely for ease of illustration. However, the server 114 may be a plurality of servers and databases connected to the network 112 via a load balancer and performing X, Y and Z axis scaling of the hardware and software.

Third Embodiment

Referring to FIGS. 20-48, a third embodiment will be discussed in which the server device 114 utilizes a trained model to make predictions regarding events.

Figure 20:
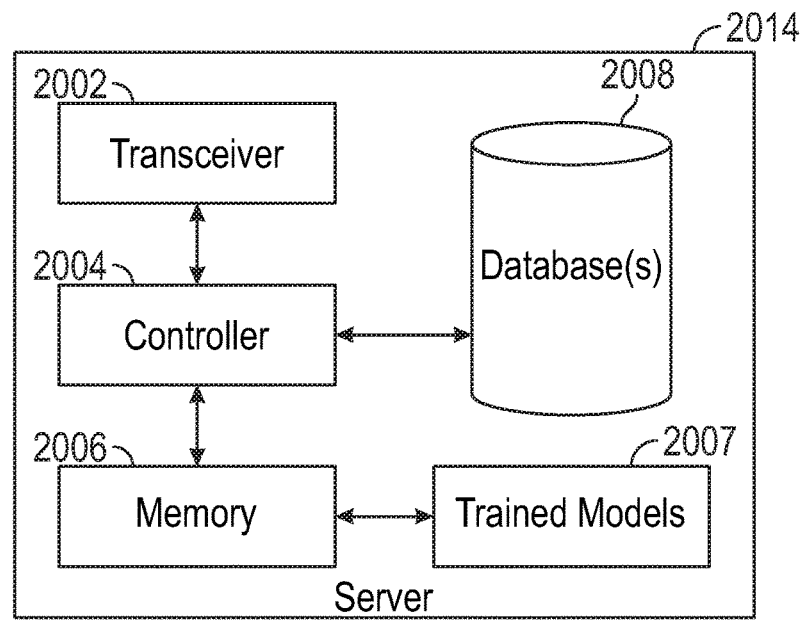
FIG. 20 is a block diagram illustrating exemplary portions of a server device according to a third embodiment.

Referring to FIG. 20, the server 2014 includes a transceiver 2002, a controller 2004, a first memory portion 2006, a second memory portion 2007 and one or more databases stored in another memory source depicted generally by 2008. The transceiver 2002 can be similar to the transceiver of the DCE. The transceiver 2002 receives medical data via the network from the DCE, data retrieval requests from the TMD 116 and sends replies to the data retrieval requests.

The memory portions 2006, 2007, 2008 can be one or a combination of a variety of types of memory such as RAM, ROM, flash memory, DRAM or the like. The memory portion 2006 includes instructions for configuring the controller 2004. The second memory portion 2007 includes one or more trained models. It should be noted that the database and the trained models can be included in the memory portion 2006. They are shown separately here in order to facilitate discussion.

The database 2008 can include: patient identifications, attributes associated with each patient identification such as dispositions, scheduled surgeries, location history, consumed medical items, etc.; patient events including a plurality of input attributes and a quantifiable outcome for each patient event (predicted delay time and/or predicted delay categorization); a plurality of medical item identifications and usage attributes associated with each of the item identifications (the usage attributes can include an identification of a medical professional that used the medical item, an identification of a patient for whom the medical item was used, a time duration for which the medical item was in a certain location, etc); and medical professional identifications, attributes associated with each medical professional such as scheduled surgeries, location history, consumed medical items, etc.

The controller 2004 is configured according to the instructions in the first memory portion 2006 to determine data in the database 2008 that is associated with the identification for each of the one or more RFID tags (received in the message from the DCE); store data in the message from the DCE in the database 2008 to be associated with the identification of the first RFID tag; and as will be discussed more fully below, predict an outcome associated with a clinical patient event based upon inputting attributes of the clinical patient event into trained model such as a neural network model or self-organizing map network.

Figure 21:
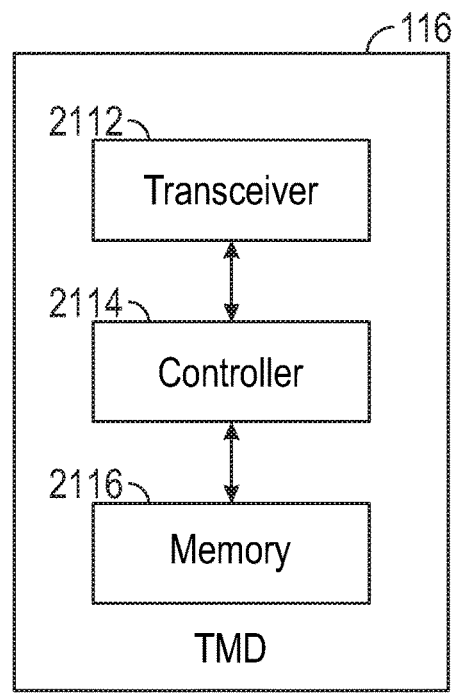
FIG. 21 is a block diagram illustrating exemplary portions of a TMD.

Referring to FIG. 21, the TMD 116 includes a transceiver 2112, a controller 2114 and memory 2116. The transceiver 2112 can be similar to the transceiver of the DCE. The transceiver 2112 receives information or resource requests such as, for example, http requests, via the network, from the client devices and other medical data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of patient events. The transceiver 2112 sends an information reply to the client device. The controller 2114 is configured according to instructions in the memory 2116 to generate either solely visualization data (i.e. a json object) or graphical displays (i.e. html markup and javascript) including visualization data retrieved from server 2014 as the information reply that can then be used to generate a display on the client device. For example, the graphical display can indicate the delay risk category or the predicted delay duration or length (magnitude) of each of a plurality of requested patient events as discussed later.

In the discussion here, the server 2014 and TMD 116 are shown as separate entities for ease of discussion. However, in actual implementation the server 2014 and TMD 116 may be implemented within a single computing device. Moreover, the portions of server 2014 may be distributed among various computing devices. For example, the trained models shown stored in memory portion 2007 or the database(s) 2008 could be stored at a plurality of different computing devices.

Figure 22:
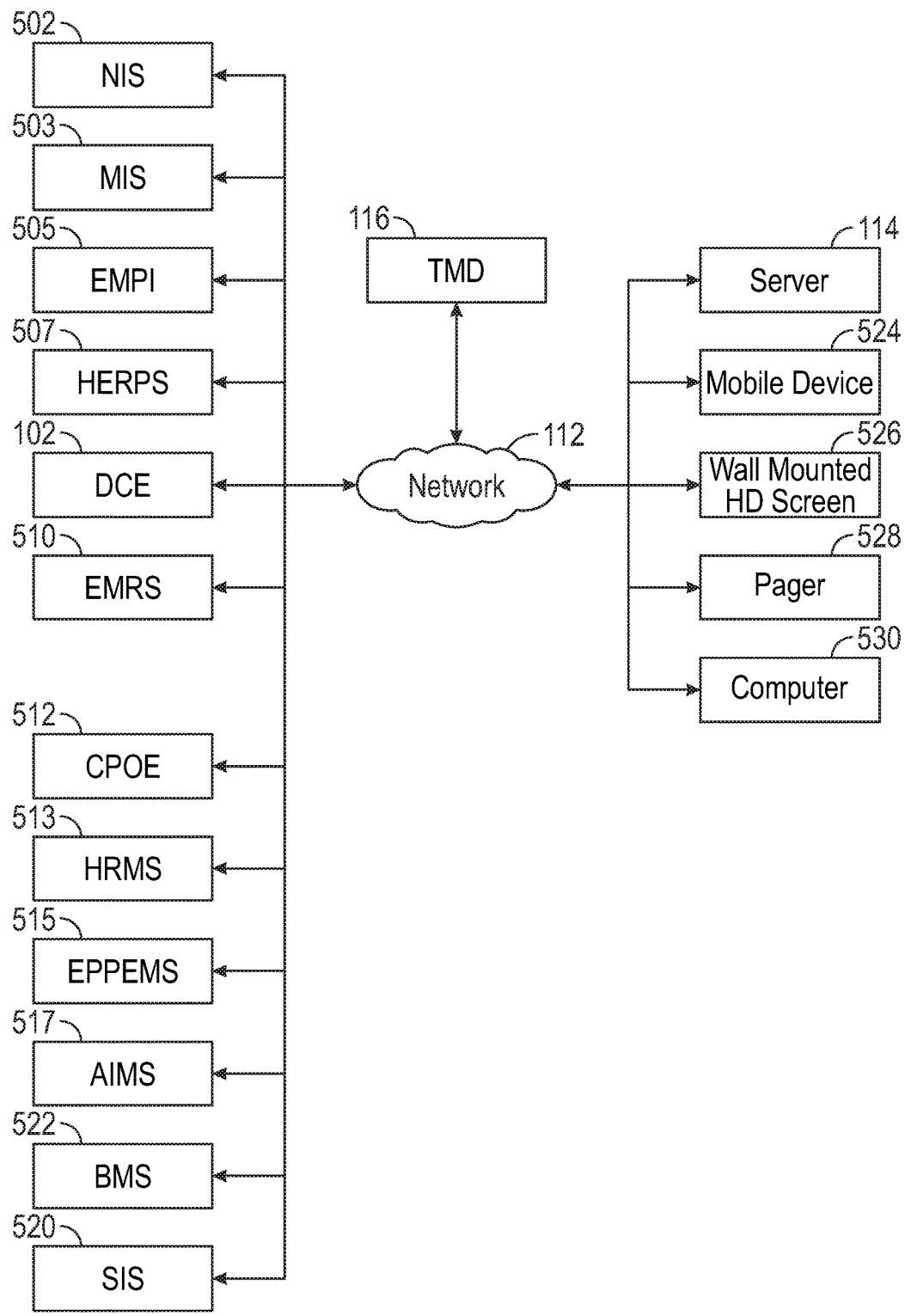
FIG. 22 illustrates an exemplary expanded operating environment in which the TMD receives medical data from the server device and various medical data sources and sends data to client devices via the network.

Referring to FIG. 22, an expanded exemplary operating environment is shown to illustrate how the TMD 116 communicates with various other medical data storage sources such as Nursing Information System (NIS) 501, Pharmacy Management Information System (MIS) 503, Hospital Enterprise Master Patient Index (EMPI) 505, Hospital Enterprise Resource Planning System (HERPS) 507, Electronic Medical Records System (EMRS) 510, Hospital Computerized Provider Order Entry (CPOE) system 512, Human Resources Management System (HRMS) 513, Employee Performance Planning and Evaluation Management System (EPPEMS) 515, Anesthesiology Information Management System (AIMS) 517, Perioperative Anesthesia System/Surgical Information System (SIS) 520, Hospital Bed Management System (BMS) 522 and client devices such as mobile device 524, wall mounted HD screen 526, pager 528 and a computer 530 via the network 112.

The server 2014 and TMD 116 can be considered the backend devices of the system. The client devices of the system can be a desktop or fixed device, a mobile device, or another system (i.e. another backend server) that can run a native application or an application in a web browser. The various client devices contain a controller that executes instructions and a transceiver. The client devices can communicate with the backend system over the network 116 using a remote procedure call (RPC) or via Representational State Transfer (REST)-like or REST-ful architectural style or a messaging based architecture (i.e. like Health Level 7). The client devices communicate with the backend devices over Hypertext Transfer Protocol (HTTP), over another networking protocol encapsulated in Transmission Control Protocol (TCP), via message queues (for example Microsoft Message Queuing, Rabbit MQ, etc.) or any other protocols, for example, User Datagram Protocol, etc. The devices may also communicate via a cellular network (GSM, GPRS, CDMA, EV-DO, EDGE, UMTS, DECT, IS-136/TDMA, iDEN AMPS, etc.) or via other network types (i.e. Satellite phones). The data exchanged between the client devices and the backend device(s) can optionally be encrypted using Secure Sockets Layer (SSL), Transport Layer Security (TLS) and decrypted on the client device(s) and the backend device(s). The data may also be encrypted in transit using methods other than SSL/TLS (for example using a keyed-hash message authentication code in combination with a secret cryptographic key) and can be decrypted by the client or backend devices. SSL/TLS can alternatively be used in conjunction with one of the alternative encryption methodologies (belt-and-suspenders). Also, as mentioned, a client device may also consist of another third party back end system, such as another server that communicates with a database server.

Figure 23:
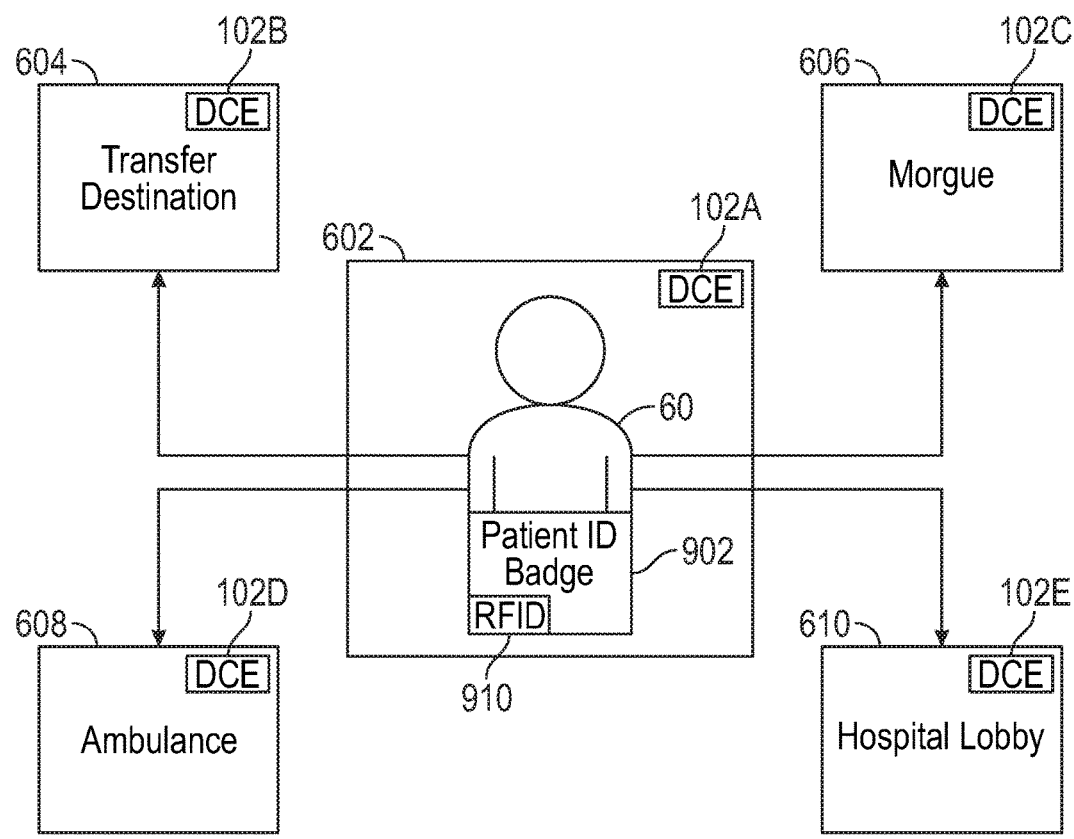
FIG. 23 illustrates exemplary patient events.

Referring to FIG. 23, exemplary cases of patient events in which the system (namely server, DCE and RFID tag) passively captures patient data will be discussed. The DCEs 102A, 102B, 102C, 102D are disposed in a position such as the ceiling beneficial for establishing wireless communication coverage for the respective room. Each of the DCEs receives medical data from the RFID tag 910 affixed to a patient identification badge 902 or a patient wristband (not shown). The DCE establishes communication with the RFID tag 910 by, for example, generating a general broadcast message, and receiving a registration message including medical data from the RFID tag 910 in reply to the broadcast message. Alternatively, the RFID tag 910 can self-initiate sending of the registration message periodically or in response to another external trigger.

Each of the DCEs 102A, 102B, 102C, 102D can store a unique identification associated with its physical location (referenced to the location, for example in a database such as 2008 where the DCE IDs and locations are stored) or store a physical location when it is put into service. The identification of the DCE and/or the location information from the DCE is sent in its communications with the TMD. Accordingly, the TMD can determine the location information for the asset associated with RFID tag.

Initially, the patient 60 is in the patient room or procedure suite 602. The DCE 102A in the room 602 receives the patient identification from the RFID tag 910 of the patient badge 902.

In a first exemplary patient event, the patient 60 is moved from room 602 to a transfer destination room 604 such as an ICU room, step-down room, pre-op, etc. The RFID tag 910 sends a message including the patient identification and location information from the RFID tag 910 of the patient badge 902 in response to the broadcast message from the DCE 102B.

In a second exemplary patient event (patient deceased), the patient 60 is moved from room 602 to morgue 606. The RFID tag 910 sends a message including the patient identification and location information from the RFID tag 910 of the patient badge 902 in response to the broadcast message from the DCE 102C.

In a third exemplary patient event, the patient 60 is moved from room 602 to a transport area 608. The RFID tag 910 sends a message including the patient identification and location information from the RFID tag 910 of the patient badge 902 in response to the broadcast message from the DCE 102D.

In a fourth exemplary patient event (patient discharge), the patient 60 is moved from room 602 to hospital lobby 610. The RFID tag 910 sends a message including the patient identification and location information from the RFID tag 910 of the patient badge 902 in response to the broadcast message from the DCE 102E. Alternatively, location information could come from the DCE rather than the RFID tag in each of the four examples.

Figure 24:
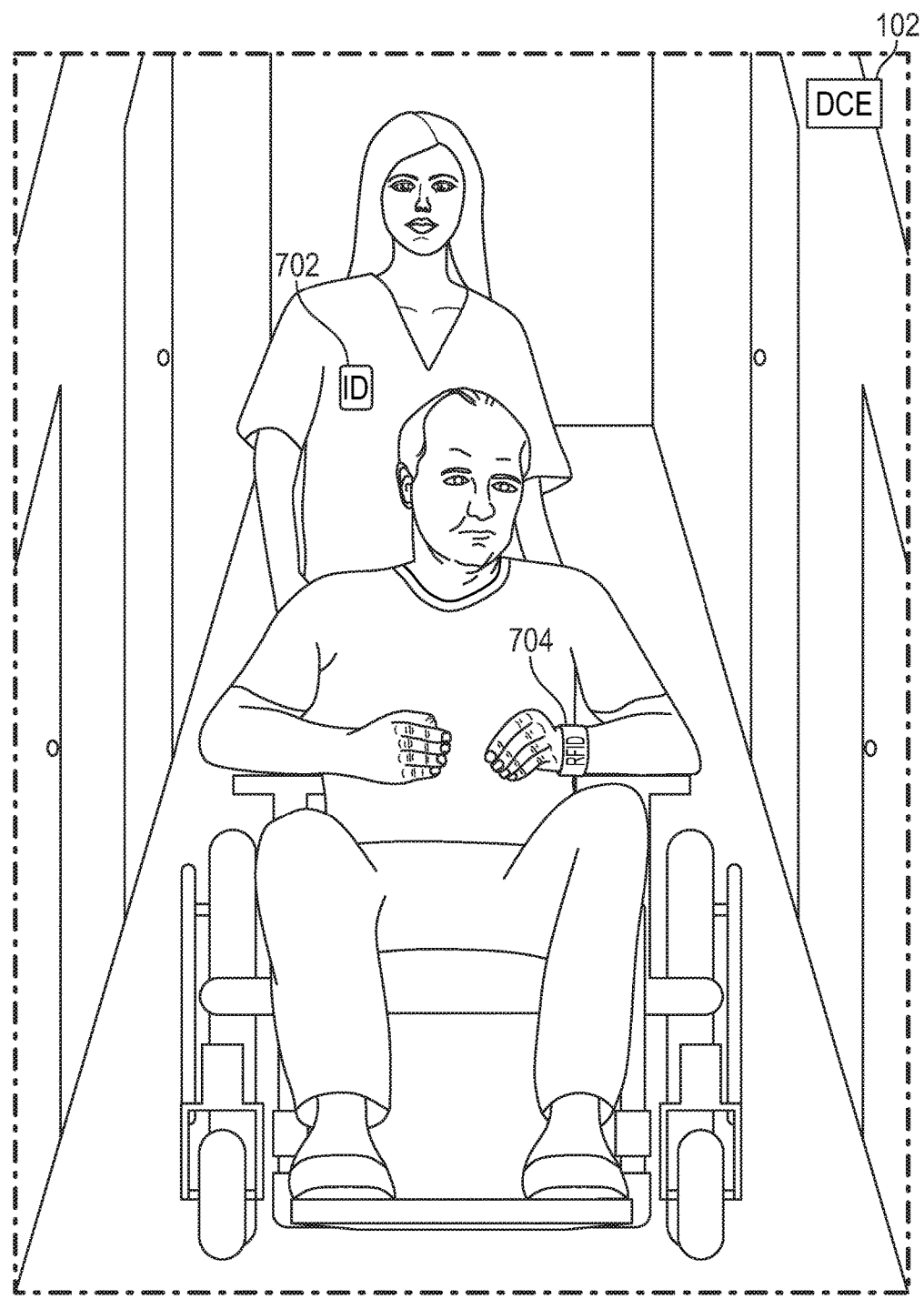
FIG. 24 is an illustration of a patient being transferred by a medical professional
Figure 25A:
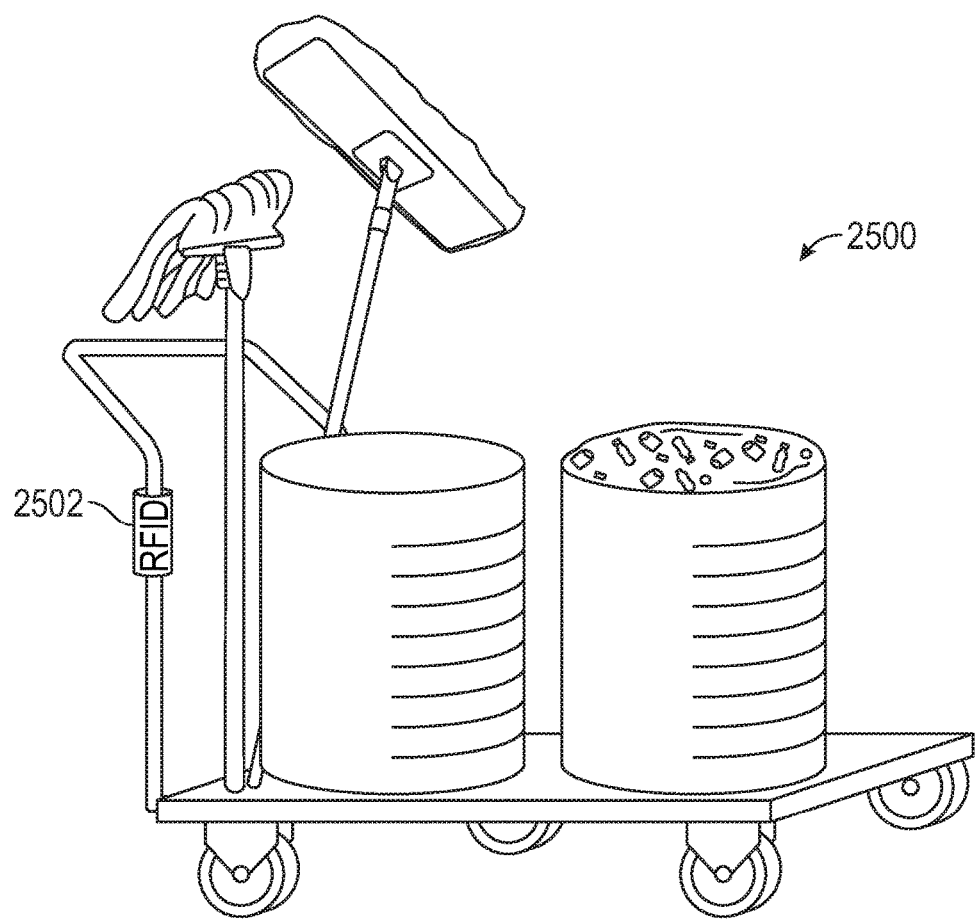
FIGS. 25A-25B are illustrations of janitorial equipment including an RFID tag and janitorial staff disposed near the janitorial equipment wearing a medical identification including an RFID tag.
Figure 25B:
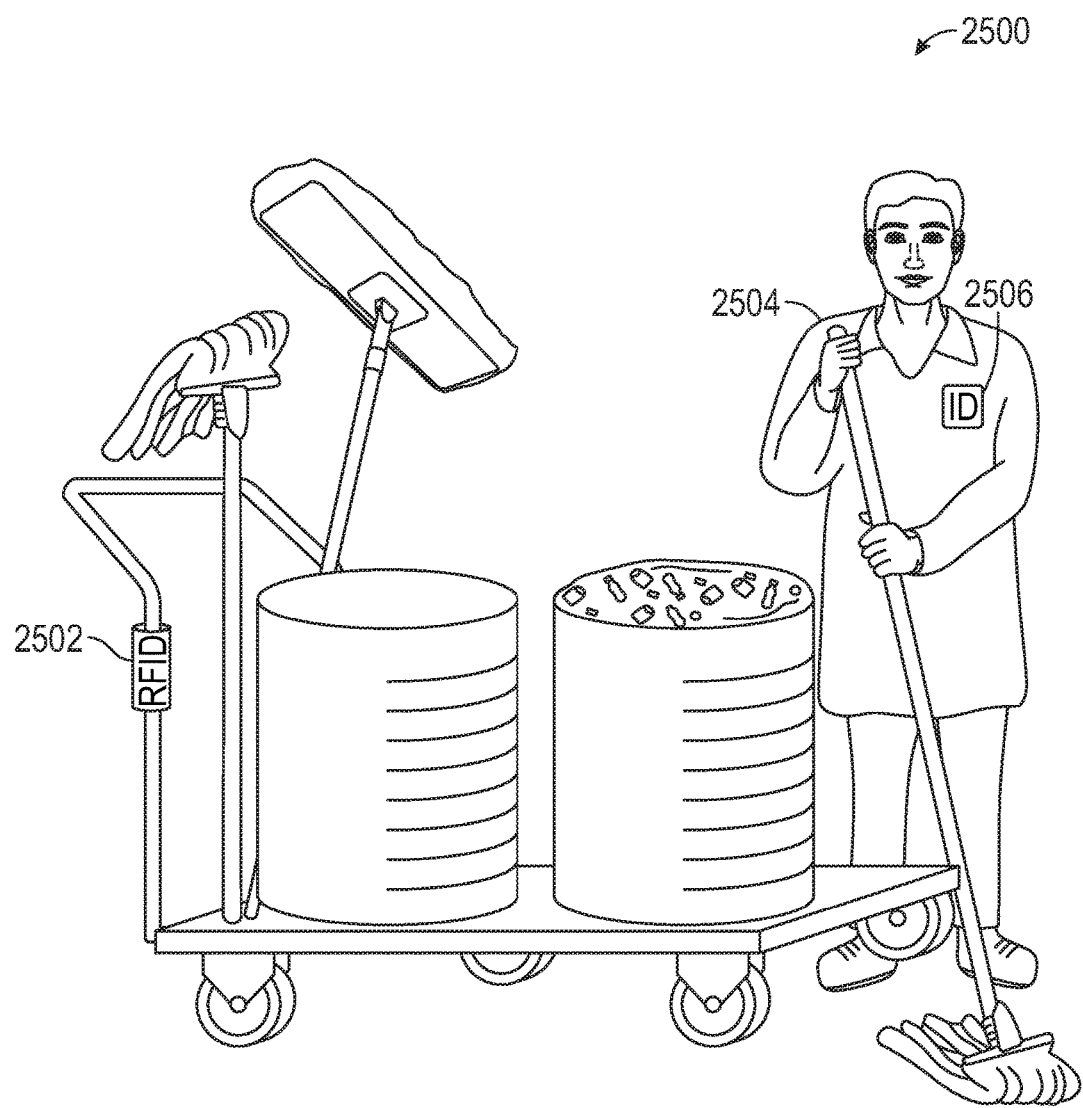

In each of the four examples, the respective DCE will send the information received from the RFID tag 910 to the server device 2014 via the connection to the network 112. As depicted in FIG. 24, the patient, whose wristband includes an RFID tag 704, is transferred between rooms by another medical professional who has their own identification 702 with an RFID tag that communicates with the DCE 102. Therefore, the server 2014 can collect data regarding the medical professional that is transferring the patient. As depicted in FIGS. 25A-25B, after the patient has left a room (due to, for example, a transfer), the janitorial staff will enter the room to begin cleaning for turnover. RFID tags 2502, 2506 communicating with the DCE can include on the identification of the janitorial person 2504 and the janitorial equipment 2500. Therefore, the server 2014 can collect data regarding the progress to room availability by collecting information about when the janitorial staff and/or janitorial equipment arrive, and when they subsequently leave the room of interest. Sever 2014 can also have trained NNMs for acting on this data and data about the service line and patient that previously occupied the room to predict turn over time, or delays thereof, etc.

Only four examples of patient events were shown in FIG. 23. Of course numerous other types of patient events can be implemented such as patient admission, patient transfers, and room turnovers, etc.

Figure 27:
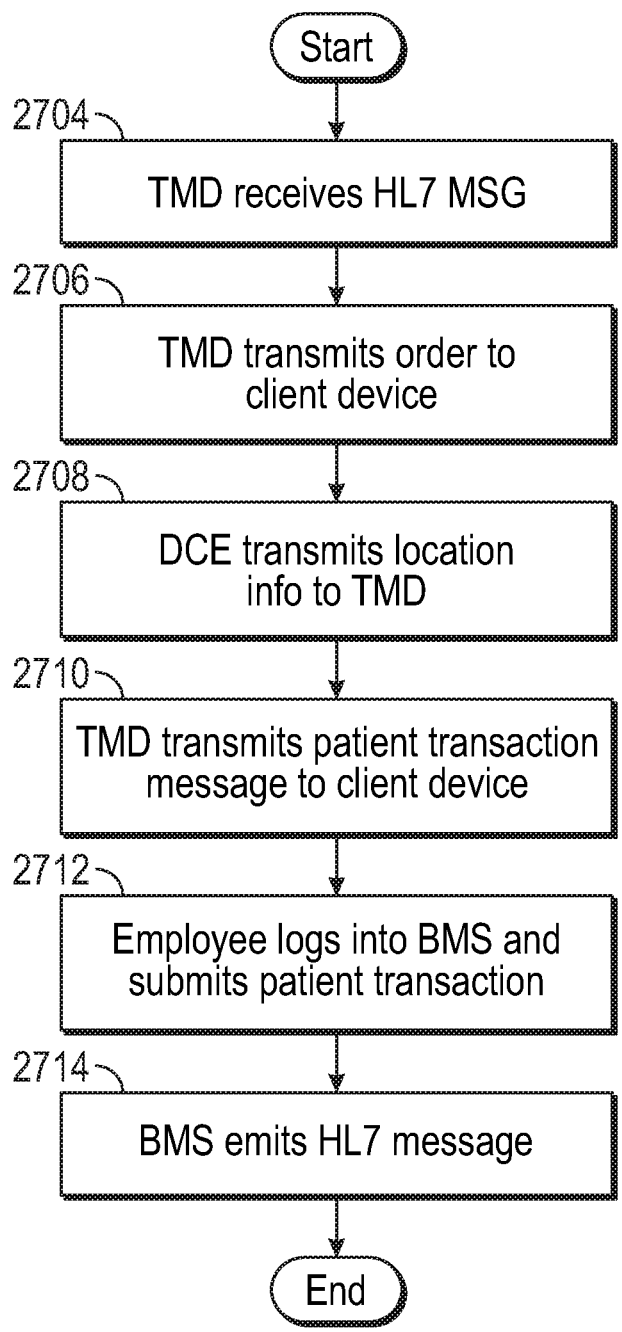
FIG. 27 is a flow diagram illustrating exemplary operations of the system during a patient discharge event.

Referring to FIG. 27, operation performed by entities of the system during a patient event will be discussed. At 2704, the TMD receives notification of an order written event (in this example, an HL7 message generated and transmitted by the CPOE system) triggered by a physician signing an order such as, a discharge patient order, an admit patient order, or a transfer patient order.

Real Time Notification of Discharge Patient Order

At 2706, the TMD transmits a notification of the order signed event to any subscribed client devices (via i.e., http, TCP, a message queue, web sockets, SMS, alphanumeric page, email, etc) such as the DCEs or client devices used in other worker processes or by hospital personnel that want real time notification of said order written events.

Predicting Discharge Order Fulfillment Delay

Consider this same discharge patient order event example: At 2704 the discharge patient order written HL7 message is received (by TMD) and the event is transmitted to any subscribed clients. At this juncture, triggered by the discharge patient order written event, the TMD can initiate a call to its trained NNMs utilizing data in the system such as attributes about the patient and the patient's hospital stay, the service line the patient is on, etc. to predict the likely discharge delay categorization (i.e. not delayed, delayed, significantly delayed) and/or the likely duration (magnitude) of any predicted discharge delay.

Predicting Definitive Discharge Order Fulfilled Events

At 2708, a DCE in proximity to the patient 1006 registers the patient identification from the RFID tag of the patient wristband and transmits location information of the patient to the TMD. This process is repeated a plurality of times (not shown) to track the patient and identify any location changes (the DCE that successfully communicates with the patient's RFID chip will change as the patient is moved from the current patient room 602 to the lobby 610 (assuming for this example that the patient gets discharged home). When the TMD receives a plurality of data points from a plurality of DCEs that collectively are determined to be consistent with fulfillment of the discharge order written event, the TMD passively "knows" or determines that the patient has "physically left the building." For example, consider the following RFID derived data received from a plurality of DCEs:

1. Patient 60 left assigned room 602 with transporter,
2. Patient 60 in hallway(s) with transporter,
3. Patient 60 in lobby 610 with transporter,
4. Patient 60 no longer in lobby 610 or in facility,
5. Transporter is present in the facility, but no longer in the lobby 610, nor in proximity to patient 60

The TMD uses business logic along with its trained NNMs to predict whether a given series of data from the DCEs, such as the enumerated series of RFID to DCE messages above, are likely consistent with fulfillment of a previously received provider order written event (such as: discharge patient order, an admit patient order, or a transfer patient order) or a "turnover patient room request."

Real Time Notification of Discharge Order Fulfilled Events

Again 2708 represents a plurality of TMD/DCE/RFID communications and TMD processing of data resulting from said communications related to each provider order written event or other order written event or room turnover request it receives; detail not shown. Returning to our discharge patient order example, upon completion of 2708, the TMD "knows" the patient has been physically discharged from the facility most likely at a point in time before the Bed Management System (BMS) has been updated to reflect this "reality" and this knowledge attained by the TMD can be shared or transmitted to interested parties or processes via subscribed client devices 2710. Eventually, a worker at the hospital likely will update the Bed Management System 2712 to indicate the patient has been "physically" discharged. In fact, the TMD could be employed to actually automate the update of the room status in the BMS system (BMS would be a client device notified at 2710) removing the reliance on the human actor to keep the BMS in synchronization with "reality" and eliminating the lag between when the physical status changes ("patient has left the building") and when the BMS reflects this state change. The TMD will be notified at 2714 when the BMS has been updated to show patient 60 has been discharged from previously assigned hospital bed 602. The difference between when the TMD "knows" the patient has "left the building" 2708 and when the BMS system is updated to reflect this "reality," 2712 is potentially "invisible" waste. Invisible, because without a system like the inventive system, there is no way for the waste to be perceived from a review of data in the BMS without supplementing the data set with some form of direct observation or data derived therefrom. TMD can also be leveraged to deploy a room turnover representative (janitorial services) to vacated patient room 602 by transmitting a patient 60 in hospital room 602 has been discharged notification (to janitorial services turnover personnel with subscribed client devices at 1010) in order to have the vacated patient room turned over ("turnover patient room request"). This new "turnover patient room request" would then start a pass of the process shown in FIG. 23 anew at 2704, this time tracking the fulfillment status and providing notification of fulfillment status changes for the "turnover patient room request." This real time notification triggered at the time the actual "physical" state change occurs ("patient has left the building" then triggers "turnover patient room request") allows the hospital system to eliminate the "invisible" waste.

Predicting Room Turnover Request Fulfillment Delays and Resource Allocation

At the time the patient is discharged as determined by the TMD at 2710, the TMD, using its business logic and the requisite TMD trained NNMs, can also predict the expected delay for the room turnover activity, if any, and if needed recommend the allocation of any available resource(s) that it determines may be available and able to mitigate the likelihood that there will be a delay (waste) or to reduce the magnitude (duration) of the delay. A similar resource allocation process could be performed by the TMD in relation to discharge delays it predicts (deploying additional human capital, for example an available nurse, to facilitate and assist with the discharge and by doing so potentially mitigate the predicted waste). The TMD would be able to determine what resources may be available via communication with client devices and via communications with the other information systems in the exemplary operating environment shown in FIG. 22.

Real Time Tracking of Room Turnover Request Fulfillment Status and Continuous Machine Learning The DCE 102A in room 602 can also receive and transmit data from RFIDs 802, 806 to the TDE enabling the TMD to determine when turnover personnel (janitorial services) 2504 and/or equipment 2500 have entered and subsequently thereafter have left the vacated patient room 602. Note, the same process can be carried out in regards to other order requests, such as tracking arrival of transport personnel to patient room for discharge patient orders. Using this data, the TDE determines (predicts the occurrence) of the room turnover start and the room turnover complete events (which when detected would indicate fulfillment of the "turnover patient room request" at 2708) using business logic and trained NNMs the TMD has for this purpose. Furthermore, using the continuously collected "actual" data generated in the course of routine operations, the TMD's NNMs can be periodically retrained to help it better predict delays in the future. Said another way, the TMD can continuously "learn" from itself (from data sent to it from the DCEs) and in doing so be better at predicting when room turnovers will be delayed and how long the delay is likely to be. The same holds true for how the TMD can "learn" from passively collected patient discharge, patient admission, and patient transfer activity data. In essence, when the TMD's NNMs are retrained, the TMD is "studying" the historical data it collects over time and is learning, so called "continuous machine learning."

Real Time Notification of Room Turnover Request Fulfillment Event

After room turnover is "passively" determined to be complete (room turnover request is fulfilled) by the TMD and its trained NNMs, it can then emit a room turnover complete message to any subscribed client devices 2710. Upon sending such notification, a downstream process can then make use of this information, with one of the end result being the room would become available to be assigned to and receive a new patient. A hospital employee eventually will log into the BMS and update status of a room to "room turn over complete" and "room available" and TMD will receive this notification 2714. However, there likely is a difference between the time that TMD "passively" determined that the room turnover was complete as compared to when BMS "knows" the turnover is complete as the BMS only "learns" this when BMS is updated by the hospital employee to reflect that "reality." The TMD's timestamp is likely earlier as it reflects what actually occurred, whereas the BMS was reliant on a human entering the information. The difference between the two timestamps is the "invisible" waste that is eliminated by deploying the inventive system. In fact, just as described for patient discharge order fulfillment, the BMS (as a client device to the TMD) can also be updated automatically by receiving notification from the TMD once a "turnover patient room request" has been fulfilled; this removes any dependence on a human actor to keep the BMS in synchronization with the actual "reality" of the "physical" state of the system (room turned over and available for a new patient).

If the patient event was a discharge patient order for a deceased patient to be moved to the morgue, the DCE would not register the patient in the assigned room 602, but in the morgue 606 with another medical professional at 2708. If the patient event was a patient transfer, the DCE would not register the patient in the assigned room 602, but in the new location.

In such patient events, there will often be a lag between the time an event is ordered and when the event is completed and reported, for example in the BMS. For a patient discharge, there is a first time period from the time the discharge is ordered to the time the discharge has been confirmed by the TMD (by, for example, registering the patient in the hospital lobby) referred to here as discharge order fulfillment lag. There is a second time period from the time discharge has been confirmed by the TMD to when the hospital employee logs into BMS and submits patient discharged event referred to here as completed discharge reporting lag. The total discharge lag is the sum of both time periods, that is the total time elapsed between discharge order and room status change update entry in BMS. For a patient transfer, there is a first time period from the time the transfer is ordered to the time the bed has been assigned referred to here as transfer bed assignment lag. There is a second time period from the time bed has been assigned to when the bed is available referred to here as transfer bed availability lag. There is a third time period from the time bed is available to when the transfer is fulfilled (patient is in the room as confirmed by the DCE) referred to here as transfer order fulfillment lag. There is a fourth time period from the time the transfer order is fulfilled to when the hospital employee logs into BMS and submits patient transferred event referred to here as completed transfer reporting lag. The total discharge lag is the sum of all four time periods, that is the total time elapsed between transfer order and room status change update entry in BMS. There are similar lags for patient events such as room turnover, patient admission, etc. The system according to the third embodiment can reduce these total lags by predicting delay for a patient event and reallocating resources accordingly.

Creating a Trained Neural Network Model to Predict an Outcome

Figure 28A:
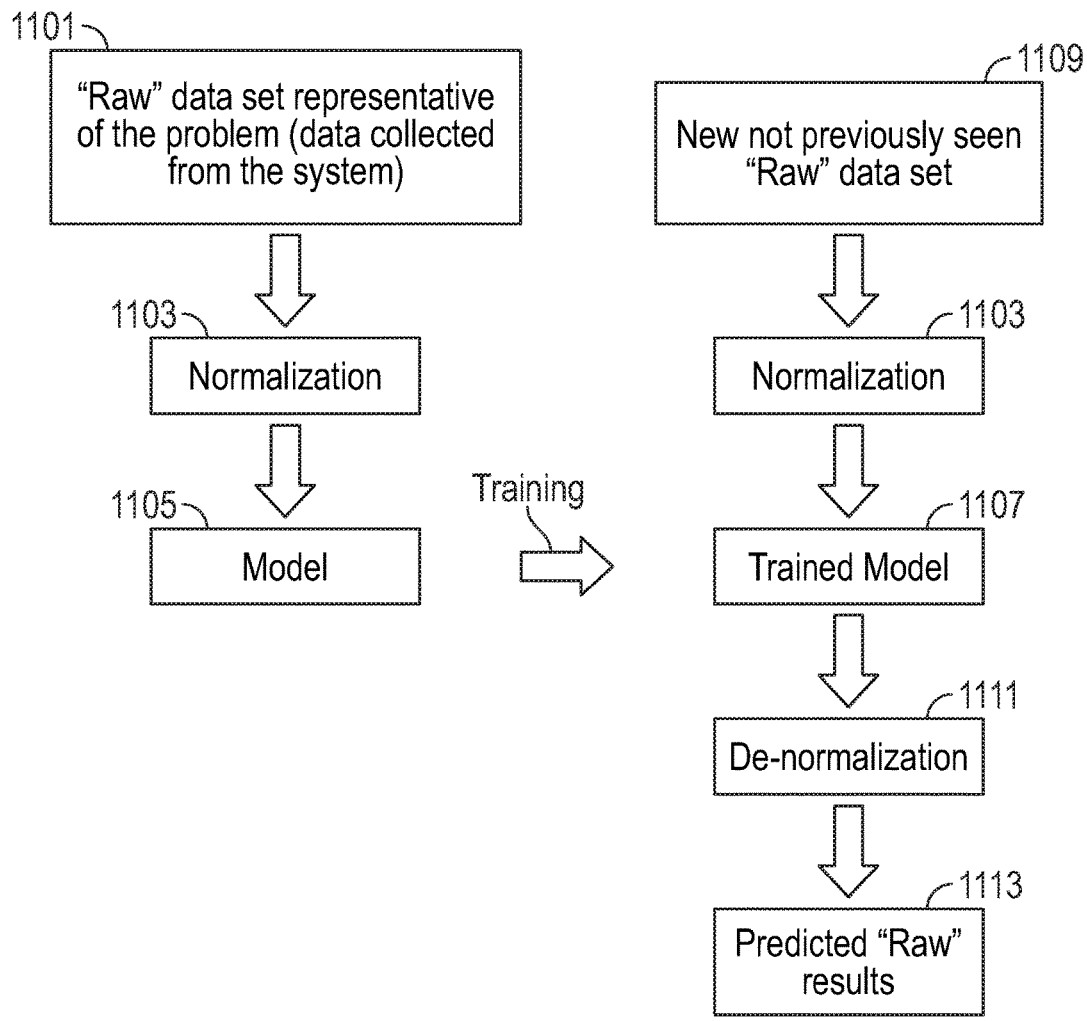
FIG. 28A is a block diagram illustrating high level operations for creating a trained neural network model (NNM) according to an embodiment.

The server device 2014 stores a trained neural network model which is used to predict an outcome of a clinical patient event. A representation of the process for creating, training and using the trained model is shown in FIG. 28A. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 28B, the raw data 1101 and new data 1109 include sets of data [1,2 ... N] with known outcomes and properties of each of the data. For example, the data can be past patient events with known delay outcomes. The properties of the data can be discharge attributes.

The model 1105 is trained by an iterative machine learning algorithm. After initial deployment, the server 2014 will also continuously collect data from a variety of sources along with actual related healthcare system clinical and operational outcomes; this data can subsequently be used as training data. As such, the TMD/server is able to continuously learn and improve its ability to predict the outcomes of interest. In addition, the knowledge of the system can continue to evolve in the event the system dynamics change. Take, for example, the time between when a healthcare worker signs a discharge order and the time of the patient's actual physical disposition from the facility in question. There is a relationship between the multitude of attribute data the system collects about a discharge and the outcome in question. Exemplary discharge attributes the server 2014 collects about a pending discharge that can be used: the patient's age, the age of the patient's next of kin, the age of the patient's spouse, the zip code of the patients spouse and or next of kin, the patients insurance, the patients credit rating, the patients employment, the patient's current hospital ward, the discharging medical facility, the discharging medical or surgical specialty, the identity of the patients current nurse, the identity of the current charge nurse on duty, the identity of the individual that signed the discharge order, the current attending physician of record for the patient, the presence or absence of a resident physician as a participant in the patients recent hospital care, the presence or absence of a physician extender (nurse practitioner or physician assistant) as a participant in the patient's recent hospital care, the time of day the discharge order is written, the day of the week on which the order was written, the time of year the discharge order was written, the number of medications on the patients medication administration record at the time of discharge, the patient's laboratory results, the patients diagnostic imaging results, the patient's vital signs, to provide several examples. However, there is no one specific mathematical relationship or equation that describes the relationship between these exemplary attributes of the pending patient discharge and the outcome of interest (discharge lag time). However, because of the server's machine learning capabilities it has the ability to "learn" or be trained from pre-existing data and from the data it collects prospectively. Said another way, the server 114 "learns" from experience.

Data Set Encoding, Normalization and De-Normalization

Neural network models only use numerical double values for training and processing. Thus any nominal categorical data fields that are a part of raw data that will ultimately be used by models in the system are first encoded to numerical values and "raw" numerical data in many cases by a pre-processing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

An example of one of the independent predictors (input x-data) or discharge attributes that can be utilized by the system is the number of medications a given patient is prescribed at the time of discharge. Suppose a patient has 19 discharge medications and that this "raw data" value needs to be normalized to a −1 to 1 normalization range. If the actual range of the possible number of discharge medications is 0 to 50, for example, then to normalize this input x-data, the system's continuous or numeric normalization process would carry out normalization calculations similar to those illustrated herein. Initially, the value can be plotted on an actual range as shown in FIG. 29A. Then a normalization calculation can be carried out as shown below:

$$\{[(19-0.0)*(1.0-(-1.0))]/(50.0-0.0)\}+(-1.0)=-0.24$$

Referring to FIG. 29B, equivalent value plotted on a normalization scale is shown.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 30A. For example, one of the attributes that may be used is the discharging medical or surgical specialty. In this case the hospital has three medical and surgical specialties that discharge patients: hospital medicine, general surgery and orthopedic surgery. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is orthopedics {0.0, 0.0, 1.0} but the ideal (real) value is actually general surgery {0.0, 1.0, 0.0}, it is apparent that there is only error in two parts. Said another way, if the predicted and the ideal (real) values are compared, the first value is 0.0 in both (i.e. is correct), while the other two values are both wrong. This is unequal distribution of errors.

Due to this shortcoming of one-of-N encoding, particularly in instances when there are more than two nominal categories, the server can employ equilateral encoding (one-of-(N−1) encoding shown in FIG. 30B or one-of-(C−1) dummy encoding for encoding nominal categorical data. When equilateral encoding is used fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$\text{distance} = \sqrt{\frac{(i_1 - a_1)^2 + (i_2 - a_2)^2 + \ldots + (i_n - a_n)^2}{n}}$$

Where the variables represent the following:
i=ideal (real) output value
a=actual (predicted) output value
n: number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
$=((0.5-0.933)^2+(1.0-0.25)^2)^{1/2}$
$=(-0.433^{2+0.752})^{1/2}$
$=(0.187489+0.5625)^{1/2}$
$=(0.749989)^{1/2}$
$=0.8660$
Ideal: {0.06698, 0.25}
Actual: {0.5, 1}
Euclidean Distance:
$=((0.06698-0.5)^2+(0.25-1)^2)^{1/2}$
$=(-0.433022+(-0.752)^{1/2}$
$=(0.1875063204+0.5625)^{1/2}$
$=(0.7500063204)^{1/2}$
$=0.8660$ Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others. While the exemplary embodiments herein do not detail every machine learning approach employed by the system to solve the technical problem, this should not be construed as an omission of these capabilities or approaches which the system can and in some case does leverage to solve the technical problem.

There are three primary categories of machine learning tasks: classification, regression and clustering tasks.

Classification

Figure 45A:
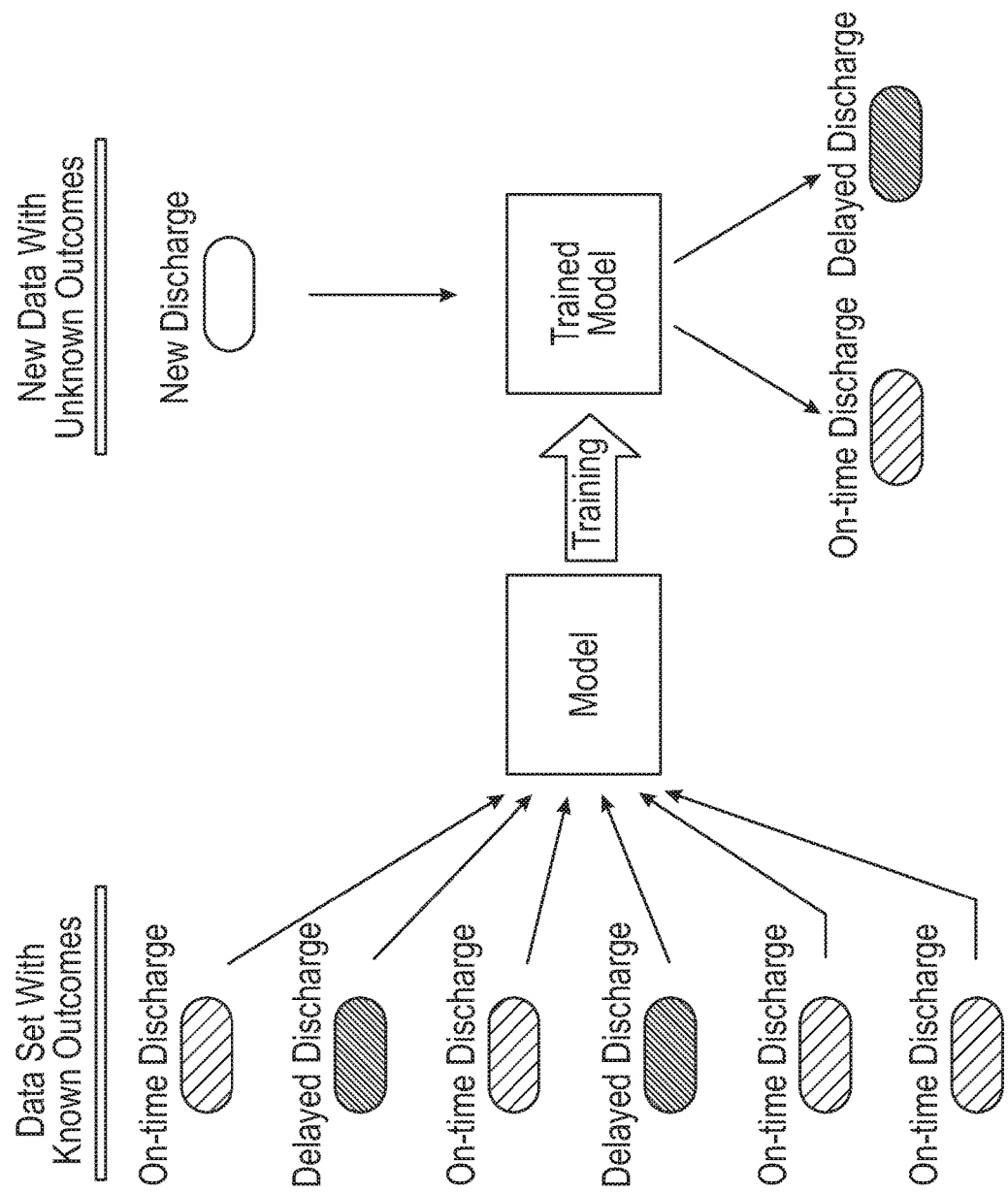
FIGS. 45A-45B are illustrations of a case in which the model is used to categorize the delay risk of a plurality of patient events.
Figure 45B:
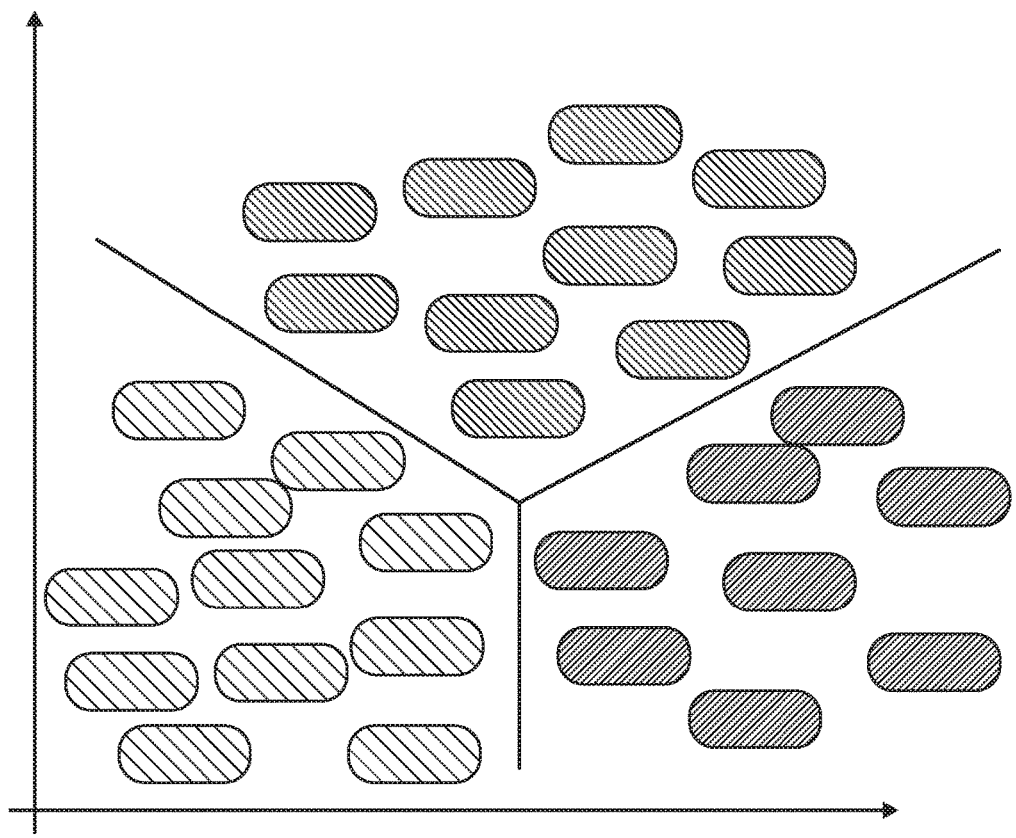

Referring to FIG. 45A-45B, a classification task for predicting delay risks of a discharge is shown. The machine learning task entails a two-step supervised learning process which utilizes both input and output data in the model training process. Model construction is done using a representative training data set and the model, once trained is used for classifying new or unseen cases, for example a discharge at risk of delay—predicts nominal categorical assessment or assignment. The inputs are collected discharge data attributes/properties. The output will be predicted categorical risk for discharge delay, not delayed, moderately delayed and severely delayed.

Regression

Referring to FIG. 46, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of discharge delay (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 2014 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boosts model performance and efficiency for some tasks.

Another exemplary task, for which the server 2014 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 31:
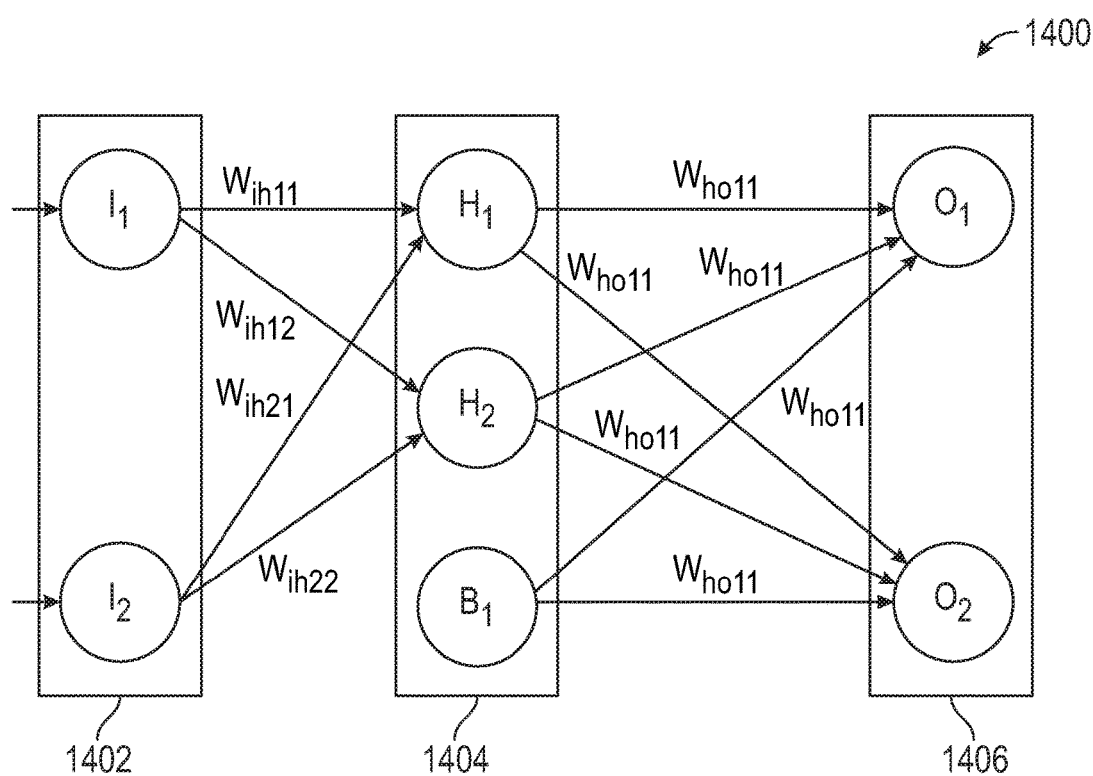
FIG. 31 is an illustration of an exemplary simple feed forward NNM.

Referring to FIG. 31, the backend devices can use a neural network model (NNM) 1400. The NNM 1400 includes an input layer 1401, a hidden layer 1404 and an output layer 1406. The input layer 1401 includes input neurons ($I_1$ and $I_2$) which provide input signals to the network without any processing units (processing units, described further herein are comprised of summation and activation functions). The hidden layer 1404 includes hidden neurons ($H_1$ and $H_2$) which provide a means to converge the network's solution leveraging additional processing units (summation and activation functions). At times, if these neurons are not present, the neural network may not be able to output the desired result. The hidden layer 1404 can also include bias neurons ($B_1$) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $I_1$ and $H_2$ has a synaptic weight of $w_{in}$ 12. The $w_{in\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus the notation $w_{in\ 12}$ not only denotes the neurons that are connected or involved but also the direction of the connection.

Figure 32:
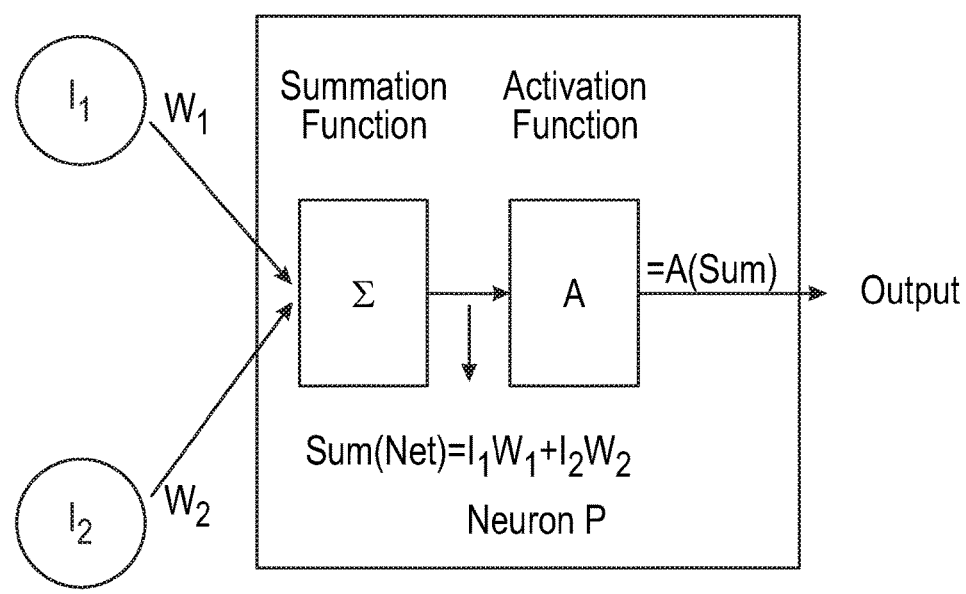
FIG. 32 is an illustration of an exemplary neuron of the NNM.

As shown in FIG. 32, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The Sigmoid Function $$f(x) = \frac{1}{1 + e^{-x}}$$

Figure 33A:
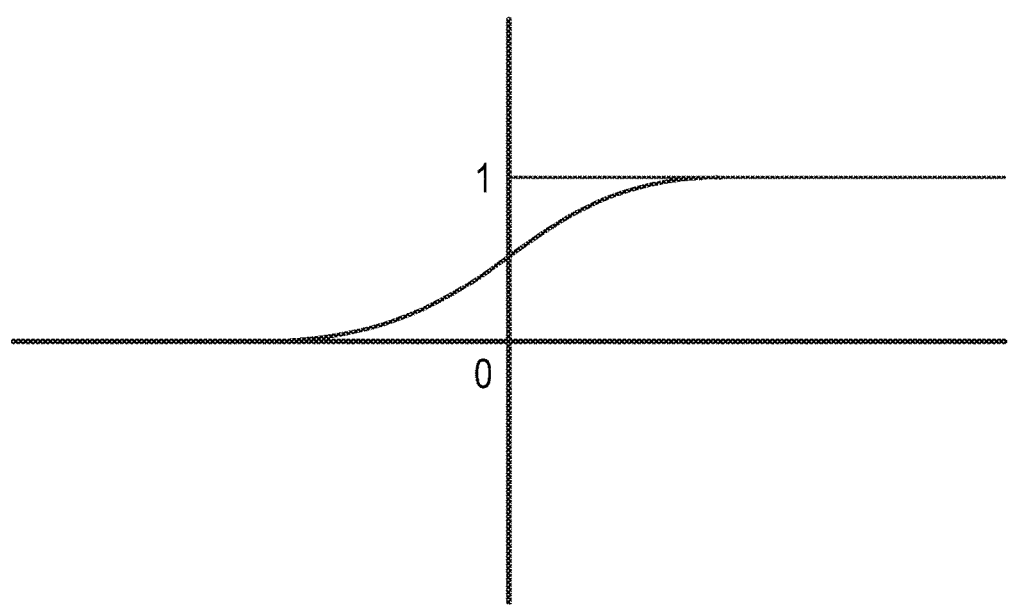
FIGS. 33A-33C are illustrations of exemplary activation functions for the neurons of the NNM.

As shown in FIG. 33A, a characteristic of the sigmoid function is that for all values on the x axis, the function output value (y axis) will lie between 0 and 1. The sigmoid function is used in instances where only positive outputs are expected.

The Hyperbolic Tangent Function $$f(x) = \frac{e^{2x} - 1}{e^{2x} + 1}$$

Figure 33B:
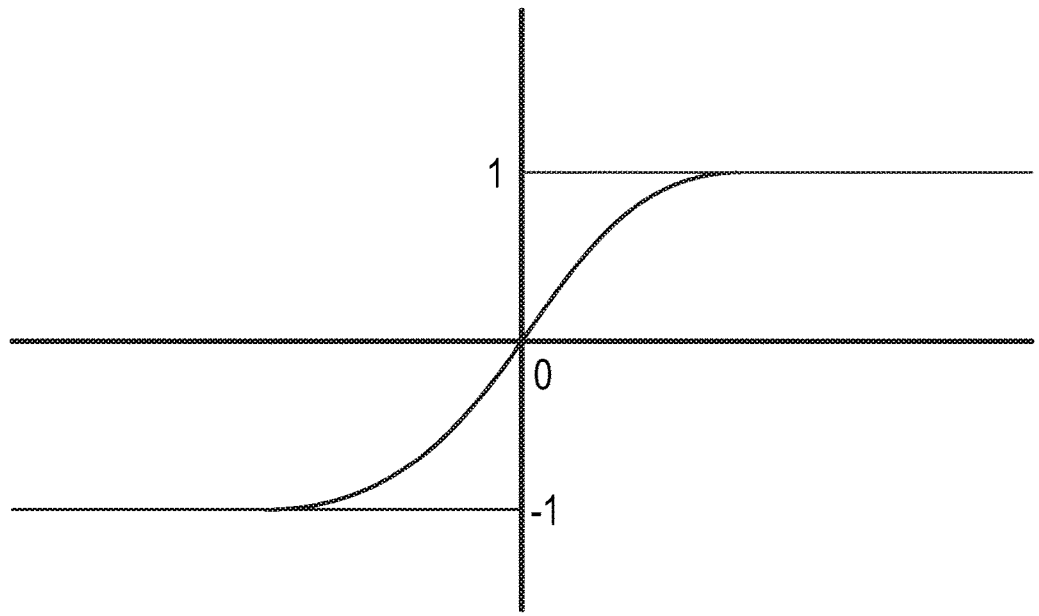

As shown in FIG. 33B, a characteristic of the hyperbolic tangent function is that for all values on the x axis, the function output (y axis) will lie between −1 and 1. The hyperbolic tangent function is used by the system in instances when both positive and negative outputs are expected.

The Linear Function $$f(x)=x$$

Figure 33C:
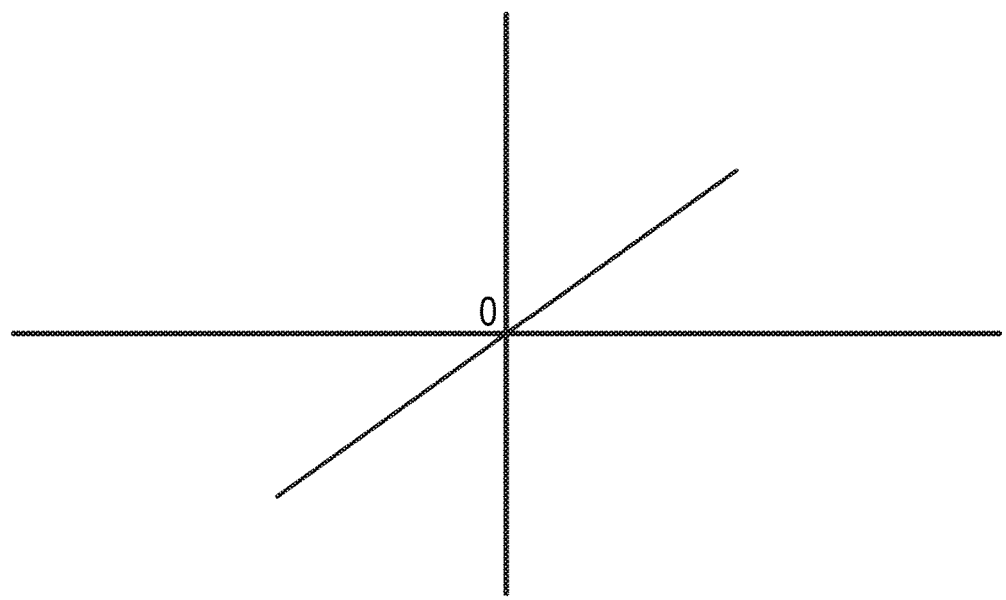

As shown in FIG. 33C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 2014 employs a plurality of activation functions to accomplish its objectives.

Figure 34:
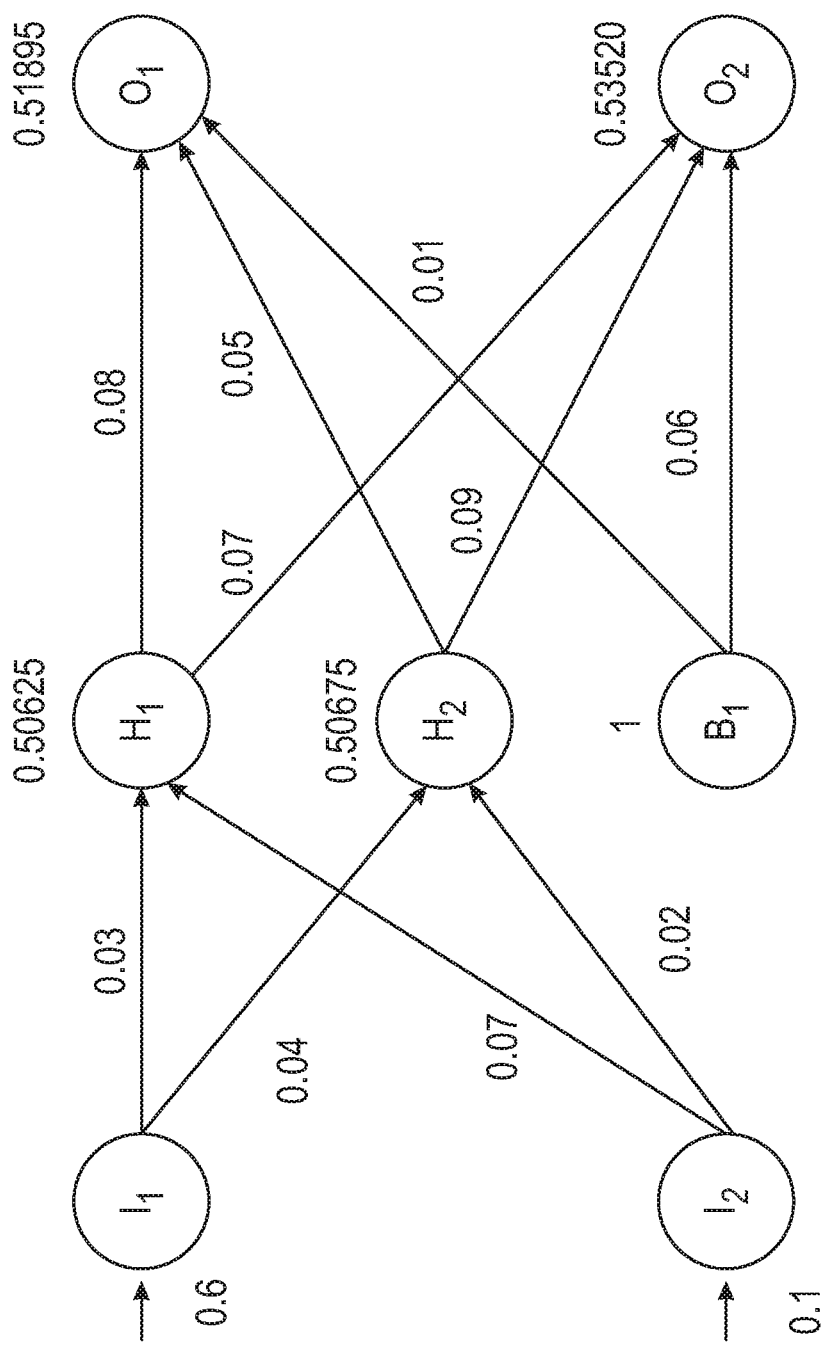
FIG. 34 is an illustration of exemplary computations of the NNM.

A NNM is a neural network architecture with a particular structure tailored to a particular problem statement. An exemplary problem statement the server's 2014 neural networks model is the prediction of whether a given patient discharge from a particular facility is likely to suffer from preventable delay or not (in this example, a categorical output is predicted). Using a trained NNM, the server 2014 predicts the likely outcome using a plurality of the properties or attributes of the pending patient discharge (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 34 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self Organizing Map (Kohonen), among others. Feedback networks, for example Elman and Jordan Networks, are at times leveraged by the system particularly in instances where the sequence of events (order of data) is material. Each neural network model also has a defined activation function. In the exemplary neural network of FIG. 34, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 34. This calculation process is used during each model training iteration and subsequently when the trained model is used to make predictions from previously unseen input data:

$H_1$ $$\text{Sum} = 0.6*0.06 + 0.1*0.07$$
$$= 0.018 + 0.007$$
$$= 0.025$$

$$\text{Output} = A(\text{Sum}) = 0.50625$$

$H_2$ $$\text{Sum} = 0.6*0.04 + 0.1*0.02$$
$$= 0.024 + 0.002$$
$$= 0.027$$

$$\text{Output} = A(\text{Sum}) = 0.50675$$

$O_1$ $$\text{Sum} = 0.50625*0.08 + 0.50675*0.05 + 1*0.01$$
$$= 0.0405 + 0.0253375 + 0.01$$
$$= 0.0758375$$

$$\text{Output} = A(\text{Sum}) = 0.51895$$

$O_2$ $$\text{Sum} = 0.50625*0.07 + 0.50675*0.09 + 1*0.06$$
$$= 0.0354375 + 0.0456075 + 0.06$$
$$= 0.141045$$

$$\text{Output} = A(\text{Sum}) = 0.53520$$

During the training process, the synaptic weights are adjusted to minimize the error of the output. Thus, the final synaptic weights of the trained model are only known once model training is complete. After successful training of the model, the finalized synaptic weights are then used to make predictions.

Training the NNM

The server 2014 applies machine learning algorithms to modify the synaptic weights of each model's connections as it learns the patterns in the data. Thus, trained models in the system are system models with finalized synaptic weights that result in the most minimal error. Training algorithms along with representative data sets presented to each of the models for the purpose of training are employed by the system to update the synaptic weights of each model's connections with values that minimize the error.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\Sigma_n E^2}{n}$$

The mean square error (MSE) is the sum the square of all local errors divided by the total number of cases.

Sum of Square Errors (ESS)

$$\frac{\Sigma_n E^2}{2}$$

The sum of square errors (ESS) is the sum of the square of all local errors divided by two (2).

Root Mean Square Error (RMS)

$$\sqrt{\frac{\Sigma_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 35:
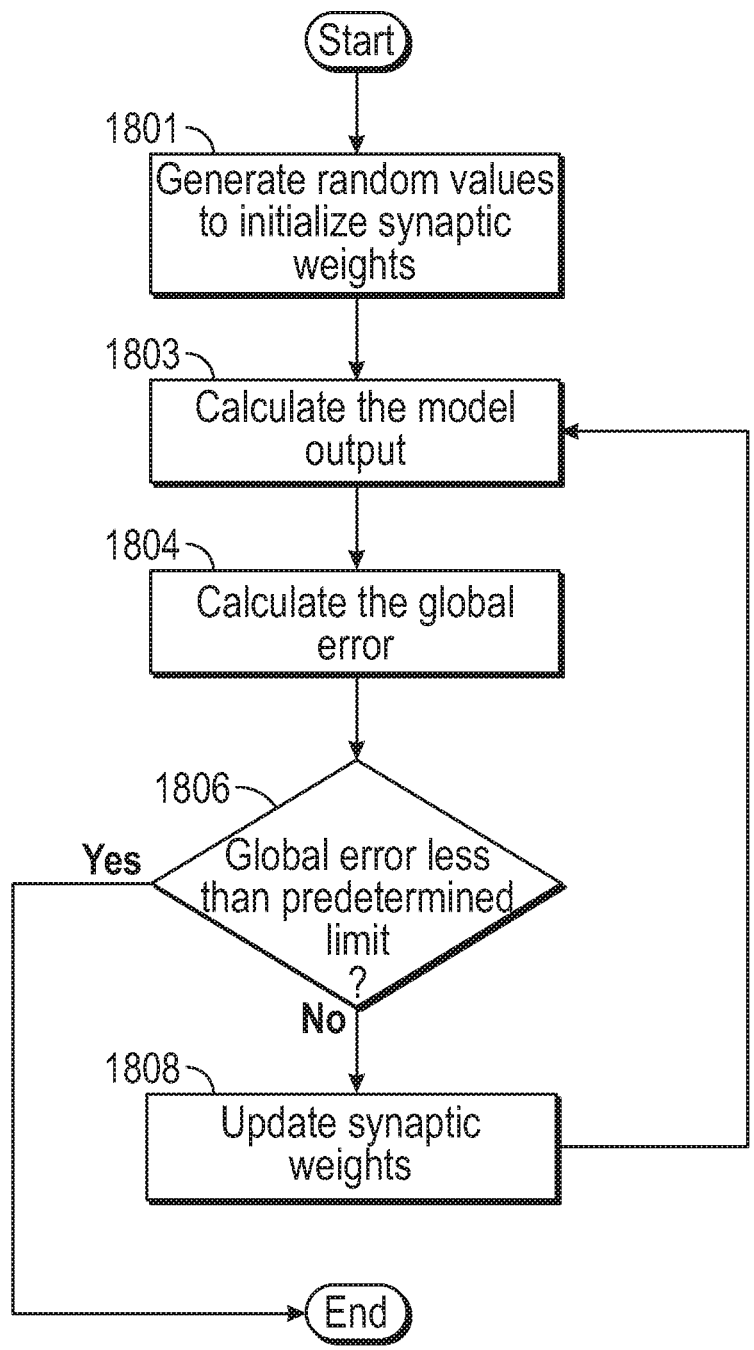
FIG. 35 is a flow diagram illustrating exemplary operations of the system for training the NNM.

Referring to FIG. 35, the approach for training the NNM based upon training data will be discussed. The training data is quantifiable outcomes (delayed or not delayed, delay time) of a plurality of past patient events and patient attributes of each of the past patient events. Initially, at 1801, values of the plurality of synaptic weights are assigned to random values. At 1803, the output values of the model are calculated for the current "row" or case in the training data being used for the current training iteration (i.e. "row" being the one event or case used for the current training iteration out of the available events in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another patient event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 36:
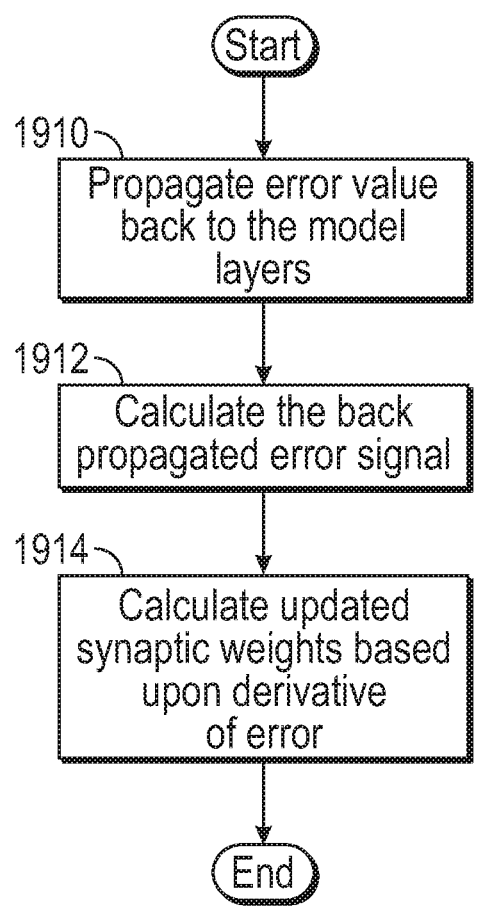
FIG. 36 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 36, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

Figure 37:
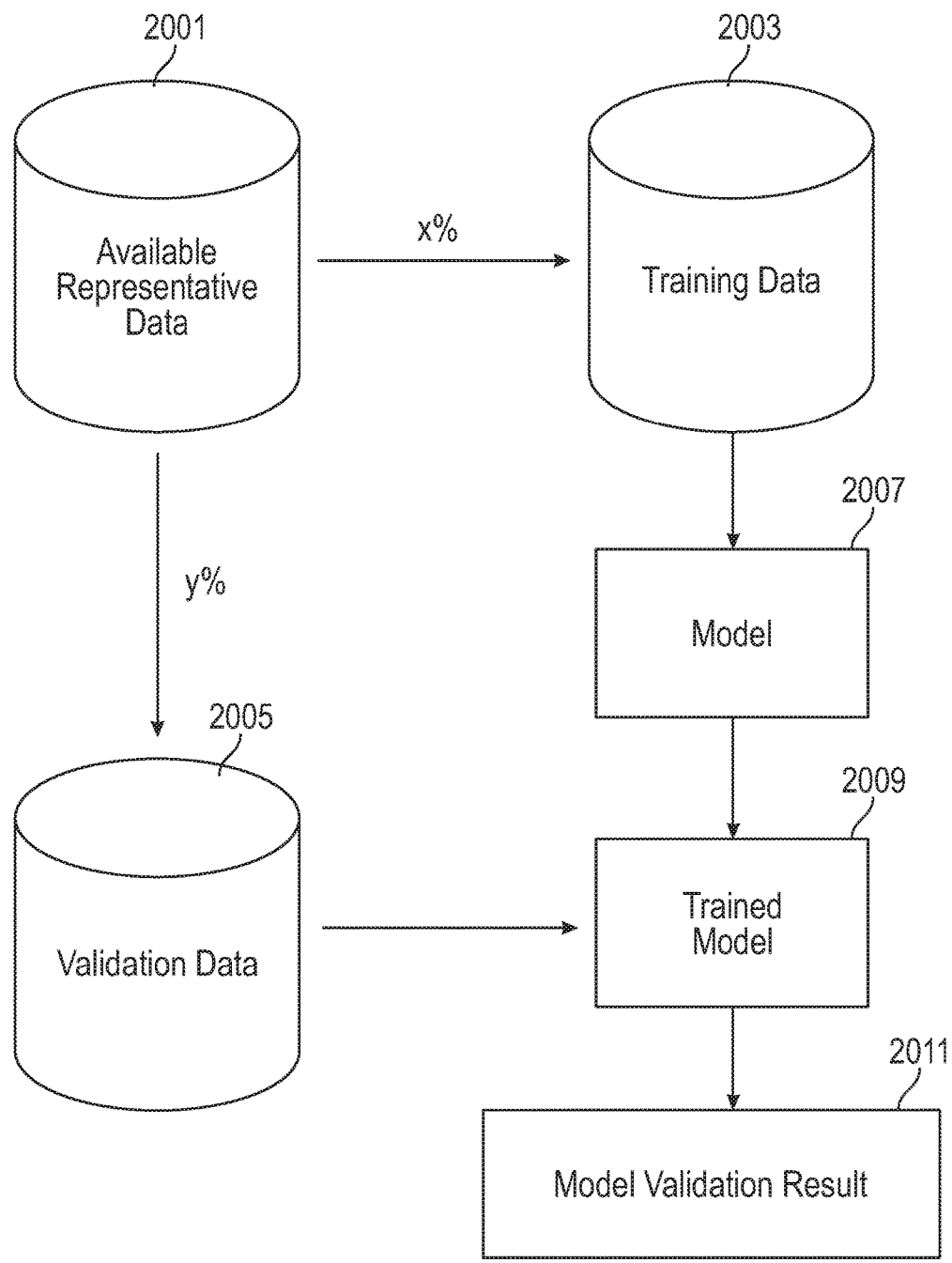
FIG. 37 is block diagram illustrating high level operations of the process for training the NNM and validating the trained NNM.

The training process for the NNM employs a representative data set, which can be a plurality of past patient events as discussed above. Referring to FIG. 37, the cases in the representative data set 2001 are divided into two unique data sets by some ratio or percent x allocated to the training data set 2003 and percent y allocated to the validation data set 2005. The ratio of cases allocated to the training data set 2003 versus those allocated to the validation data set 2005 varies. Before the allocation of cases to the training data set 2003 or the validation data set 2005, an optional step of data shuffling can be carried out by the system to help ensure all types of data in the representative data set 2001 gets distributed to both the training 2003 and the validation 2005 data sets. The training data set 2003 was used to train the NNM 2009 as discussed above. The validation data set 2005 can be used to validate the trained NNM 2009 because the real outcome of each case in the validation data set is known. The server can generate an output value (model validation result) 2011 of the trained NNM 2009 for each past patient event of the validation data set 2005, wherein each of the output values 2011 represents a calculated quantifiable outcome of the respective patient event. Then the server can determine if the output values 2011 correspond to the quantifiable outcome within the predetermined global error.

The training data set 2003 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2009 is then used to predict the outcome for cases in the validation data set 2005, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

Returning to FIG. 38A, the backend device receives a plurality of input attributes of a new patient event. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a delay risk category (classification task) or a value such as the probability of delay or the predicted duration of delay (regression task) to predict the outcome. For example, in the simplest case the de-normalized output value can be a Boolean value (delayed or not delayed). In another case, the output value can be a probability of delay occurring. In this case, the TMD or server may assign probability ranges which define particular delay categories. In another case, the output value can be a calculated delay time (predicted duration of delay). In this case, the TMD or server may assign time ranges define particular delay categories.

Unsupervised Learning

Figure 38A:
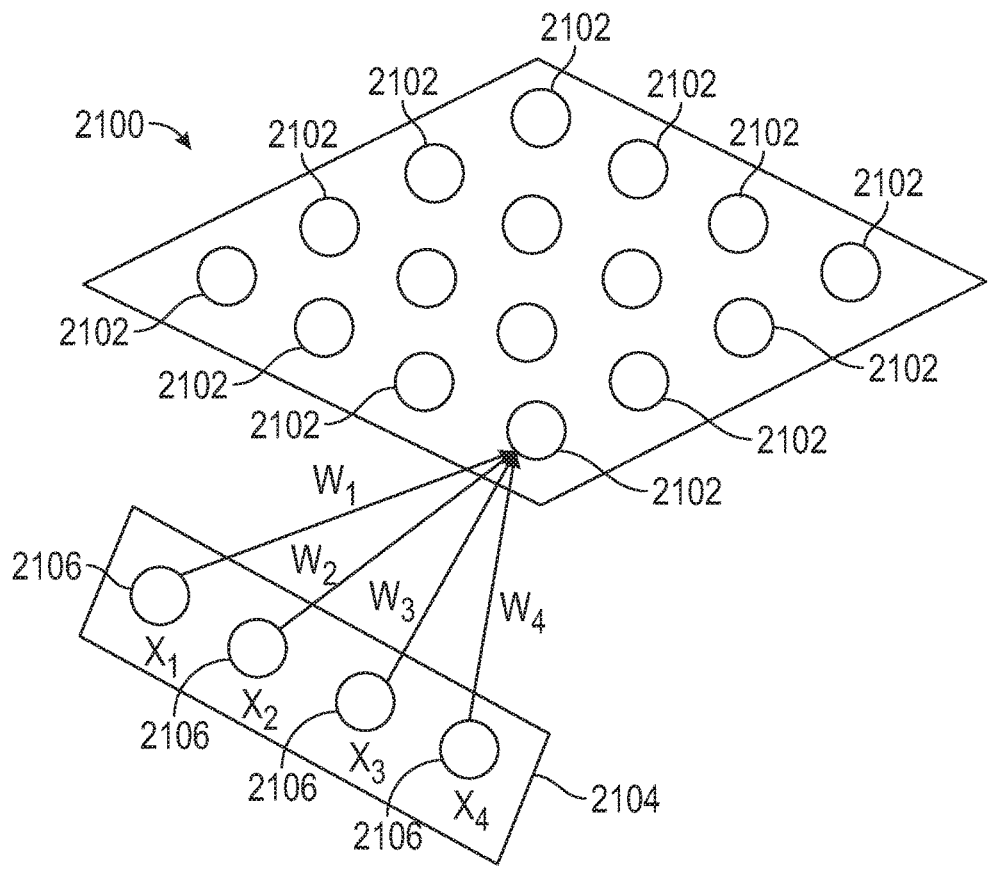
FIGS. 38A-38B is an illustration of an exemplary Self-Organizing Map (SOM) and the input data set to the SOM network.
Figure 38B:
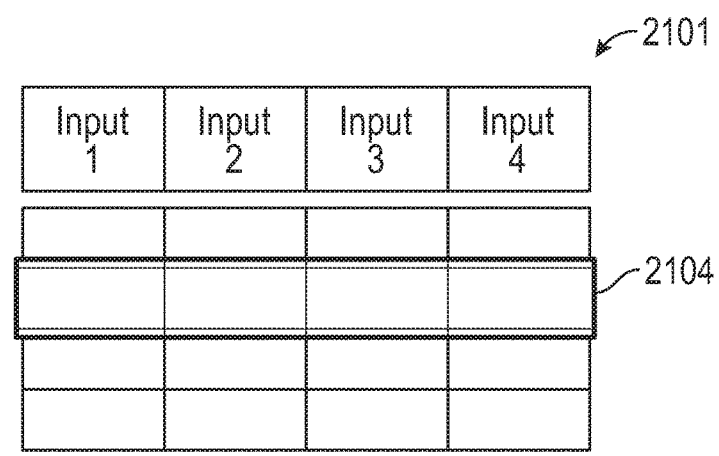
Figure 38C:
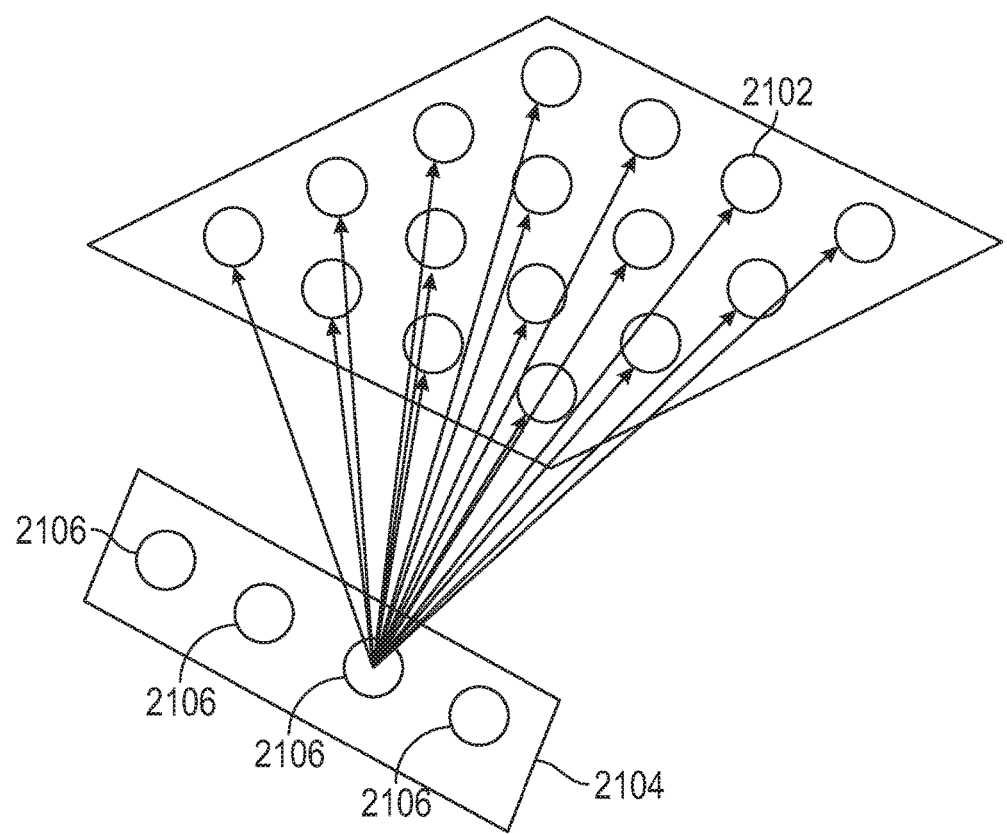
FIG. 38C is an illustration of how each node of the SOM network will contain the connection weights of the connections to all connected input nodes.

The server can also use unsupervised learning techniques as well as supervised learning techniques to determine the group or cluster to which particular patient events belong. Referring to FIGS. 38A-38B, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 38B). The specific number of inputs is dependent on the specifics of the data set. Each input node is connected to every node of the two (or three) dimensional SOM network (FIG. 38C) and each connection has a synaptic connection weight (w), much like that in supervised networks. Each node 2102 of the SOM network 2100 will contain the connection weights of the connections to all connected input nodes. As partially shown in FIG. 38C, each SOM network node 2102 is connected to all input nodes 2106, thus each node of the SOM network will have an equivalent number of connection weights (equivalent to the number of input nodes).

Figure 40:
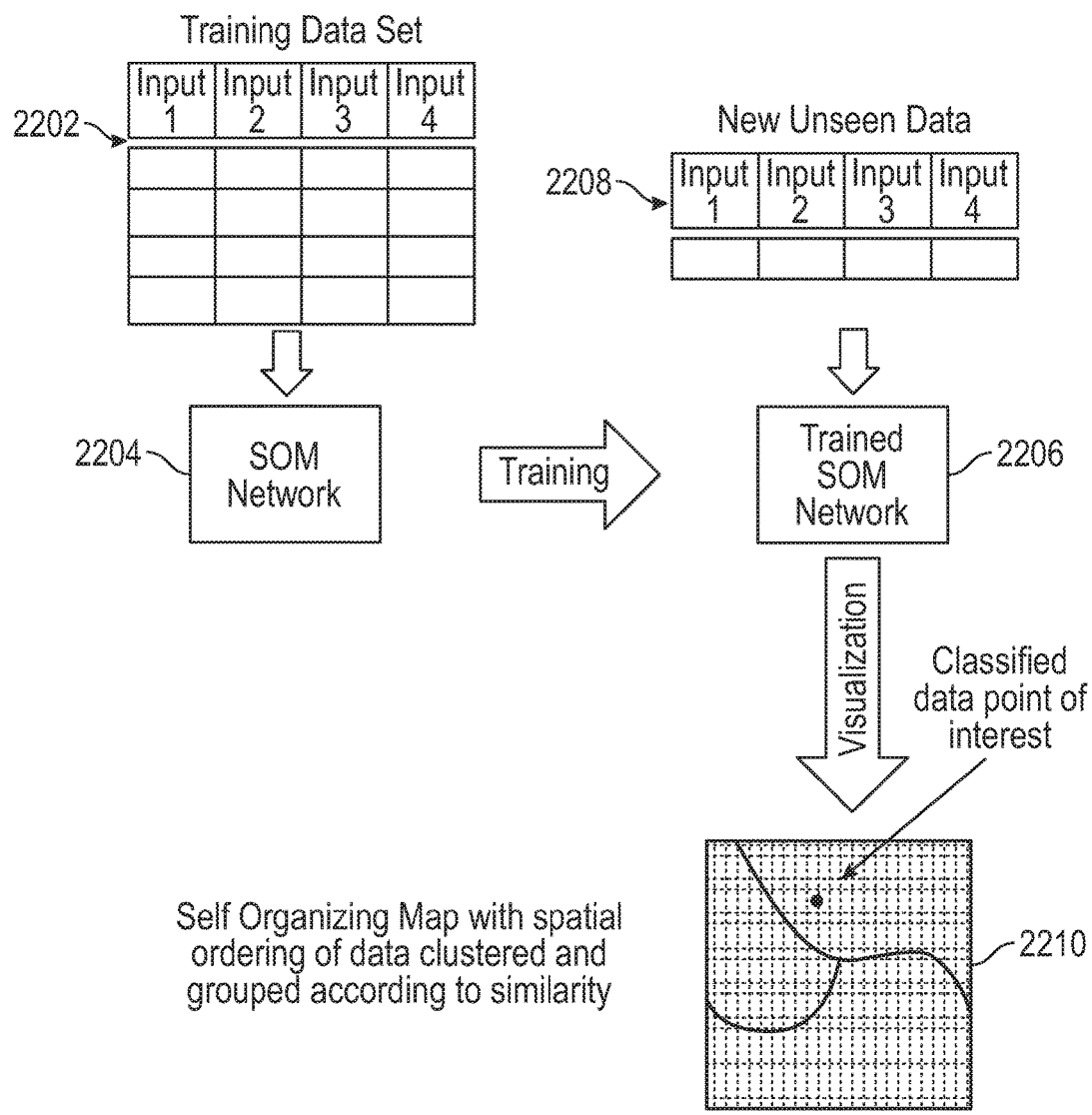
FIG. 40 is a block diagram illustrating high level operations of the process for training the SOM.

A representation of the process for creating, training and using the trained model is shown in FIG. 40. A training data set includes a plurality of patient attributes of past patient events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. As discussed later, the SOM image 2210 can be rendered on a client device.

Figure 41:
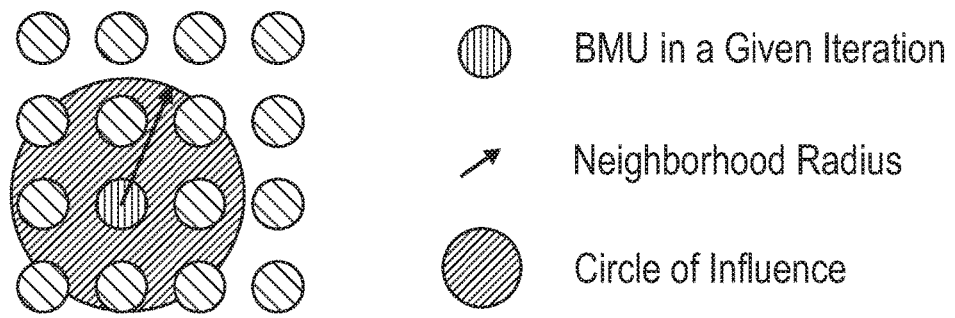
FIG. 41 is an illustration of the process for training the SOM network.

Referring to FIG. 41, the first step in SOM model training is to initialize values of the plurality of synaptic connection weights to random values. The next step is to randomly select one row (one past patient event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-\left(\frac{n}{\lambda}\right)}$$

$r_0$ = initial radius $n$ = iteration number $\lambda$ = time constant

Usually a large initial radius value is selected for the purpose of having the almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1) = W_k(n) + \alpha(n) h_{ck}(n)[x(n) - W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n)-W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Figure 39:
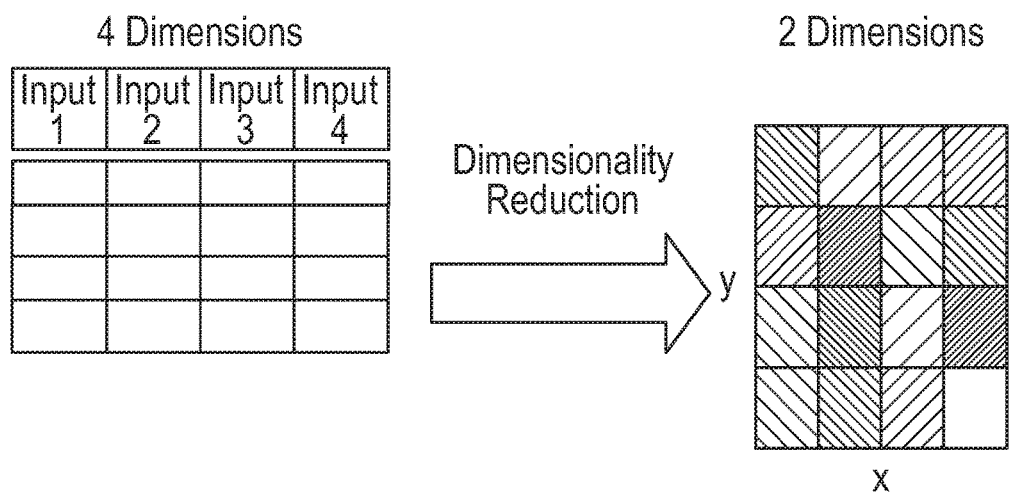
FIG. 39 is an illustration of the SOM network used to reduce dimensionality of the input data sets.

Referring to FIG. 28B, an exemplary data set includes a plurality of data [1,2 . . . N], and a number of properties [1,2 . . . N] for each data. The data set can be a plurality of past patient events and the properties can be a number of attributes of each past patient event. The high dimensionality of the data sets can make visualization of the data difficult. As illustrated in FIG. 39, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multidimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 42:
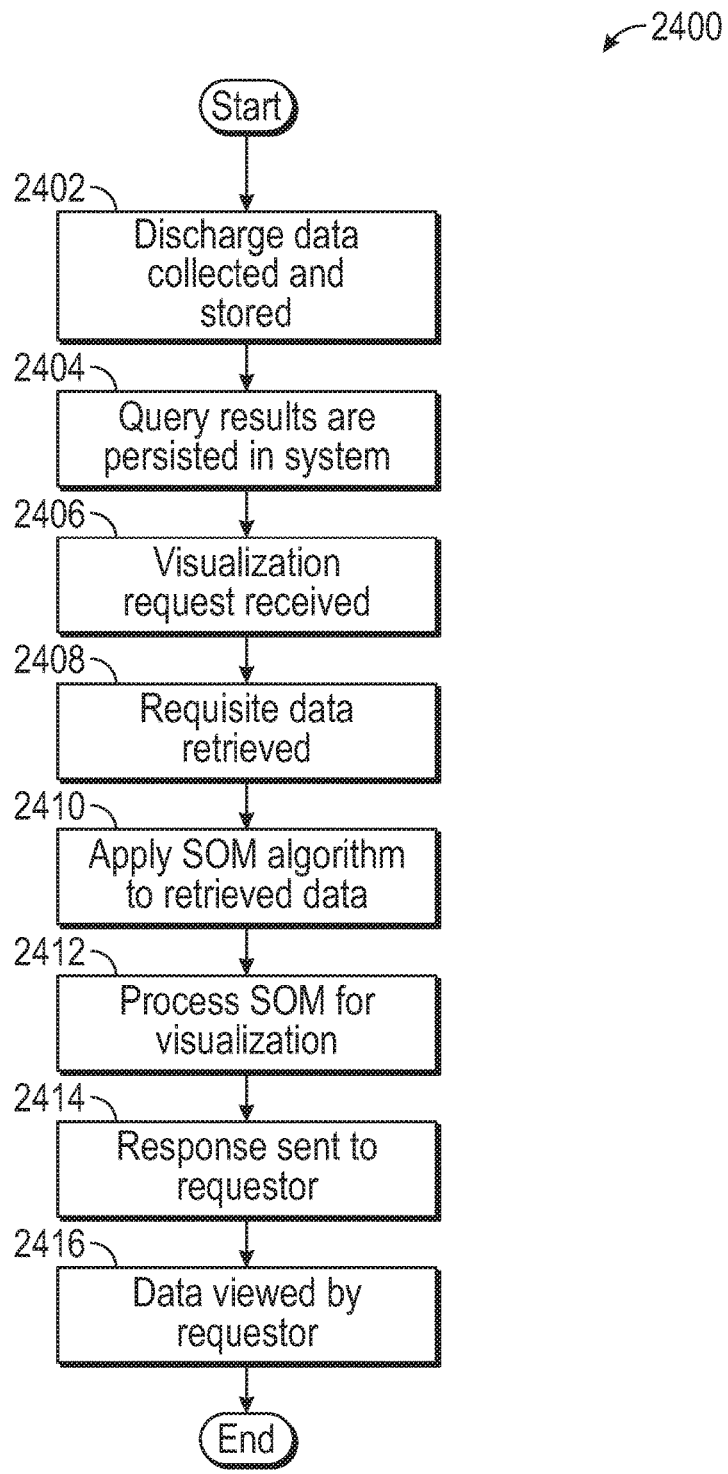
FIG. 42 is a flow diagram illustrating exemplary operations of the system to generate the graphical image including the visualization.

Referring to FIG. 42, an exemplary process 2400 by which the system can employ SOM network to take a data set of discharges defined by n-dimensional input attributes and generate a visualization of the results after passing the data into a SOM network will be discussed. At 2402, discharge data is collected and stored. Particularly, the DCE collects location data on the patient from the RFID tags as discussed above and transmits it to the backend devices. This data can be stored in the database at the server with respect to the patient as discussed above. At 2404, the server (or TMD) can maintain query results in the memory. At 2406, the TMD receives a visualization request from a client device or web browser via the network with query parameters. At 2408, the TMD sends a data request with the query parameters to the server, which retrieves from the database the data sets consistent with the request. At 2410, the server inputs the data sets to the trained SOM network. At 2412, the server generates a visualization or graphical image based upon the output from the SOM network. At 2414, the server sends the graphical image to the TMD, which either sends it to the client device and/or renders the image on a display of a website. The output produced can be groupings or clustering of discharges with similar characteristics, much like the classical "market segmentation" or "document classification" tasks for which SOMs are widely employed. This SOM output can be generated from a variety of vantage points or perspectives with one or more specified criteria, for example, specific time ranges, or for only delayed discharges, or only for a particular subset of discharges processed by a particular employee, a group of employees, a service line, a group of service lines, a hospital facility or a group of hospital facilities in a given region, to name a few examples. SOM techniques can also be employed to predict the classification, type, or grouping of a particular pending hospital discharge leveraging the attributes or inputs from an already existing data set of discharges, for example.

Exemplary Implementation

An exemplary implementation will be discussed for a case in which a NNM is created, trained and validated to determine whether a given patient discharge is likely to be delayed. This example was selected for its simplicity and the inputs were crafted to be of a flavor that is easily understood by a human, while also still being demonstrative of the inventive system's capabilities. The example is not intended to denote or to imply any limitation to the scope of attributes consumed as inputs by the system nor the scope or extent of the system's outputs and its ability to predict these outputs. While in practice the models will be more complicated, the embodiment herein is demonstrative of the modeling process (the process of developing the neural network architecture) utilized in the inventive system. The example of the model's implementation, training, and validation is provided utilizing the c# programming language (Microsoft) and an open source machine learning library (Encog). However, the neural network models can be implemented in any variety of computer languages or logic and can be trained utilizing appropriately selected machine learning training algorithms as implemented in a variety of $3^{rd}$ party libraries or in-house proprietary code. The exemplary embodiment herein is a simple feed forward neural network.

The backend devices (TMD and server) can be employed by healthcare systems to predict the likelihood of discharge delays. For example, the database at the server device can store historical discharge data from a hospital. Each of these historical discharges provide input data, specifically an attribute about the patient, an attribute about the patient's attending physician (MD), an attribute about the patient's assigned nurse, and an output, namely whether the discharge was significantly delayed or not. In this simple example, the patient attribute is the presence of polypharmacy. For this example, we will define polypharmacy as more than 20 discharge medications. The admitting attending physician attribute is whether or not the attending physician is also the patient's outpatient primary care provider (PCP). Finally, the nurse attribute in the input data set is also a binary input, specifically whether or not the nurse (RN) assigned to the care of the patient at the time of discharge is an experienced nurse (i.e. not a new hire, where a new hire is defined as a newly minted nursing school graduate—just earned his or her Bachelors of Science Degree in nursing within the last 6 months—who is a new hire to the healthcare system in their current role for less than 4 weeks). The existing data set available is that shown in the table below where the number 1 denotes the presence of the attribute and 0 denotes the absence of the attribute.

| Input 1: + Polypharmacy | Input 2: + Admitting MD is PCP | Input 3: + Patient's assigned RN is experienced | Output: + Discharge Significantly Delayed |
|---|---|---|---|
| 1 | 1 | 0 | 0 |
| 1 | 0 | 1 | 0 |
| 1 | 1 | 1 | 0 |
| 1 | 0 | 0 | 1 |
| 0 | 0 | 0 | 0 |
| 0 | 0 | 1 | 0 |

| Input 1: + Polypharmacy | Input 2: + Admitting MD is PCP | Input 3: + Patient's assigned RN is experienced | Output: + Discharge Significantly Delayed |
|---|---|---|---|
| 0 | 1 | 0 | 0 |
| 0 | 1 | 1 | 0 |

As shown below, the input data set training data and the output data from the above table is next put into an array of double arrays. One is created for the input data and one is created for the output data.

```
namespace _006_1.ExemplaryEmbodiment
{
    class Program
    {
        static void Main(string[ ] args)
        {
            double[ ][ ] exemplaryEmbodimentInput =
            {
                new[ ] {1.0, 1.0, 0.0},
                new[ ] {1.0, 0.0, 1.1},
                new[ ] {1.0, 1.0, 1.0},
                new[ ] {1.0, 0.0, 0.0},
                new[ ] {0.0, 0.0, 0.0},
                new[ ] {0.0, 0.0, 1.0},
                new[ ] {0.0, 1.0, 0.0},
                new[ ] {0.0, 1.0, 1.0}
            };
            double[ ][ ] exemplaryEmbodimentOutput =
            {
                new [ ]{0.0},
                new [ ]{0.0},
                new [ ]{0.0},
                new [ ]{1.0},
                new [ ]{0.0},
                new [ ]{0.0},
                new [ ]{0.0},
                new [ ]{0.0}
            };
```

The crux of any application of machine learning is development of an appropriate model for the problem that needs to be solved. as shown below, for the simplistic example, a simple feed forward neural network is used. The neural network includes an input layer with three input nodes in the input layer, a hidden layer and an output layer. For each input neuron, no activation function is specified (note null value); alternatively a linear activation function could have been employed instead, as a linear activation function simply would mirror the input. A hidden layer is also specified for the model, containing three neurons as well as bias neuronal input. For each hidden layer neuron, the Sigmoid activation function is specified. Finally, for the current problem, one output neuron is required in the output network layer. No bias neuronal input is included, and again the Sigmoid activation function is specified. Once the networks neuronal layer architecture has been defined, the network is finalized and the synaptic weights are initialized to random values.

```
private static BasicNetwork Create Network( )
{
    var network=new BasicNetwork( )
    //input layer, 3 neurons, with bias neuron, no activation fxn
    network.AddLayer(new BasicLayer(null, true, 3));
    //hidden layer, 3 neurons, with bias neuron, sigmoid activation fxn
    network.AddLayer(new BasicLayer(new ActivationSigmoidQ, true, 3));
```

```
//output layer, 1 neuron, no bias neuron, sigmoid activa-
tion fxn
    network.AddLayer(new BasicLayer(new ActivationSig-
moidQ, false, 1));
    network.Structure. FinalizeStructureQ;
    //randomly initialize network synaptic weights
    network. Reset( );
    return network;
}
var network=Create Network( )
```

RGiven the neuronal architecture is now finalized, the model is ready for training. For this exemplary embodiment a first order resilient propagation (RProp) supervised learning algorithm, is utilized to train the model. The training data set is passed into the neural network which has been configured with the RProp training algorithm.

```
var trainingSet=new BasicMLDataSet(exemplaryEmbodi-
mentInput, exemplaryEmbodimentOutput);
//training algorithm that will be used to train the network
var train=new ResilientPropagation(network, trainingSet);
```

A predefined acceptable global error value of global error less than or equal to 0.001 has been decided upon and is used as the training iteration terminating condition for the do while loop. Multiple training iterations are executed and the global error at the end of each iteration is determined and assessed to see if it meets the established terminating condition. If an acceptable global error level has not yet been achieved, the synaptic weights for each interneuron connection in the network will be subsequently adjusted and another training iteration then ensues. This process is continued until the updated synaptic weights in a given training iteration yield an output with global error less than the predefined condition. Once this terminating condition is met, the end result is the trained model.

```
//TRAIN THE MODEL
var epoch=1;
do
{
    //initiated training iteration
    train.Iteration( );
    //write iteration number and training error to console
    Console.WriteLine("Iteration No {0}: \tError: {1}",
epoch, train.Error);
    //epoch will increase by 1 in each iteration
    epoch++;
    //check value of training error at end of each iteration
(terminating condition)
    //predefined limit value set to 0.001
} while (train.Error>0.001);
```

Referring to FIG. 43, the output of each training iteration in this demonstrative example is shown. A total of 21 training iterations were required before an acceptable global error level was attained.

Now that the exemplary neural network model is trained and "learned," it is ready to undergo validation. For the purpose of this exemplary embodiment, the training data is passed into the trained model to assess its performance.

```
//EVALUATE THE MODEL
//in this simplistic exemplary embodiment we pass the
model the training data
//set again
foreach (var item in trainingSet)
{
    //pass in row in data set
    var output=network.Compute(item.Input);
    //write output to console
    Console.WriteLine(
        "Input: {0:0.0}, {1:0.0}, {2:0.0}"+
        "\tIdeal: {3:0.0}"+
        "\tPredicted: {4}",
        item.Input[0],
        item.Input[1],
        item.Input[2],
        item.Ideal[0],
        output[0]);
}
```

The trained model's performance with this training data set are shown in FIG. 44. For each input, the trained model's predicted output nicely approximates the ideal output providing evidence that the model is performant at predicting the outcome in all presented cases.

Figure 47:
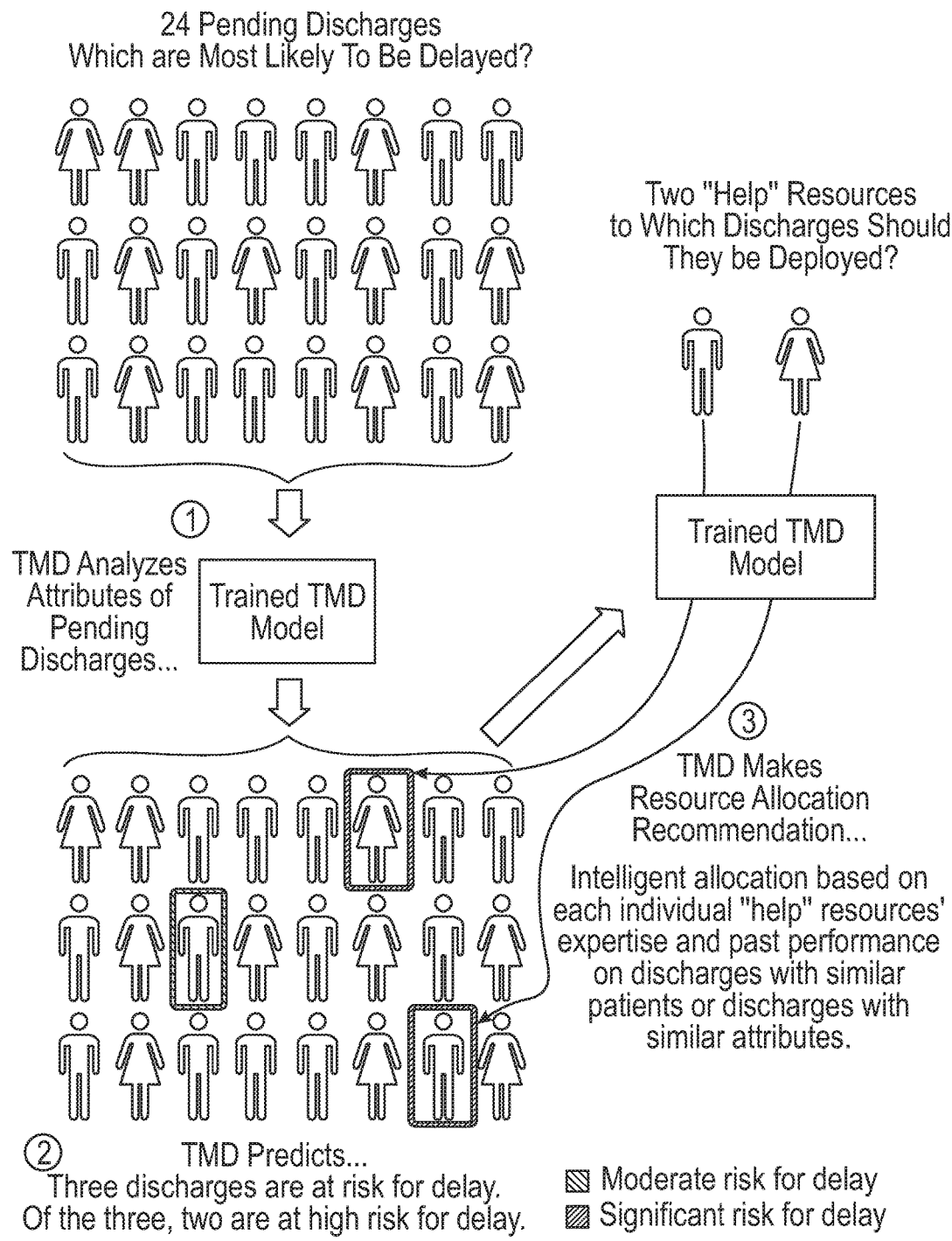
FIG. 47 is an illustration of an exemplary use case in which the trained TMD device determines a delay risk for a plurality of patient events and to which of the patient events resources should be deployed.

Referring to FIG. 47, the backend devices (TMD and server) use NNMs to predict which events are at risk for delay (i.e. which patient discharges for which orders have been written are at risk for delay) as described elsewhere herein. In addition, as illustrated in FIG. 47, the backend devices are capable of using their NNMs to determine to which, if any, events more resources should be allocated (i.e. the backend devices can determine whether there is an opportunity, or more specifically, a high probability, of successfully mitigating the likelihood of a given predicted discharge delay by allocating additional resource(s)). Particularly, to do this, the controller of the TMD may utilize a NNM that takes inputs such as delay risk category (moderate or significant risk for delay) of the patient event, attributes of the patient and the patient's hospital stay, the service line the patient is on, attributes of available clinical resources (for example, the available help resources' expertise and past performance on discharges with similar patients or discharges with similar attributes), etc.

In doing so, the TMD can determine whether (the probability that) deployment of any given available resource(s) is likely to mitigate the predicted discharge delay for a given patient discharge event that is pending fulfillment; moreover, the TMD's NNMs can predict the quantity or duration of time by which the delay would potentially be reduced if a given resource allocation recommendation is made. Based on business logic and these results, the TMD may determine it does or does not recommend that any of the available additional resources be deployed. There are a number of approaches the TMD could take to arrive at a decision to recommend or not recommend the deployment of any available resource(s). One demonstrative approach the TMD might take would be to recommend the deployment of an available resource if the probability weighted reduction in the duration of the predicted delay exceeded a particular threshold. If more than one potential allocation of available resources might be feasible at any given time, the business logic of the TMD, for example, could be configured such that the TMD issues the recommendation that in the net (summed together) results in the largest probability weighted delay reduction for the hospital system as a whole at that moment—i.e. the constellation of recommendations at that moment that collectively has the maximum potential beneficial impact (probability weighted delay duration reduction) for the hospital in question. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The resource allocation example herein is not intended to limit the scope of potential approaches to that described.

Referring to FIG. 48, the system provides a user interface users can use or alternatively the user can author code for a client that will directly communicate with an application programming interface (API) exposed by the backend devices with access regulated via the use of a security token and/or an API key that references the developer's organization to configure particular metrics (related to the relationships and events the system captures) that they desire to follow and measure over time and in real time. Each metric can also be associated with an icon (not shown) and the user can configure particular colors for the icon (not shown) or a cell where a given metric value is displayed (shown) that would correspond to particular values of or value ranges for the respective performance metric. The end user can configure one or more target levels of performance for each metric that may or may not correspond with some description of the level of performance. The system allows end users to provide meta-data about the performance metric as well (i.e. descriptive attributes about the performance metrics).

The system can be integrated into third party clinician/healthcare provider/patient facing applications running on a client device. The client applications may incorporate icons with our without categorical color designations or data tables with or without color encoded cells to communicate information about a given metric or concept. Business logic for the display color can be utilized by the client application on any given client device. The icons (not shown) or data tables with metric values (shown) can appear in the client application in association with various combinations of healthcare providers, patients, patient visits, patient facility visits, patient provider encounters, etc. The colored icon and/or color encoded data table can appear in various areas of a given client application to prompt the user and communicate information about the current value or metric being reported relative to a target, benchmark, or standard of care. For example, if based on the logic of the TMD, the fulfillment of a given discharge that is ordered by a physician is predicted to be significantly delayed, moderately delayed, or negligibly delayed, the client device application can output a display that shows an icon with a particular color determined by and used to communicate the specific categorization of the predicted delay, if any. To provide an example of their use, the icons could appear next to the particular discharge it references among other discharges in a list of pending (yet to be fulfilled) discharge orders. The colored icon, to provide another example, could alternatively appear next to a patient on a user interface that displays all the patients on a given ward; in this exemplary case, the colored icon would communicate the existence of a discharge order (communicated by the icon's presence) and whether the pending discharge is predicted to be at risk for delay, and if predicted to be at risk for delay the category of delay risk (communicated by the icon color). In such scenarios, the color of the icon would serve the purpose of communicating the predicted delay categorization to end users that may be viewing the information.

The performance metric, predictions, and other data generated by inventive system can be accessed via the backend device API and pulled into other third party user facing applications. The data can also be viewed by an authenticated and authorized end user in the graphical user interface of one of the system's client devices. Various views and transformations of the performance metric data can be provided.

The system enables its customers and end users to gain insights about their performance on various metrics of interest and to predict particular outcomes of interest. The customers/end users can slice the data and view it from perspectives that are of particular value to their organization. Within many healthcare organizations a plurality of healthcare workers are involved in the care of a given patient. One benefit of the system is its ability to report relevant data it generates based on relationships between a plurality of related or unrelated healthcare workers and information in the system related to them (for example, any interactions the healthcare workers may have had with specific patients, during particular patient-visits at particular locations or facilities, and various related data or attributes about each of these that the system captures) over particular time ranges of interest. One of the system's client devices that communicates with the backend device can produce a dashboard tailored to the logged in end user's desired settings (i.e. which metrics to show, for what time ranges, etc.) and any restrictions thereof resulting from settings configured by authorized system administrators. End users can have saved views in addition to a system or user set default view. The end user can create ad hoc views as well, and save them as saved views. If the user is authorized and authenticated, he or she can access a dashboard similar to the exemplary dashboard shown in FIG. 48. The end user can interact with the dashboard to view the various metrics from different perspectives (drill up/drill down, change time range, view raw underlying data, etc.). The user can do this using various client device peripherals (touch screen, key board, mouse, microphone—voice commands . . . i.e. voice data that is streamed to a voice to text engine, transcribed, and interpreted by a machine, etc. For example a user could verbally "ask" that particular metric(s) of interest be fetched and shown in accordance with any criteria verbally provided and based upon parsing of the transcript returned, the system would attempt to fulfil the transcribed verbal request). One of the system's client devices can also be configured and used to operate a monitor or television (i.e. a large, flat screen monitor or TV). The client device's controller can run instructions native to the device or remotely received from the backend device to display data and metrics on the large screen graphical user interface. The client device may show a pre-defined sequence of metrics which loops and plays continuously or an authorized end user can interact with the client device via the large screen graphical interface. The large screen graphical user interface can be place in a secured area within a healthcare provider organization where access is controlled and only authorized personnel can enter (for example, an executive suite, physician lounge, operating room, operating room lounge, etc.) and be used to communicate real time data and various performance metrics of interest that are being tracked by the system. The large screen graphical user interface can also be used and controlled by an authenticated and authorized end user during a meeting to display information or be used as a part of a virtual meeting (i.e. a web conference call).

The TMD or a client device running an application that communicates with the TMD can generate a graphical display similar to the exemplary one shown in FIG. 48 which displays an average discharge (D/C) lag for various levels of a healthcare system, as well as the percentage of discharges that had a D/C lag that was at or below goal. Particularly, a client device can request this graphical display from the TMD or the underlying data required to generate it. The TMD can store the D/C lag values or calculate them from data retrieved from the database of the server device. While the D/C lag is the metric shown in FIG. 48, this example is not intended to denote or to imply any limitation to the scope of metrics tracked or generated by the inventive system that may be displayed in a similar report. Moreover, data like that shown in FIG. 48 can also be used to generate performance evaluations of particular personnel (such as nurses or physicians) using a variety of reporting criteria such as patient event types, date ranges, etc.

Therefore, the present disclosure concerns machine learning models, the disclosure's application of specific technical techniques that leverage the specific aspects or attributes of particular care transitions in hospital systems in conjunction with the other system components (for example, the RFID tag interaction with the DCE and the DCE's communication with the TMD) that permit the identification of the true state of healthcare facility operations.

While only certain features of the invention have been illustrated and described herein, many modifications and changes will occur to those of ordinary skill in the art. The following claims are intended to cover all such modifications and changes.

What is claimed is:

1. A system comprising:
a plurality of radio-frequency identification (RFID) chips, wherein a first RFID chip of the plurality of RFID chips is a passive-type RFID chip;
a data collection engine (DCE) device communicating with the plurality of RFID chips, wherein the DCE comprises:
a power transmission subsystem including a power source and an antenna arranged to wirelessly transmit power from the power source to the first RFID chip;
a transceiver configured to receive first data from at least one of the first RFID chip and a second RFID chip of the plurality of RFID chips while the first RFID chip is activated by the power received, the first data including identification information of the at least one of the first and second RFID chips, one or more pressure values or position information;
a controller operatively coupled to the transceiver; and
one or more memory sources operatively coupled to the controller, the one or more memory sources including instructions for configuring the controller to generate one or more messages indicative of the identification information to be sent by the transceiver to a server device via the network connection,
wherein the first RFID chip includes an antenna for wirelessly receiving the power from the transceiver of the DCE and control logic for generating the identification information;
wherein the server device comprises:
a transceiver configured to receive the one or more messages from the DCE;
a controller operatively coupled to the transceiver; and
one or more memory sources operatively coupled to the controller, the one or more memory sources storing a trained neural network model (NNM) for generating an output value corresponding to a present event based upon one or more of the one or more pressure values or position information.

2. The system of claim 1, wherein in the server device:
the one or more memory sources further store a plurality of past events, each of the plurality of past events including a plurality of attributes and a quantifiable outcome; and
the controller further configured to:
train a neural network model (NNM) to generate the trained NNM, wherein the training of the NNM includes:
performing pre-processing on the plurality of attributes for each of the plurality of past events to generate a plurality of input data sets;
dividing the plurality of past events into a first set of training data and a second set of validation data;
iteratively performing a machine learning algorithm (MLA) to update synaptic weights of the NNM based upon the training data; and
validating the NNM based upon the second set of validation data,
wherein the MLA for updating the synoptic weights is one or more of ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), support vector machines, genetic programming, Bayesian statistics, decision trees, case based reasoning, information fuzzy networks, clustering, hidden Markov models, particle swarm optimization, simulated annealing.

3. A method for predicting an outcome associated with a new event, the method comprising:
receiving a plurality of input attributes of the new event;
performing pre-processing on the plurality of input attributes to generate an input data set;
generating an output value from a trained model based upon the input data set; and
classifying the output value into a delay risk category to predict the outcome.

4. The method of claim 3, further comprising:
storing a plurality of past events, each of the plurality of past events including a plurality of patient attributes and a quantifiable outcome; and
training a neural network model (NNM) to generate the trained model, wherein the training of the NNM includes:
performing pre-processing on the plurality of patient attributes for each of the plurality of past events to generate a plurality of input data sets;
dividing the plurality of past events into a first set of training data and a second set of validation data;
iteratively performing a machine learning algorithm (MLA) to update synaptic weights of the NNM based upon the training data; and
validating the NNM based upon the second set of validation data,
wherein the MLA for updating the synoptic weights is one or more of ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), support vector machines, genetic programming, Bayesian statistics, decision trees, case based reasoning, information fuzzy networks, clustering, hidden Markov models, particle swarm optimization, simulated annealing.

5. The method of claim 4, wherein:
the NNM includes an input layer, output layer, and a plurality of hidden layers with a plurality of hidden neurons; and
each of the plurality of hidden neurons includes an activation function, the activation function is one of:
(1) the sigmoid function $f(x)=1/(1+e^{-x})$;
(2) the hyperbolic tangent function $f(x)=(e^{2x}-1)/(e^{2x}+1)$; and
(3) a linear function $f(x)=x$,
wherein x is a summation of input neurons biased by the synoptic weights.

6. The method of claim 4, wherein the NNM is one or more of a feed forward structure Neural Network; ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), and Radial Basis Function Network.

7. The method of claim 4, wherein the performing of the MLA includes measuring a global error in each training iteration for the NNM by:
calculating a local error, the local error being a difference between the output value of the NNM and the quantifiable outcome;
calculating the global error by summing all of the local errors in accordance with one of:
(1) Mean Square Error (MSE) formula $$\frac{\sum_n E^2}{n};$$

(2) Root Mean Square Error (RMS) formula $$\sqrt{\frac{\sum_n E^2}{n}};$$

and
(3) Sum of Square Errors (ESS) formula $$\frac{\sum_n E^2}{2},$$

wherein n represents a total number of the past events and E represents the local error.

8. The method of claim 3, wherein the trained model is a trained Self-Organizing Map (SOM) including a plurality of network nodes arranged in a grid or lattice and in fixed topological positions, an input layer with a plurality of input nodes representing the input attributes of the past events, wherein each of the plurality of input nodes is connected to all of the plurality of network nodes by a plurality of synaptic weights.

9. The method of claim 8, further comprising:
storing a plurality of past events, each of the plurality of past events including a plurality of patient attributes and a quantifiable outcome;
performing pre-processing on the plurality of patient attributes for each of the plurality of past events to generate a plurality of input data sets; and
training a SOM to generate the trained model, wherein the training of the SOM includes:
initializing values of the plurality of synaptic weights to random values,
randomly selecting one past event and determining which of the plurality of network nodes is a best matching unit (BMU) according to a discriminant function, wherein the discriminant function is a Euclidean Distance; and
iteratively calculating a neighborhood radius associated with the BMU to determine neighboring network nodes for updating, and updating values of synoptic weights for neighboring network nodes within the calculated neighborhood radius for a fixed number of iterations to generate the trained model.

10. The method of claim 9, wherein normalizing of the plurality of patient attributes includes generating another SOM including the plurality of patient attributes to reduce dimensionality.

11. The method of claim 3, wherein the receiving the plurality of patient attributes of the new event further includes receiving one or more messages including a patient identification and location information associated with a first RFID tag and a medical professional identification and location information associated with a second RFID tag from a data collection engine (DCE).

12. The method of claim 3, wherein the new event is one of an admit patient order, discharge patient order, transfer patient order, or room turnover request, and the output value is one of an estimated delay time or an indication of delay or no delay for the new event.

13. The method of claim 3, wherein:
the receiving of the plurality of patient attributes of the new event further comprises receiving a plurality of new events, each including a plurality of patient attributes;
the generating of the output value and classifying the output value further includes generating a graphical image including output values for each of the plurality of new events;
the method further comprises receiving a graphical display request from a remote client device and transmitting the graphical image to the remote client device as a response;
the trained model is a trained SOM; and
the graphical image is a cluster diagram including a plurality of clusters of output values having a similar characteristic.

14. The method of claim 3, wherein the patient attributes include:
a location of a patient of the new event received from one of an RFID associated with a patient identification for the patient and a DCE in communication with the RFID;
a medical professional identification of a medical professional associated with the patient received from an RFID associated with the medical professional;
information regarding a prior relationship between the medical professional and the patient received from a memory source;

date information of the new event;
wherein the receiving of the plurality of patient attributes of the new event further comprises one or more of the following:
receiving one or more of an age of the patient, insurance information associated with the patient and employment information associated with the patient from a memory source;
receiving information indicative of a medical specialty associated with a facility in which the patient is located from the memory source;
receiving identification information indicative of an individual that signed a event order and date information of the order from the memory source;
receiving identification information of a current attending physician of record for the patient from the memory source,
receiving information indicating presence or absence of a resident physician as a participant in a patient care episode, and
receiving information indicating a number of medications on a medication administration record at a time of the event.

15. The method of claim 3, further comprising:
assigning an allocation of appropriate clinical resources to the event based upon an optimization algorithm in accordance with the delay risk category of the event and attributes of available clinical resources.

16. A Throughput Manager Device (TMD) comprising:
a transceiver for receiving input attributes associated with an event from one or more remote entities via a network connection;
the transceiver further for receiving an information request from a remote client access device via the network connection, the information request being a request for calculated quantifiable outcomes for a plurality of events;
a controller operatively coupled to the transceiver; and
one or more memory sources operatively coupled to the controller, the one or more memory sources storing instructions for configuring the controller to:
calculate a quantifiable outcome for each of the events from a trained model based upon at least two or more patient attributes of the respective event where the outcome represents a numerical, continuous or categorical outcome; and
generate an information reply including a graphical display indicating the numerical/continuous output value or the category output of each of the events.

17. The TMD of claim 16, wherein the one or more remote entities include:
a data collection engine receiving patient identification from a first RFID tag and medical professional identification and location information from a second RFID tag;
a CPOE system;
a Hospital Bed Management System (BMS); and
an Electronic medical records system.

18. The TMD of claim 16, wherein:
the information request further includes a request for an average discharge lag for each of a plurality of facilities in a system, each of a plurality of clinical services lines in a respective facility, and for the system; and
the generating of the information reply including the graphical display further includes including the average discharge lag for each of the plurality of facilities, the each of the plurality of clinical services lines, and for the system in the graphical display.

* * * * *